United States Patent
Moore et al.

(10) Patent No.: US 12,252,723 B2
(45) Date of Patent: Mar. 18, 2025

(54) KETOREDUCTASE POLYPEPTIDES AND POLYNUCLEOTIDES

(71) Applicant: Codexis, Inc., Redwood City, CA (US)

(72) Inventors: Jeffrey C. Moore, Westfield, NJ (US); Jack Liang, South San Francisco, CA (US); Jonathan Penfield, Truckee, CA (US); Jovana Nazor, Milpitas, CA (US); Nikki Dellas, San Carlos, CA (US); Vesna Mitchell, Santa Clara, CA (US); Da Duan, Newark, CA (US); Iman Farasat, Rahway, NJ (US); Agustina Rodriguez-Granillo, Rahway, NJ (US); Grant Murphy, Rahway, NJ (US); Nicholas Marshall, Rahway, NJ (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 18/352,899

(22) Filed: Jul. 14, 2023

(65) Prior Publication Data

US 2024/0068005 A1 Feb. 29, 2024

Related U.S. Application Data

(60) Continuation of application No. 17/239,953, filed on Apr. 26, 2021, now Pat. No. 11,746,369, which is a division of application No. 16/605,576, filed as application No. PCT/US2018/027450 on Apr. 13, 2018, now Pat. No. 11,021,729.

(60) Provisional application No. 62/491,161, filed on Apr. 27, 2017.

(51) Int. Cl.
| | |
|---|---|
| *C12P 41/00* | (2006.01) |
| *C12N 9/02* | (2006.01) |
| *C12N 9/04* | (2006.01) |
| *C12N 15/70* | (2006.01) |

(52) U.S. Cl.
CPC .......... *C12P 41/002* (2013.01); *C12N 9/0004* (2013.01); *C12N 9/0006* (2013.01); *C12N 15/70* (2013.01); *C12Y 101/01002* (2013.01); *C12Y 120/01001* (2013.01)

(58) Field of Classification Search
CPC ......... C12P 41/002; C12P 7/02; C12P 17/182; C12N 9/004; C12N 9/0006; C12N 15/70; C12Y 101/01002; C12Y 120/01001; C12Y 101/01184

See application file for complete search history.

(56) References Cited

U.S. PATENT DOCUMENTS

| | | |
|---|---|---|
| 5,559,030 A | 9/1996 | Matsuyama et al. |
| 5,605,793 A | 2/1997 | Stemmer |
| 5,700,670 A | 12/1997 | Yamagishi et al. |
| 5,763,236 A | 9/1998 | Kojima et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,891,685 A | 4/1999 | Yamagishi et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,265,201 B1 | 7/2001 | Wackett et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |

(Continued)

FOREIGN PATENT DOCUMENTS

| | | | |
|---|---|---|---|
| CN | 105420306 A | | 3/2016 |
| JP | 07-231785 A | | 9/1995 |

(Continued)

OTHER PUBLICATIONS

Altschul, S., et al., "Basic local alignment search tool," J. Mol. Biol., 215: 403-410 (1990).

(Continued)

*Primary Examiner* — Ganapathirama Raghu
(74) *Attorney, Agent, or Firm* — Codexis, Inc.

(57) ABSTRACT

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

6 Claims, 6 Drawing Sheets

Specification includes a Sequence Listing.

(56) References Cited

U.S. PATENT DOCUMENTS

| | | |
|---|---|---|
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,337,186 B1 | 1/2002 | Krebber |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,399,339 B1 | 6/2002 | Wolberg et al. |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,483,011 B1 | 11/2002 | Stemmer et al. |
| 6,484,105 B2 | 11/2002 | Zhang |
| 6,489,146 B2 | 12/2002 | Stemmer et al. |
| 6,500,617 B1 | 12/2002 | Stemmer et al. |
| 6,500,639 B2 | 12/2002 | Subramanian |
| 6,506,602 B1 | 1/2003 | Stemmer |
| 6,506,603 B1 | 1/2003 | Stemmer |
| 6,518,065 B1 | 2/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,605,430 B1 | 7/2003 | Affholter et al. |
| 6,602,986 B1 | 8/2003 | Stemmer et al. |
| 6,613,514 B2 | 9/2003 | Patten et al. |
| 6,645,746 B1 | 11/2003 | Kizaki et al. |
| 6,653,072 B1 | 11/2003 | Patten et al. |
| 6,686,515 B1 | 2/2004 | Lassner et al. |
| 6,703,240 B1 | 3/2004 | Stemmer et al. |
| 6,716,631 B1 | 4/2004 | delCardayre et al. |
| 6,800,477 B2 | 10/2004 | Patel et al. |
| 6,818,752 B2 | 11/2004 | Rozzell, Jr. et al. |
| 6,825,001 B2 | 11/2004 | Wackett et al. |
| 6,902,922 B2 | 6/2005 | Ness et al. |
| 6,917,882 B2 | 7/2005 | Selifonov et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,220,566 B2 | 5/2007 | Ness et al. |
| 7,288,375 B2 | 10/2007 | Stemmer et al. |
| 7,384,387 B1 | 6/2008 | Raillard et al. |
| 7,402,419 B2 * | 7/2008 | Zhao ............... C12N 9/0004 435/71.1 |
| 7,421,347 B2 | 9/2008 | Selifonov et al. |
| 7,430,477 B2 | 9/2008 | Selifonov et al. |
| 7,462,469 B2 | 12/2008 | Bass et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,477 B1 | 1/2011 | Gustafsson et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 7,981,614 B2 | 7/2011 | Stemmer et al. |
| 8,014,961 B2 | 9/2011 | Bass et al. |
| 8,029,988 B2 | 10/2011 | Crameri et al. |
| 8,048,674 B2 | 11/2011 | Minshull et al. |
| 8,058,001 B2 | 11/2011 | Crameri et al. |
| 8,076,138 B2 | 12/2011 | delCardayre et al. |
| 8,108,150 B2 | 1/2012 | Mundorff et al. |
| 8,170,806 B2 | 5/2012 | Selifonov et al. |
| 8,224,580 B2 | 7/2012 | Mundorff et al. |
| 8,273,547 B2 | 9/2012 | Giver et al. |
| 8,343,764 B2 | 1/2013 | Abad et al. |
| 8,377,681 B2 | 2/2013 | delCardayre et al. |
| 8,383,346 B2 | 2/2013 | Colbeck et al. |
| 8,457,903 B1 | 6/2013 | Emig et al. |
| 8,504,498 B2 | 8/2013 | Fox |
| 8,589,085 B2 | 11/2013 | Selifonov et al. |
| 8,748,143 B2 | 6/2014 | Liang et al. |
| 8,762,066 B2 | 6/2014 | Fox |
| 8,768,871 B2 | 7/2014 | Fox |
| 9,593,326 B2 | 3/2017 | Clark et al. |
| 10,087,213 B2 * | 10/2018 | Chen ............... C07K 1/14 |
| 2004/0101937 A1 | 5/2004 | Moore et al. |
| 2006/0195947 A1 | 8/2006 | Davis et al. |
| 2006/0286646 A1 | 12/2006 | Patel et al. |
| 2008/0038803 A1 | 2/2008 | Iwasaki et al. |
| 2008/0220990 A1 | 9/2008 | Fox |
| 2009/0312196 A1 | 12/2009 | Colbeck et al. |
| 2010/0151529 A1 | 6/2010 | Zhao et al. |
| 2011/0070630 A1 | 3/2011 | Gruber et al. |
| 2011/0105483 A1 | 5/2011 | Chimmanamada et al. |
| 2015/0239852 A1 | 8/2015 | Van Summeren et al. |
| 2016/0053289 A1 | 2/2016 | Ertl |

FOREIGN PATENT DOCUMENTS

| | | |
|---|---|---|
| JP | 2010-539952 A | 12/2010 |
| JP | 2011-516053 A | 5/2011 |
| JP | 2016-521121 A | 7/2016 |
| JP | 2016-537700 A | 12/2016 |
| WO | 95/22625 A1 | 8/1995 |
| WO | 95/33836 A1 | 12/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/40450 A1 | 6/2001 |
| WO | 01/55342 A2 | 8/2001 |
| WO | 01/75767 A2 | 10/2001 |
| WO | 2004/108912 A2 | 12/2004 |
| WO | 2005/054491 A1 | 6/2005 |
| WO | 2006/074194 A2 | 7/2006 |
| WO | 2006/090814 A1 | 8/2006 |
| WO | 2008/042876 A2 | 4/2008 |
| WO | 2009/036404 A2 | 3/2009 |
| WO | 2009/152336 A1 | 12/2009 |

(56) References Cited

FOREIGN PATENT DOCUMENTS

| WO | 2011/071058 A1 | 6/2011 |
| WO | 2015/048572 A1 | 4/2015 |

OTHER PUBLICATIONS

Altschul, S.F., et al., "Gapped BLAST and PSI-BLAST: a new generation of protein database search programs," Nucleic Acids Res., 25(17):3389-3402 (1997).
Beaucage, S.L., et al., "Deoxynucleoside phosphoamidites—A new class of key intermediates for deoxypolynucleotide synthesis," Tetrahedron Letters, 22(20):1859-62 (1981).
Botstein, D., et al., "Strategies and applications of in vitro mutagenesis," Science, 229(4719):1193-1201 [1985].
Broussy, R.W., et al., "Enantioselective, Ketoreductase-Based Entry into Pharmaceutical Building Blocks: Ethanol as Tunable Nicotinamide Reductant," Org. Lett., 11(2):305-308 [2009].
Carter, P., "Site-directed mutagenesis," Biochem. J., 237:1-7 (1986).
Christians, F.C., et al., "Directed evolution of thymidine kinase for AZT phosphorylation using DNA family shuffling," Nat. Biotechnol., 17:259-264 (1999).
Crameri, A., et al., "DNA shuffling of a family of genes from diverse species accelerates directed evolution", Nature, 391:288-291 (1998).
Crameri, A., et al., "Improved green fluorescent protein by molecular evolution using DNA shuffling," Nat. Biotechnol., 14(3):315-319 (1996).
Crameri, A., et al., "Molecular evolution of an arsenate detoxification pathway by DNA shuffling," Nat. Biotechnol., 15(5):436-438 (1997).
Dale, S.J., et al., "Oligonucleotide-directed random mutagenesis using the phosphorothioate method," Methods Mol. Biol., 57:369-74 (1996).
De Boer, H.A., et al., "The tac promoter: A functional hybrid derived from the trp and lac promoters," Proc. Natl Acad. Sci. USA, 80: 21-25 (1983).
Ehrlich, S.D., "DNA cloning in Bacillus subtilis," Proc. Natl. Acad. Sci. USA, 75(3):1433-1436 [1978].
Guo, Z., et al., "3'-End-Forming Signals of Yeast mRNA," Mol. Cell. Biol., 15(11):5983-5990 [1995].
Henikoff, S., et al., "Amino acid substitution matrices from protein blocks," Proc. Natl. Acad. Sci. USA, 89:10915-10919 [1992].
Hummel, W., et al., "Dehydrogenases for the synthesis of chiral compounds," Eur. J. Biochem., 184:1-13 [1989].
Kramer, B., et al., "Different base/base mismatches are corrected with different efficiencies by the methyl-directed DNA mismatch-repair system of E. coli," Cell, 38(3):879-887 [1984].
Lathe, R., et al., "Plasmid and bacteriolphage vecotrs for excision of intact inserts," Gene, 57:193-201 [1987].
Ling, M.M., et al., "Approaches to DNA Mutagenesis: An Overview," Anal. Biochem., 254(2):157-78 [1997].
Matthes, H.W.D., et al., "Simultaneous rapid chemical synthesis of over one hundred oligonucleotides on a microscale," EMBO J., 3(4):801-05 (1984).
Minshull, J., et al., "Protein evolution by molecular breeding," Curr. Op. Chem. Biol., 3(3):284-290 (1999).
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).

Romanos, M.A., et al., "Foreign gene expression in yeast: a review," Yeast 8:423-488 [1992].
Santaniello, E., et al., "Chiral synthesis of a component of Amanita muscaria, (−)-4-hydroxypyrrolidin-2-one, and Assessment of its absolute configuration," J. Chem. Res., (S)132-133 [1984].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Villa-Komaroff, L., et al., "A bacterial clone synthesizing proinsulin," Proc. Natl Acad. Sci. USA, 75:3727-3731 (1978).
Wells, J.A., et al., "Cassette mutagenesis: an efficient method for generation of multiple mutations at defined sites," Gene, 34:315-323 (1985).
Zhang, J-H., et al., "Directed evolution of a fucosidase from a galactosidase by DNA shuffling and screening," Proc. Nat. Acad. Sci., U.S.A., 94:4504-4509 (1997).
Zhou, B., et al., "Stereochemical control of yeast reductions. 1. Asymmetric synthesis of L-Carnitine," J. Am. Chem. Soc., 105:5925-5926 [1983].
Genbank Accession No. 1NXQ_A dated Sep. 24, 2008.
Genbank Accession No. AAP94029.1 dated Apr. 1, 2004.
Genbank Accession No. AF160799 dated Dec. 9, 1999.
Genbank Accession No. BAA24528.1 dated Jan. 28, 1998.
Genbank Accession No. JC7338 dated Jun. 3, 2002.
UniProtKB/Swiss-Prot No. P14941 dated May 10, 2017.
Kita, K., et al., "Cloning, Overexpression, and Mutagenesis of theSporobolomyces salmonicolor AKU4429 Gene Encoding a New Aldehyde Reductase, Which Catalyzes the Stereoselective Reduction of Ethyl 4-Chloro-3-Oxobutanoate to Ethyl (S)-4-Chloro-3-Hydroxybutanoate," Applied and Environmental Microbiology, 65(12):5207-5211 [1999].
Ma, S.K., et al., "A green-by-design biocatalytic process for atorvastatin intermediate," Green Chemistry, 12(1):81-86 [2010].
Zheng, G., et al., "New opportunities for biocatalysis: driving the synthesis of chiral chemicals," Current Opinion in Biotechnology, 22(6):784-792 [2011].
Broun, P., et al., "Catalytic Plasticity of Fatty Acid Modification Enzymes Underlying Chemical Diversity of Plant Lipids," Science, 282:1315-1317 [1998].
Devos, D., et al., "Practical Limits of Function Prediction," Proteins: Structure, Function, and Genetics, 41:98-107 [2000].
Seffernick, J.L., et al., "Melamine Deaminase and Atrazine Chlorohydrolase: 98 Percent Identical but Functionally Different," J. Bacteriology, 183(8):2405-2410 [2001].
Whisstock, J.C., et al., "Prediction of protein function from protein sequence and structure," Quarterly Reviews of Biophysics, 36(3):307-340 [2003].
Witkowski, A., et al., "Conversion of a beta-Ketoacyl Synthase to a Malonyl Decarboxylase by Replacement of the Active-Site Cysteine with Glutamine," Biochemistry, 38(36):11643-11650 [1999].
UniProtKT/TREMBL Accession No. H8WVM2_CAN09 dated May 16, 2012.

\* cited by examiner

KETOREDUCTASE POLYPEPTIDES AND POLYNUCLEOTIDES

The present application is a Continuation of co-pending of U.S. patent application Ser. No. 17/239,953, filed Apr. 26, 2021, which is a Divisional of U.S. patent application Ser. No. 16/605,576, filed Oct. 16, 2019, now U.S. Pat. No. 11,021,729, a national stage application filed under 35 USC § 371 and claims priority to international application to PCT International Application No. PCT/US2018/027450, filed Apr. 13, 2018, which claims priority to U.S. Prov. Pat. Appln. Ser. No. 62/491,161, filed Apr. 27, 2017, all of which are hereby incorporated by reference, in their entireties and for all purposes.

REFERENCE TO SEQUENCE LISTING, TABLE OR COMPUTER PROGRAM

The Sequence Listing concurrently submitted herewith under 37 C.F.R. § 1.821 in a computer readable form (CRF) as file name CX2-166WO1UDC1 ST26.xml is herein incorporated by reference. The electronic copy of the Sequence Listing was created on Jul. 14, 2023, with a file size of 500,455 bytes.

FIELD OF THE INVENTION

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

BACKGROUND

Enzymes belonging to the ketoreductase (KRED) or carbonyl reductase class (EC1.1.1.184) are useful for the synthesis of optically active alcohols from the corresponding prochiral ketone substrate and by stereoselective reduction of corresponding racemic aldehyde substrates. KREDs typically convert ketone and aldehyde substrates to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state), but most often not both.

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone and aldehyde reductions or for biocatalytic alcohol oxidation, or by use of purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase, phosphite dehydrogenase etc. can be used in conjunction with the ketoreductase. It is desirable to identify other ketoreductase enzymes that can be used to carryout conversion of various keto substrates to corresponding chiral alcohol products or conversion of various alcohol substrates to corresponding ketone products.

SUMMARY OF THE INVENTION

The present invention provides engineered ketoreductase and phosphite dehydrogenase enzymes having improved properties as compared to a naturally occurring wild-type ketoreductase and phosphite dehydrogenase enzymes, as well as polynucleotides encoding the engineered ketoreductase and phosphite dehydrogenase enzymes, host cells capable of expressing the engineered ketoreductase and phosphite dehydrogenase enzymes, and methods of using the engineered ketoreductase and phosphite dehydrogenase enzymes to synthesize a chiral catalyst used in the synthesis of antiviral compounds, such as nucleoside inhibitors. The present invention further provides methods of using the engineered enzymes to deracemize a chiral alcohol in a one-pot, multi-enzyme system.

In addition, the present invention provides engineered phosphite dehydrogenase enzymes having improved properties as compared to a naturally occurring wild-type phosphite dehydrogenase enzyme, as well as polynucleotides encoding the engineered phosphite dehydrogenase enzymes, host cells capable of expressing the engineered phosphite dehydrogenase enzymes, and methods of using the engineered phosphite dehydrogenase enzymes to deracemize a chiral alcohol in a one-pot, multi-enzyme system.

The present invention provides engineered ketoreductase ("KRED") enzymes that are capable of stereoselectively deracemizing a racemic alcohol substrate to an optically pure alcohol product in a one-pot, multi-enzyme system, and having an improved property when compared with the naturally-occurring, wild-type KRED enzyme obtained from *Candida parapsilosis* (SEQ ID NO:2), wild-type KRED enzyme obtained from *Sporidiobolus salmonicolor* (SEQ ID NO: 112), or when compared with other engineered ketoreductase enzymes. In addition, the present invention provides engineered phosphite dehydrogenase ("PDH") enzymes capable of preferentially recycling NADPH in the same one-pot, multi-enzyme system.

In some further embodiments, the engineered enzymes have one or more improved properties in addition to altered enzymatic activity. For example, in some embodiments, the engineered ketoreductase polypeptides have increased stereoselectivity, as compared to the wild-type ketoreductase enzyme for reducing the substrate to the product and/or preferentially oxidize the (S) enantiomer. Improvements in enzyme properties include, but are not limited to increases in thermostability, solvent stability, and/or reduced product inhibition.

The present invention provides engineered ketoreductase variants having at least 85%, 90%, 91%, 92%, 93%, 94%, 95%, 96%, 97%, 98%, 99% or more sequence identity to SEQ ID NO: 2, 112, 124, and/or 138.

The present invention also provides engineered ketoreductase variants have at least 85%, 90%, 91%, 92%, 93%, 94%, 95%, 96%, 97%, 98%, 99% or more sequence identity to SEQ ID NO:2, and at least one substitution or substitution set at one or more positions selected from positions 37, 37/211, 37/211/229, 37/229, 45, 52, 52/57/110/272/296, 52/57/272, 52/57/272/274/279/296, 52/57/272/279/296, 55/57/276, 56, 57, 57/104/114, 57/104/114/229, 57/286, 79/83/275/276, 83, 83/275/276, 83/276, 104, 110, 114, 138/146/258/289, 211, 211/229, 228, 229, 263, 268, 272, 274, 275/276, 276, 279, and 309, wherein the positions are numbered with reference to SEQ ID NO:2. In some additional embodiments, the engineered ketoreductase variants comprise at least one substitution or substitution set selected from 37R, 37R/21 1R, 37R/211R/229R, 37R/229R, 45R, 52D, 52D/57L/272H, 52S, 52S/57L/110T/272H/296F, 52S/57L/272H/279H/296F, 52S/57L/272H/274V/279H/296F, 55F/57A/276M, 56L, 57I, 57I/104G/114H, 57L, 57L/104G/114H/229R, 57X/286X, 79T/83S/275N/276M, 83I, 83S/275N/276M, 83S/276M, 104G, 110T, 114H/K/M, 138V/146S/258V/289S, 211R, 211R/229R, 228S, 229R, 263H/Y, 268M/W, 272H/I/L/P/Q/S/T/V/W, 274I/V, 275N/276M, 276/M, 279H/Q/R and 309F, wherein the positions are numbered with reference to SEQ ID NO:2. In some further embodiments, the engineered ketoreductase variants comprise at least one substitution or substitution set selected from K37R, K37R/K211R, K37R/K211R/G229R, K37R/G229R, H45R, Y52D, Y52D/C57L/G272H, Y52S, Y52S/C57L/K110T/G272H/L296F, Y52S/C57L/G272H/I279H/L296F, Y52S/C57L/G272H/L274V/I279H/L296F, L55F/C57A/L276M, D56L, C57I, C57I/A104G/G114H, C57L, C57L/A104G/G114H/G229R, C57X/W286X, 179T/V83S/A275N/L276M, V83I, V83S/A275N/L276M, V83S/L276M, A104G, K110T, GI14H/K/M, S138V/A146S/M258V/T289S, K21 1R, K211R/G229R, P228S, G229R, G263H/Y, S268M/W, G272H/I/L/P/Q/S/T/V/W, L274I/V, A275N/L276M, L276F/M, I279H/Q/R, and R309F, wherein the positions are numbered with reference to SEQ ID NO:2.

The present invention also provides engineered ketoreductase variants having at least 85%, 90%, 91%, 92%, 93%, 94%, 95%, 96%, 97%, 98%, 99% or more sequence identity to SEQ ID NO: 112, and at least one substitution or substitution set at one or more positions selected from positions 24/106/136/220/258/260/314/315, 24/106/214/250/258/260/314/315, 24/220/314/315, 122/159/316/318, 135, 139/207, 159/251/272/277/316/318/330, and 207, wherein the positions are numbered with reference to SEQ ID NO: 112. In some embodiments, the engineered ketoreductase variants comprise at least one substitution or substitution set selected from 24I/106P/136A/220G/258V/260A/314R/315A, 24I/106P/214L/250V/258V/260A/314R/315A, 24I/220G/314R/315A, 122E/159V/316E/318L, 135F, 139V/207S, 159V/251Q/272F/277P/316E/318L/330L, and 207G, wherein the positions are numbered with reference to SEQ ID NO: 112. In some additional embodiments, the engineered ketoreductase variants comprise at least one substitution or substitution set selected from V24I/T106P/S136A/S220G/L258V/C260A/P314R/S315A, V24I/T106P/F214L/A250V/L258V/C260A/P314R/S315A, V24I/S220G/P314R/S315A, T122E/I159V/L316E/I318L, V135F, I139V/N207S, I159V/V251Q/Y272F/T277P/L316E/I318L/I330L, and N207G, wherein the positions are numbered with reference to SEQ ID NO: 112.

The present invention also provides engineered ketoreductase variants having at least 85%, 90%, 91%, 92%, 93%, 94%, 95%, 96%, 97%, 98%, 99% or more sequence identity to SEQ ID NO: 124, and at least one substitution set selected from positions 2/101/179/182/228/238/282, 3/95, 3/95/228/314, 24/95/228, 95, 95/135/139/207, and 159/228/309/330, wherein the positions are numbered with reference to SEQ ID NO: 124. In some embodiments, the engineered ketoreductase variants comprise at least one substitution or substitution set selected from 2T/101P/179L/182M/228R/238L/282E, 3Y/95T, 3Y/95T/228T/314R, 24I/95T/228T, 95T, 95T/135F/139V/207N, and 159V/228L/309Q/330L, wherein the positions are numbered with reference to SEQ ID NO: 124. In some further embodiments, the engineered ketoreductase variants comprise at least one substitution or substitution set selected from A2T/Y101P/A179L/T182M/M228R/A238L/T282E, K3Y/V95T, K3Y/V95T/M228T/P314R, V24I/V95T/M228T, V95T, V95T/V135F/I139V/G207N, and I159V/M228L/K309Q/I330L, wherein the positions are numbered with reference to SEQ ID NO: 124.

The present invention also provides engineered ketoreductase variants having at least 85%, 90%, 91%, 92%, 93%, 94%, 95%, 96%, 97%, 98%, 99% or more sequence identity to SEQ ID NO:138, and at least one substitution or substitution set at one or more positions selected from positions 19, 24/43/47/49/67/68/70/91/220, 24/68/91/218/220, 67, 72, 74/75/78/108, 75/78/99/108/215/224, 78/107, 95, 96, and 114, wherein the positions are numbered with reference to SEQ ID NO:138. In some embodiments, the engineered ketoreductase variants comprise at least one substitution or substitution set selected from 19S, 24I/43V/47E/49N/67V/68E/70P/91V/220G, 24I/68E/91V/218N/220G, 67W, 72Q, 74A/75E/78F/108V, 75E/78F/99P/108V/215S/224A, 78F/107G, 95C, 96G, and 114V, wherein the positions are numbered with reference to SEQ ID NO: 138. In some further embodiments, the engineered ketoreductase variants comprise at least one substitution or substitution set selected from G19S, V24I/A43V/S47E/L49N/A67V/V68E/E70P/I91V/S220G, V24I/V68E/I91V/T218N/S220G, A67W, M72Q, K74A/Q75E/Y78F/A108V, Q75E/Y78F/N99P/A108V/D215S/S224A, Y78F/P107G, T95C, S96G, and N114V, wherein the positions are numbered with reference to SEQ ID NO:138.

The present invention also provides engineered ketoreductase variants comprising polypeptide sequences comprising sequences having at least 90% sequence identity to SEQ ID NO:2, 112, 124, and/or 138. In some embodiments, the engineered ketoreductase variants comprise polypeptide sequences comprising sequences having at least 95% sequence identity to SEQ ID NO:2, 112, 124, and/or 138. In some further embodiments, the engineered ketoreductase variants comprise polypeptide sequences set forth in SEQ ID NO:2, 112, 124, or 138. In some additional embodiments, the engineered ketoreductase variants comprise polypeptide sequences encoding variants provided in Table 5.1, 6.1, 7.1, and/or 8.1. In some further embodiments, the engineered ketoreductase variants comprise polypeptide sequences selected from the even-numbered sequences set forth in SEQ ID NOS: 4 to 170.

The present invention also provides engineered polynucleotide sequences encoding the engineered ketoreductase variants provided herein. In some embodiments, the engineered polynucleotide sequence comprises a polynucleotide sequence that is at least 85%, 90%, 91%, 92%, 93%, 94%, 95%, 96%, 97%, 98%, 99% or more identical to a sequence selected from the odd-numbered sequences set forth in SEQ ID NOS: 3 to 169. The present invention also provides vectors comprising the engineered polynucleotide sequences encoding the engineered ketoreductase variants provided herein. In some embodiments, the vectors further comprise at least one control sequence.

The present invention also provides host cells comprising the vectors comprising polynucleotides encoding the engineered ketoreductase variants provided herein.

The present invention also provides methods producing the engineered ketoreductase variants provided herein, comprising culturing the host cells provided herein under conditions that the engineered ketoreductase variant is produced by the host cell. In some embodiments, the methods further comprise the step of recovering the engineered ketoreductase variant produced by the host cell.

The present invention also provides immobilized engineered ketoreductase variants.

The present invention further provides compositions comprising at least one engineered ketoreductase variant provided herein. In some embodiments, the compositions comprise at least one immobilized engineered ketodreductase variant provided herein.

The present invention also provides engineered phosphite dehydrogenase variants having at least 85%, 90%, 91%, 92%, 93%, 94%, 95%, 96%, 97%, 98%, 99% or more sequence identity to SEQ ID NO: 172 and/or 208.

The present invention also provides engineered phosphite dehydrogenase variants having at least 85%, 90%, 91%, 92%, 93%, 94%, 95%, 96%, 97%, 98%, 99% or more sequence identity to SEQ ID NO: 172, and at least one substitution or substitution set at one or more positions selected from positions 10/73/78/137/323/325, 10/73/78/233/323, 10/73/137, 13/41/63/132/193/195, 18/44/119/124/132/137/145/158/175/177/293/317/323, 18/44/119/124/132/137/145/158/177/293/323, 18/44/119/124/132/137/145/293/323/334/336, 32/44/132/137/145/186/233/293/323/336, 41/44/88/193/195, 44/69/120/132/137/145/175/195/293/323, 44/113/132/145, 44/119/132/137/145/158/175/177/293/317/323, 44/132/135/136/137/145/293, 44/132/136/137/145/293, 44/132/137/145/233/308/323, 44/132/137/145/293/323, 44/132/145, 44/132/145/195/293/323, 137/233/303/323, and 266, wherein the positions are numbered with reference to SEQ ID NO: 172. In some embodiments, the engineered phosphite dehydrogenase variants comprise at least one substitution or substitution set selected from 10K/73A/78Y/137Q/323D/325A, 10K/73A/78Y/233I/323D, 10K/73A/137Q, 13D/41A/63A/132Q/193S/195E, 18M/44A/119F/124E/132Q/137I/145G/158K/175S/177T/293L/317R/323D, 18M/44A/119F/124E/132Q/137I/145G/158K/177T/293L/323D, 18M/44A/119F/124E/132Q/137I/145G/293L/323D/334K/336R, 32V/44A/132Q/137I/145G/186T/233I/293L/323D/336S, 41A/44A/88R/193S/195E, 44A/69K/120V/132Q/137I/145G/175T/195E/293L/323D, 44A/113S/132Q/145G, 44A/119F/132Q/137I/145G/158K/175S/177T/293L/317R/323D, 44A/132Q/135A/136D/137I/145G/293L, 44A/132Q/136D/137Q/145G/293L, 44A/132Q/137I/145G/233I/308V/323D, 44A/132Q/137I/145G/293L/323D, 44A/132Q/145G, 44A/132Q/145G/195E/293L/323D, 137Q/233I/303A/323D, and 266S/V/W, wherein the positions are numbered with reference to SEQ ID NO: 172. In some further embodiments, the engineered phosphite dehydrogenase variants comprise at least one substitution or substitution set selected from R10K/C73A/F78Y/R137Q/N323D/V325A, R10K/C73A/F78Y/V233I/N323D, R10K/C73A/R137Q, E13D/R41A/Q63A/R132Q/A193S/S195E, L18M/R44A/L 119F/A124E/R132Q/R137I/N145G/L158K/A175S/K177T/I293L/A317R/N323D, L18M/R44A/L 119F/A124E/R132Q/R137I/N145G/L158K/K177T/I293L/N323D, L18M/R44A/L 119F/A124E/R132Q/R137I/N145G/I293L/N323D/A334K/C336R, S32V/R44A/R132Q/R137I/N145G/R186T/V233I/I293L/N323D/C336S, R41A/R44A/A88R/A193S/S195E, R44A/R69K/R120V/R132Q/R137I/N145G/A175T/S195E/I293L/N323D, R44A/V113S/R132Q/N145G, R44A/L 119F/R132Q/R137I/N145G/L158K/A175S/K177T/I293L/A317R/N323D, R44A/R132Q/Q135A/P136D/R137I/N145G/I293L, R44A/R132Q/P136D/R137Q/N145G/I293L, R44A/R132Q/R137I/N145G/V233I/A308V/N323D, R44A/R132Q/R137I/N145G/I293L/N323D, R44A/R132Q/N145G, R44A/R132Q/N145G/S195E/I293L/N323D, R137Q/V233I/E303A/N323D, and E266S/V/W, wherein the positions are numbered with reference to SEQ ID NO: 172.

The present invention also provides engineered phosphite dehydrogenase variants having at least 85%, 90%, 91%, 92%, 93%, 94%, 95%, 96%, 97%, 98%, 99% or more sequence identity to SEQ ID NO:208, and at least one substitution or substitution set at one or more positions selected from positions 32/59/124/177/191/327, 78/150/198/327/328, 83/266, 95/211/213/322, 104, 178/194/211/213/322, 206, 211/213/322, 215, 262, 266, and 323, wherein the positions are numbered with reference to SEQ ID NO:208. In some embodiments, the engineered phosphite dehydrogenase variants comprise at least one substitution or substitution set selected from 32V/59M/124E/177S/191H/327D, 78Y/150I/198L/327S/328P, 83A/266A, 95I/211A/213Q/322M, 104F/L, 178P/194L/211A/213Q/322Q, 206N, 211A/213Q/322Q, 215P, 262D/P, 266S, and 323N, wherein the positions are numbered with reference to SEQ ID NO:208. In some further embodiments, the engineered phosphite dehydrogenase variants comprise at least one substitution or substitution set selected from S32V/A59M/A124E/T177S/Q191H/R327D, F78Y/F150I/F198L/R327S/L328P, V83A/E266A, F95I/N211A/D213Q/I322M, T104F/L, A178P/C194L/N211A/D213Q/I322Q, L206N, N211A/D213Q/I322Q, L215P, V262D/P, E266S, and D323N, wherein the positions are numbered with reference to SEQ ID NO:208.

The present invention also provides engineered phosphite dehydrogenase variants comprising a polypeptide sequence comprising a sequence having at least 90% sequence identity to SEQ ID NO: 172 and/or 208. In some embodiments, the engineered phosphite dehydrogenase variants comprise polypeptide sequences comprising sequences having at least 95% sequence identity to SEQ ID NO: 172 and/or 208. In some further embodiments, the engineered phosphite dehydrogenase variants comprise polypeptide sequences set forth in SEQ ID NO: 172 or 208. In some additional embodiments, the engineered phosphite dehydrogenase variants comprise polypeptide sequences encoding variants provided in Table 9.1, 10.1, and/or 11.1. In yet some additional embodiments, the engineered phosphite dehydrogenase variants comprise polypeptide sequences selected from the even-numbered sequences set from in SEQ ID NOS: 174 to 260.

The present invention also provides immobilized engineered phosphite dehydrogenase variants. In some embodiments, the present invention provides a mixture of at least one immobilized engineered ketoreductase variant provided herein and at least one engineered phosphite dehydrogenase variant provided herein.

The present invention also provides compositions comprising at least one phosphite dehydrogenase variant provided herein. In some embodiments, the present invention further provides compositions comprising mixtures of at least one engineered ketoreductase variant provided herein and at least one engineered phosphite dehydrogenase provided herein.

The present invention also provides engineered polynucleotide sequences encoding the engineered phosphite dehydrogenase variants provided herein. In some embodiments, the engineered polynucleotide sequences comprise polynucleotide sequences that are at least 85%, 90%, 91%, 92%, 93%, 94%, 95%, 96%, 97%, 98%, 99% or more identical to a sequence selected from the odd-numbered sequences set forth in SEQ ID NOS: 3 to 169.

The present invention also provides vectors comprising the engineered polynucleotide sequence encoding the engineered phosphite dehydrogenase variants provided herein. In some embodiments, the vectors further comprise at least one control sequence. In yet some further embodiments, the vectors comprise at least one engineered polynucleotide sequence encoding an engineered phosphite dehydrogenase variant provided herein and at least one engineered polynucleotide sequence encoding an engineered ketoreductase variant provided herein. The present invention also provides host cells comprising the vectors provided herein.

The present invention also provides methods for producing the engineered phosphite dehydrogenase variants provided herein, comprising culturing the host cell comprising a vector comprising at least one engineered polynucleotide sequence encoding at least one engineered phosphite dehydrogenase of the present invention, under conditions that the engineered phosphite dehydrogenase variant is produced by the host cell. In some embodiments, the host cells comprise vectors comprising polynucleotide sequences comprising at least one engineered ketoreductase and at least one engineered phosphite dehydrogenase provided herein. In some additional embodiments, the host cells comprise at least one ketoreductase not provided herein, but comprise at least one engineered phosphite dehydrogenase variant provided herein. In some further embodiments, the host cells comprise at least on phosphite dehydrogenase not provided herein, but comprise at least one engineered ketoreductase variant provided herein. In some embodiments, the methods further comprise the step of recovering the engineered phosphite dehydrogenase variant produced by the host cell. In embodiments with host cells that produce at least one ketoreductase and at least one phosphite dehydrogenase, some methods further comprise the step of recovering the ketoreductase and/or phosphite dehydrogenase produced by the host cells.

The present invention also provides methods deracemizing chiral alcohols comprising providing at least one engineered ketoreductase variant provided herein, providing at least one engineered phosphite dehydrogenase variant provided herein, at least one chiral alcohol, and at least one co-factor, under conditions such that the chiral alcohol is deracemized. In some embodiments, the methods are conducted in a one pot reaction, while in some alternative embodiments, multiple reaction vessels are used.

DESCRIPTION OF THE INVENTION

Figure 1:
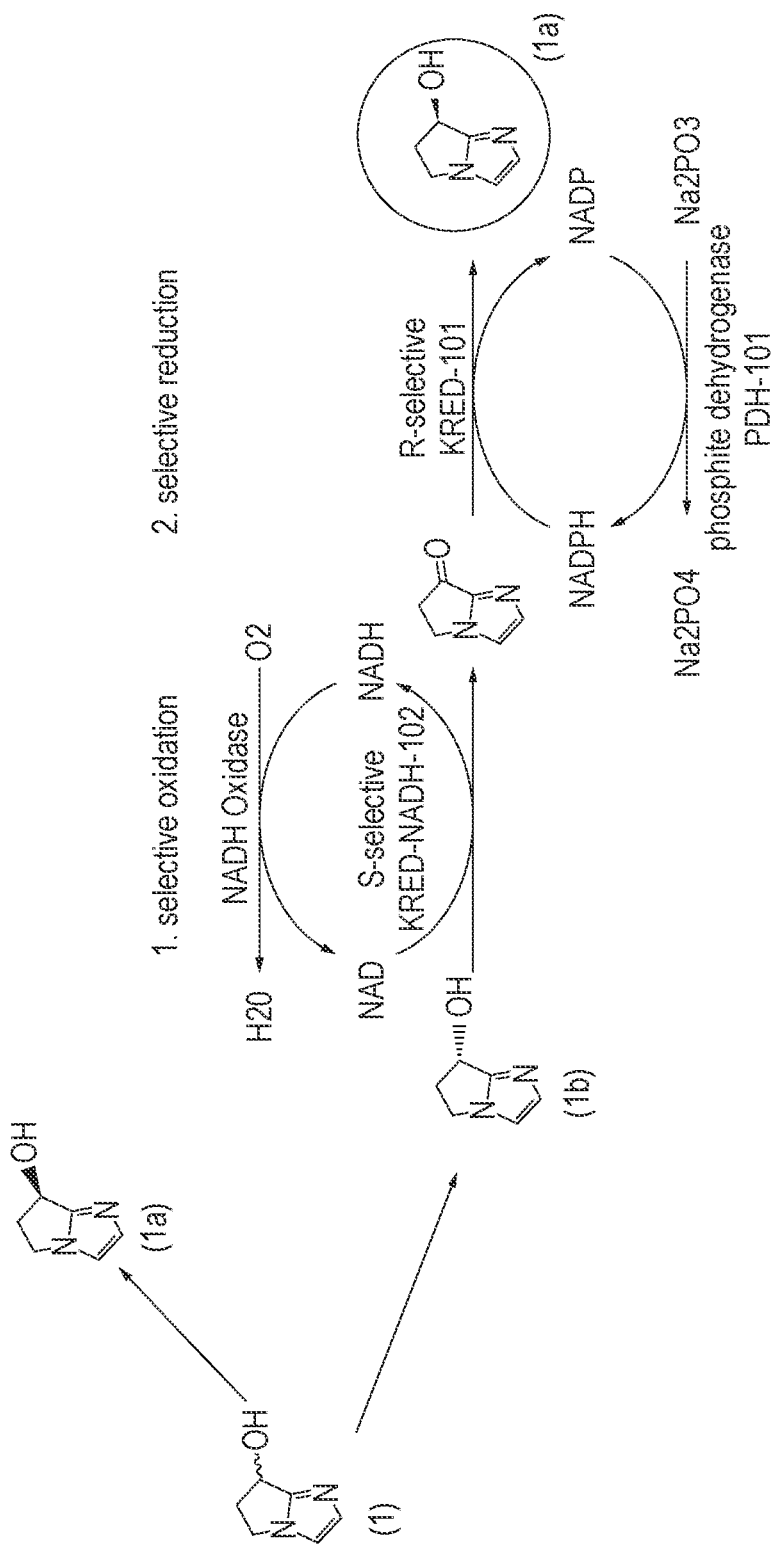
FIG. 1 provides the reaction scheme addressed by the present invention.

The present invention provides engineered ketoreductase enzymes and engineered phosphite dehydrogenase enzymes having improved properties as compared to a naturally occurring wild-type ketoreductase and phosphite dehydrogenase enzyme, as well as polynucleotides encoding the engineered ketoreductase and engineered phosphite dehydrogenase enzymes, host cells capable of expressing the engineered ketoreductase and engineered phosphite dehydrogenase enzymes, and methods of using the engineered ketoreductase and engineered phosphite dehydrogenase enzymes to deracemize a racemic alcohol in a one-pot, multi-enzyme system.

Definitions

In reference to the present invention, the technical and scientific terms used in the descriptions herein will have the meanings commonly understood by one of ordinary skill in the art, unless specifically defined otherwise. Accordingly, the following terms are intended to have the following meanings. All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation and amino acid sequences are written left to right in amino to carboxy orientation, respectively.

The headings provided herein are not limitations of the various aspects or embodiments of the invention that can be had by reference to the specification as a whole. Accordingly, the terms defined below are more fully defined by reference to the specification as a whole.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively deracemizing an alcohol of formula (I) to the corresponding product of formula (II) in an one-pot, multi-enzyme system, as shown in Scheme 1 (See, FIG. 1).

Phosphite dehydrogenase and "PDH" are used interchangeably herein to refer to a polypeptide having an enzymatic capability of regenerating NADPH co-factor.

As used herein, the term "one-pot reaction" refers to the production of a product from a starting material using multiple enzymes (i.e., KREDs and PDHs) in one reaction vessel.

As used herein, the terms "protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

As used herein, "polynucleotide" and "nucleic acid" refer to two or more nucleosides that are covalently linked together. The polynucleotide may be wholly comprised of ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine, and cytosine), it may include one or more modified and/or synthetic nucleobases (e.g., inosine, xanthine, hypoxanthine, etc.). Preferably, such modified or synthetic nucleobases will be encoding nucleobases.

As used herein, "coding sequence" refers to that portion of a nucleic acid (e.g., a gene) that encodes an amino acid sequence of a protein.

As used herein, "naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

As used herein, "non-naturally occurring" or "engineered" or "recombinant" when used in the present invention with reference to (e.g., a cell, nucleic acid, or polypeptide), refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

As used herein, "percentage of sequence identity," "percent identity," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (See e.g., Altschul et al., J. Mol. Biol. 215: 403-410 [1990]; and Altschul et al., Nucleic Acids Res. 3389-3402 [1977]). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc Natl Acad Sci USA 89:10915 [1989]).

Numerous other algorithms are available and known in the art that function similarly to BLAST in providing percent identity for two sequences. Optimal alignment of sequences for comparison can be conducted using any suitable method known in the art (e.g., by the local homology algorithm of Smith and Waterman, Adv. Appl. Math. 2:482 [1981]; by the homology alignment algorithm of Needleman and Wunsch, J. Mol. Biol. 48:443 [1970]; by the search for similarity method of Pearson and Lipman, Proc. Natl. Acad. Sci. USA 85:2444 [1988]; and/or by computerized implementations of these algorithms [GAP, BESTFIT, FASTA, and TFASTA in the GCG Wisconsin Software Package]), or by visual inspection, using methods commonly known in the art. Additionally, determination of sequence alignment and percent sequence identity can employ the BESTFIT or GAP programs in the GCG Wisconsin Software package (Accelrys, Madison WI), using the default parameters provided.

As used herein, "reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

As used herein, "comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn" as further described below, is to be construed as referring to "a residue corresponding to", unless specifically denoted otherwise. Thus, for example, "X94" refers to any amino acid at position 94 in a polypeptide sequence.

As used herein, "stereoselectivity" refers to the preferential formation in a chemical or enzymatic reaction of one stereoisomer over another stereoisomer or another set of stereoisomers. Stereoselectivity can be partial, where the formation of a stereoisomer is favored over another, or it may be complete where only one stereoisomer is formed. When the stereoisomers are enantiomers, the stereoselectivity is referred to as enantioselectivity, the fraction (typically reported as a percentage) of one enantiomer in the sum of both enantiomers. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess. It is also to be understood that stereoselectivity is not limited to single stereoisomers and can be described for sets of stereoisomers.

As used herein, "highly stereoselective" refers to a chemical or enzymatic reaction that is capable of converting a substrate to its corresponding chiral alcohol product, with at least about 75% stereomeric excess.

As used herein, "increased enzymatic activity" and "increased activity" refer to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of Km, Vmax or kcat, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

As used herein, "conversion" refers to the enzymatic transformation of a substrate to the corresponding product.

As used herein "percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

As used herein, "thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

As used herein, "solvent stable" refers to the ability of a polypeptide to maintain similar activity (e.g., more than e.g., 60% to 80%) after exposure to varying concentrations (e.g., 5-99%) of solvent compared to the untreated enzyme.

As used herein, "amino acid difference" or "residue difference" refers to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X40 as compared to SEQ ID NO:2" refers to a difference of the amino acid residue at the polypeptide position corresponding to position 40 of SEQ ID NO:2. Thus, if the reference polypeptide of SEQ ID NO:2 has a histidine at position 40, then a "residue difference at position X40 as compared to SEQ ID NO:2" refers to an amino acid substitution of any residue other than histidine at the position of the polypeptide corresponding to position 40 of SEQ ID NO:2. In most instances herein, the specific amino acid residue difference at a position is indicated as "XnY" where "Xn" specified the corresponding position as described above, and "Y" is the single letter identifier of the amino acid found in the engineered polypeptide (i.e., the different residue than in the reference polypeptide). In some instances, the present invention also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present invention can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X192A/G). The present invention includes engineered polypeptide sequences comprising one or more amino acid differences that include either/or both conservative and non-conservative amino acid substitutions. The amino acid sequences of the specific recombinant carbonic anhydrase polypeptides included in the Sequence Listing of the present invention include an initiating methionine (M) residue (i.e., M represents residue position 1). The skilled artisan, however, understands that this initiating methionine residue can be removed by biological processing machinery, such as in a host cell or in vitro translation system, to generate a mature protein lacking the initiating methionine residue, but otherwise retaining the enzyme's properties. Consequently, the term "amino acid residue difference relative to SEQ ID NO:2 at position Xn" as used herein may refer to position "Xn" or to the corresponding position (e.g., position (X−1)n) in a reference sequence that has been processed so as to lack the starting methionine.

As used herein, the phrase "conservative amino acid substitutions" refers to the interchangeability of residues having similar side chains, and thus typically involves substitution of the amino acid in the polypeptide with amino acids within the same or similar defined class of amino acids. By way of example and not limitation, in some embodiments, an amino acid with an aliphatic side chain is substituted with another aliphatic amino acid (e.g., alanine, valine, leucine, and isoleucine); an amino acid with a hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and/or a hydrophobic or hydrophilic amino acid is replaced with another hydrophobic or hydrophilic amino acid, respectively. Exemplary conservative substitutions are provided in Table 1.

TABLE 1

Exemplary Conservative Amino Acid Substitutions

| Residue | Possible Conservative Substitutions |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | Non-polar |

As used herein, the phrase "non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

As used herein, "deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

As used herein, "insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to engineered ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The term "amino acid substitution set" or "substitution set" refers to a group of amino acid substitutions in a polypeptide sequence, as compared to a reference sequence. A substitution set can have 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant KREDs listed in the Tables provided in the Examples.

As used herein, "fragment" refers to a polypeptide that has an amino-terminal and/or carboxy-terminal deletion, but where the remaining amino acid sequence is identical to the corresponding positions in the sequence. Fragments can typically have about 80%, about 90%, about 95%, about 98%, or about 99% of the full-length ketoreductase polypeptide, for example the polypeptide of SEQ ID NO:4. In some embodiments, the fragment is "biologically active" (i.e., it exhibits the same enzymatic activity as the full-length sequence).

As used herein, "isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present invention can be an isolated polypeptide.

As used herein, "substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 91% or more, about 92% or more, about 93% or more, about 94% or more, about 95% or more, about 96% or more, about 97% or more, about 98% or more, or about 99% of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector). In some embodiments, "heterologous polynucleotide" refers to any polynucleotide that is introduced into a host cell by laboratory techniques, and includes polynucleotides that are removed from a host cell, subjected to laboratory manipulation, and then reintroduced into a host cell.

As used herein, "codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

As used herein, "control sequence" is defined herein to include all components, which are necessary or advantageous for the expression of a polynucleotide and/or polypeptide of the present invention. Each control sequence may be native or foreign to the polynucleotide of interest. Such control sequences include, but are not limited to, a leader, polyadenylation sequence, propeptide sequence, promoter, signal peptide sequence, and transcription terminator.

As used herein, "operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

As used herein, the phrases "cofactor regeneration system" and "cofactor recycling system" refer to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

As used herein, "suitable reaction conditions" refer to those conditions in the biocatalytic reaction solution (e.g., ranges of enzyme loading, substrate loading, cofactor loading, temperature, pH, buffers, co-solvents, etc.) under which ketoreductase polypeptides of the present invention are capable of stereoselectively deracemizing a substrate compound to a product compound. Exemplary "suitable reaction conditions" are provided in the present invention and illustrated by the Examples.

As used herein, "loading," such as in "compound loading," "enzyme loading," or "cofactor loading" refers to the concentration or amount of a component in a reaction mixture at the start of the reaction.

As used herein, "substrate" in the context of a biocatalyst mediated process refers to the compound or molecule acted on by the biocatalyst. For example, an exemplary substrate for the ketoreductase biocatalyst in the process disclosed herein is compound (1).

As used herein "product" in the context of a biocatalyst mediated process refers to the compound or molecule resulting from the action of the biocatalyst.

As used herein, "equilibration" as used herein refers to the process resulting in a steady state concentration of chemical species in a chemical or enzymatic reaction (e.g., interconversion of two species A and B), including interconversion of stereoisomers, as determined by the forward rate constant and the reverse rate constant of the chemical or enzymatic reaction.

As used herein, "oxo" refers to =O.

As used herein, "oxy" refers to a divalent group —O—, which may have various substituents to form different oxy groups, including ethers and esters.

As used herein, "carboxy" refers to —COOH.

As used herein, "carbonyl" refers to —C(O)—, which may have a variety of substituents to form different carbonyl groups including acids, acid halides, aldehydes, amides, esters, and ketones.

As used herein, "hydroxy" refers to —OH.

As used herein, "optional" and "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included.

As used herein, "optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

Engineered Enzyme Polypeptides

Ketoreductase (KRED) or carbonyl reductase biocatalysts (EC 1.1.1.184) are useful for the synthesis of alcohols from aldehydes and ketones, and optically active secondary alcohols from the corresponding prostereoisomeric ketone substrates. KREDs may also catalyze the reverse reaction, (i.e., oxidation of an alcohol substrate to the corresponding aldehydes/ketone product). The reduction of aldehydes and ketones and the oxidation of alcohols by KREDs uses a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD+ and NADP+ serve as electron acceptors.

KREDs can be found in a wide range of bacteria and yeasts, as known in the art (See e.g., Hummel and Kula Eur. J. Biochem., 184:1-13 [1989]). Numerous KRED genes and enzyme sequences have been reported, including those of *Candida magnoliae* (Genbank Acc. No. JC7338; GI: 11360538); *Candida parapsilosis* (Genbank Acc. No. BAA24528.1; GI:2815409), *Sporobolomyces salmonicolor* (Genbank Acc. No. AF160799; GI:6539734), *Lactobacillus kefir* (Genbank Acc. No. AAP94029.1; GI: 33112056), *Lactobacillus brevis* (Genbank Acc. No. 1NXQ_A; GI: 30749782), and *Thermoanaerobium brockii* (Genbank Acc. No. P14941; GI: 1771790).

The stereoselectivity of ketoreductases have been applied to the preparation of important pharmaceutical building blocks (See e.g., Broussy et al., Org. Lett., 11:305-308 [2009]). Specific applications of naturally occurring or engineered KREDs in biocatalytic processes to generate useful chemical compounds have been demonstrated for reduction of 4-chloroacetoacetate esters (See e.g,. Zhou, J. Am. Chem. Soc.,105:5925-5926 [1983]; Santaniello, J. Chem. Res., (S)132-133 [1984]; U.S. Pat. Nos. 5,559,030, 5,700,670, 5,891,685), reduction of dioxocarboxylic acids (See e.g., U.S. Pat. No. 6,399,339), reduction oftert-butyl (S)-chloro-5-hydroxy-3-oxohexanoate (See e.g., U.S. Pat. No. 6,645, 746; and WO 01/40450), reduction pyrrolotriazine-based compounds (See e.g., U.S. Appln. Publ. No. 2006/0286646); reduction of substituted acetophenones (See e.g., U.S. Pat. Nos. 6,800,477 and 8,748,143); and reduction of ketothiolanes (WO 2005/054491).

The present invention provides engineered ketoreductases capable of deracemizing the substrate compound (1), (6,7-dihydro-5H-pyrrolo[1,2-a]imidazol-7-ol), in one-pot, multi-enzyme system as shown in the following reaction and FIG. 1.

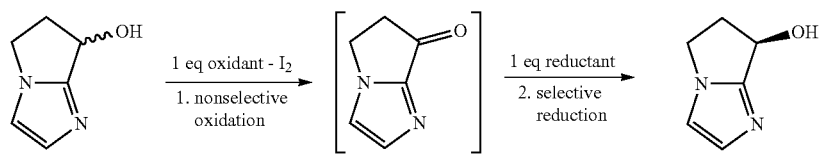

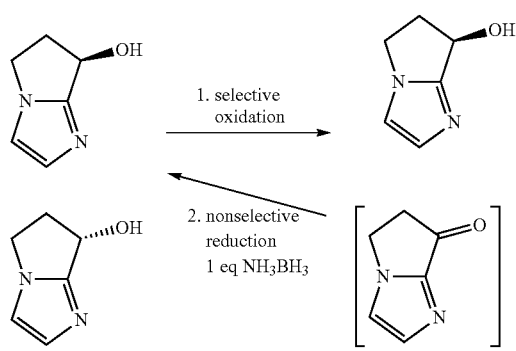

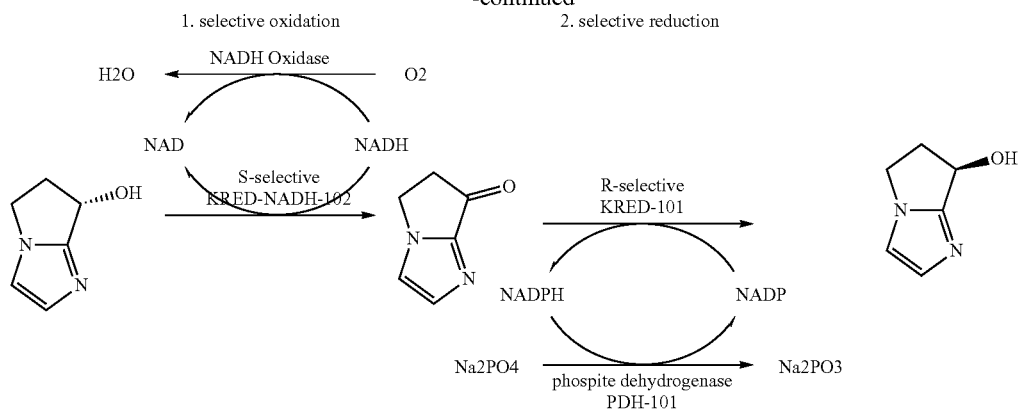

The present invention further provides improved ketoreductase enzymes and improved phosphite dehydrogenase enzymes, and methods for using the engineered ketoreductase and phosphite dehydrogenase enzymes to deracemize chiral compounds in one-pot, multi-enzyme system.

It is important to note that the desired product can be obtained in a one-pot, one-step, multi-enzyme system only if the oxidation and reduction reactions are orthogonal, compatible and non-interacting. These conditions are only satisfied if the oxidative ketoreductase and its corresponding recycling enzyme use one co-factor exclusively (e.g., NAD+), and reductive ketoreductase and its corresponding recycling enzyme use the opposite co-factor exclusively (i.e., NADPH).

Figure 2:
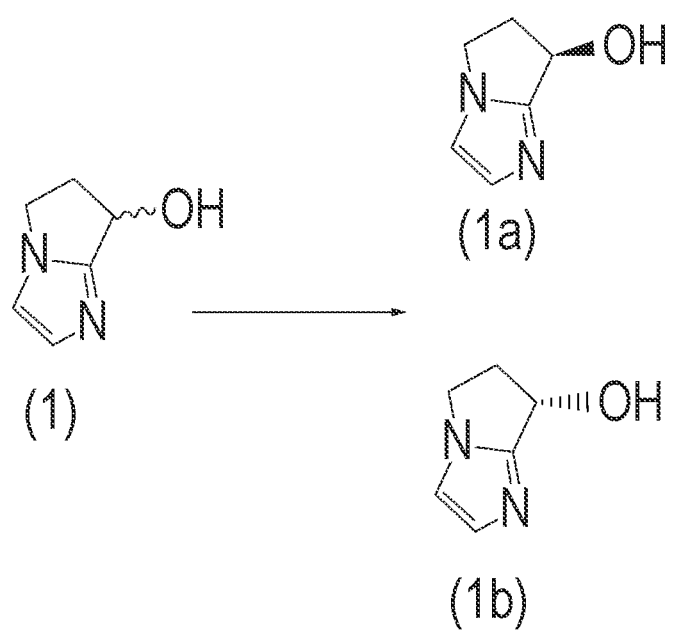
FIG. 2 provides the structures of substrate and product isomers.

Compound (1) has one chiral center and can exist in two different diastereomeric forms (1a and 1b). The deracemization reaction by a tandem of ketoreductases can result in two different enantiomeric products (1a-1b), as shown in FIG. 2 and below.

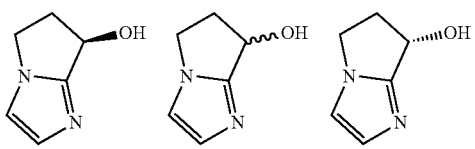

However, (1a) is the only desired product. The evolution program used in the development of the present invention was designed to improve activity of an S-selective ketoreductase that would oxidize the S-alcohol in the racemic mixture, generating a ketone substrate for an R-selective ketoreductase. Further, evolution program was designed to improve the selectivity, activity and cofactor preference of the R-selective ketoreductase. Evolution was also designed to improve activity, stability and cofactor preference of a phosphite dehydrogenase to enable deracemization of substrate (1) to product (1a) with minimal amount of ketone and (1b) in a one-pot, one-step, multi-enzyme process.

The ketoreductase polypeptide of SEQ ID NO:2 was selected as the initial backbone for development of the improved S-selective enzymes provided by the present invention. This enzyme was chosen as the starting backbone as ketone (2) was produced via oxidation of only (1b), leaving (1a). The ketoreductase polypeptide of SEQ ID NO:2 uses NAD+ as a co-factor with an efficiency greater than 200:1 over NADP+ and can be coupled with a commercially available NADH oxidase to recycle the co-factor.

The ketoreductase polypeptide of SEQ ID NO:2 was selected as the initial backbone for development of R-selective enzymes to reduce a ketone to product (1a) with initial selectivity of 92.7% e.e. Enantioselectivity values are calculated herein according to equation (1) provided below.

$$\{[(1a\ amount)-(1b\ amount)]/[(1a\ amount)+(1b\ amount)]\} \times 100 \qquad (1)$$

Indeed, the non-naturally occurring ketoreductase polypeptides of the present invention are ketoreductases engineered to have improved properties as compared to the naturally occurring ketoreductase of SEQ ID NO:2.

A phosphite dehydrogenase polypeptide was selected as the initial backbone for development of the improved PDH enzymes. This enzyme is equally efficient recycling both NADH and NADPH.

In some embodiments, the engineered ketoreductase polypeptides are capable of converting the substrate compound to product with an activity that is increased at least about 1.2 fold, 1.5 fold, 2 fold, 3 fold, 4 fold, 5 fold, 10 fold, 20 fold, 30 fold, 40 fold, 50 fold, or 100 fold relative to the activity of the reference polypeptide of SEQ ID NO:2 under suitable reaction conditions. In some embodiments, the engineered ketoreductase polypeptides are capable of converting the substrate compound to product with a percent conversion of at least about 40%, at least about 50%, at least about 60%, at least about 70%, at least about 80%, or at least about 90%, at least about 95%, at least about 98%, at least about 99%, in a reaction time of about 48 h, about 36 h, about 24 h, or even shorter length of time, under suitable reaction conditions.

In some embodiments, the engineered ketoreductases and phosphite dehydrogenases are capable of converting substrate compound (1) to product compound (1a) in enantiomeric excess over compound (1b) in a one-pot, one-step, multi-enzyme system. In some embodiments, the engineered ketoreductases and phosphite dehydrogenases are capable of converting compound (1) to compound (1a) in diastereomeric excess over compound (1b) under suitable reaction conditions.

As will be appreciated by those of skill in the art, some of the above-defined categories, unless otherwise specified, are not mutually exclusive. Thus, amino acids having side chains exhibiting two or more physico-chemical properties can be included in multiple categories. The appropriate classification of any amino acid or residue will be apparent to those of skill in the art, especially in light of the detailed invention provided herein.

In some embodiments, the improved engineered ketoreductase enzymes and engineered phosphite dehydrogenase enzymes comprise amino acid residue deletions in the naturally occurring ketoreductase or phosphite dehydrogenase polypeptides or deletions of amino acid residues in other engineered ketoreductase or phosphite dehydrogenase polypeptides. Thus, in some embodiments of the invention, the deletions comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase or phosphite dehydrogenase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As described herein, the ketoreductase or phosphite dehydrogenase polypeptides of the invention can be in the form of fusion polypeptides in which the ketoreductases or phosphite dehydrogenase polypeptides are fused to other polypeptides, such as antibody tags (e.g., myc epitope) or purifications sequences (e.g., His tags). Thus, in some embodiments, the ketoreductase and/or phosphite dehydrogenase polypeptides find use with or without fusions to other polypeptides.

In some embodiments, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised are apparent to those of skill in the art. These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(finoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzymes and engineered phosphite dehydrogenase enzymes can be targeted to a specific property of the enzyme.

Polynucleotides Encoding Engineered Enzymes

In another aspect, the present invention provides polynucleotides encoding the engineered ketoreductase enzymes and engineered phosphite dehydrogenase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase and/or engineered phosphite dehydrogenase can be introduced into appropriate host cells to express the corresponding ketoreductase or phosphite dehydrogenase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes and/or improved phosphite dehydrogenase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present invention specifically contemplates each and every possible variation of polynucleotides that could be made by selecting combinations based on the possible codon choices, and all such variations are to be considered specifically disclosed for any polypeptide disclosed herein, including the amino acid sequences presented in the Tables in the Examples. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells.

In some embodiments, the engineered ketoreductase or phosphite dehdyrogeanse sequences comprise sequences that comprise positions identified to be beneficial, as described in the Examples.

In some embodiments, isolated polynucleotides encoding an improved ketoreductase or phosphite dehydrogenase polypeptides are manipulated in a variety of ways to provide for improved expression and/or production of the polypeptides. Manipulation of the isolated polynucleotide prior to its insertion into a vector may be desirable or necessary, depending on the expression vector used. The techniques for modifying polynucleotides and nucleic acid sequences utilizing recombinant DNA methods are well known in the art.

For bacterial host cells, suitable promoters for directing transcription of the nucleic acid constructs of the present invention, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus lichenformis* penicillinase gene (penP), *Bacillus subtilis* xylA and xylB genes, and prokaryotic beta-lactamase gene (See e.g., Villa-Kamaroff et al., Proc. Natl. Acad. Sci. USA 75: 3727-3731 [1978]), as well as the tac promoter (See e.g., DeBoer et al., Proc. Natl Acad. Sci. USA 80: 21-25 [1983]). Additional suitable promoters are known to those in the art.

For filamentous fungal host cells, suitable promoters for directing the transcription of the nucleic acid constructs of the present invention include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters include, but are not limited to those from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, as well as other useful promoters for yeast host cells (See e.g., Romanos et al., Yeast 8:423-488 [1992]).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase, as well as other useful terminators for yeast host cells known in the art (See e.g,. Romanos et al., supra).

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase, as well as additional useful polyadenylation sequences for yeast host cells known in the art (See e.g., Guo et al., Mol. Cell. Biol., 15:5983-5990 [1995]).

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA, as well as additional signal peptides known in the art (See e.g., Simonen et al., Microbiol. Rev., 57: 109-137 [1993]).

Effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase, as well as additional useful signal peptide coding regions (See e.g., Romanos et al., 1992, supra).

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention or the PDH polypeptide of the present invention would be operably linked with the regulatory sequence.

Thus, in some embodiments, the present invention is also directed to a recombinant expression vector comprising a polynucleotide encoding an engineered ketoreductase polypeptide or a variant thereof, or an engineered phosphite dehydrogenase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector (i.e., a vector that exists as an extrachromosomal entity), the replication of which is independent of chromosomal replication, (e.g., a plasmid, an extrachromosomal element, a minichromosome, or an artificial chromosome). The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on or the origins of replication of plasmids pBR322, pUC19, pACYC177 (which plasmid has the P15A on), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (See e.g., Ehrlich, Proc. Natl. Acad. Sci. USA 75:1433 [1978]).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include, but are not limited to p3×FLAGTM™ expression vectors (Sigma-Aldrich), which include a CMV promoter and hGH polyadenylation site for expression in mammalian host cells and a pBR322 origin of replication and ampicillin resistance markers for amplification in *E. coli*. Other commercially available suitable expression vectors include but are not limited to the pBluescriptII SK(−) and pBK-CMV vectors (Stratagene), and plasmids derived from pBR322 (Gibco BRL), pUC (Gibco BRL), pREP4, pCEP4 (Invitrogen) or pPoly (See, Lathe et al., Gene 57:193-201 [1987]).

Host Cells for Expression of Engineered Polypeptides

The present invention also provides a host cell comprising a polynucleotide encoding an improved ketoreductase polypeptide or an improved phosphite dehydrogenase polypeptide of the present invention, the polynucleotide being operatively linked to one or more control sequences for expression of the ketoreductase enzyme or the phosphite dehydrogenase enzyme in the host cell. Host cells for use in expressing the KRED polypeptides encoded by the expression vectors of the present invention or the PDH polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture media and growth conditions for the above-described host cells are well known in the art.

Polynucleotides for expression of the ketoreductase or the phosphite dehydrogenase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

*Escherichia coli* W3110 is a host strain that finds use in the present invention, although it is not intended that the present invention be limited to this specific host strain. The expression vector was created by operatively linking a polynucleotide encoding an improved enzyme into the plasmid pCK110900 operatively linked to the lac promoter under control of the lacI repressor. The expression vector also contained the P15a origin of replication and the chloramphenicol resistance gene. Cells containing the subject polynucleotide in *Escherichia coli* W3110 can be isolated by subjecting the cells to chloramphenicol selection. Methods of Generating Engineered Ketoreductase Polypeptides and Engineered Phosphite Dehydrogenase Polypeptides.

In some embodiments, to make the improved KRED polynucleotides and polypeptides of the present invention, the naturally-occurring ketoreductase enzyme that catalyzes the reduction reaction is obtained (or derived) from *Candida parasilosis* or *Sporodiobolus salmonicolor*. In some embodiments, the parent polynucleotide sequence is codon optimized to enhance expression of the ketoreductase in a specified host cell. As an illustration, the parental polynucleotide sequence encoding the wild-type KRED polypeptide of *Sporodiobolus salmonicolor* was constructed from oligonucleotides prepared based upon the known polypeptide sequence of *Sporodiobolus salmonicolor* KRED sequence available from the Genbank database. The parental polynucleotide sequence was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity.

In some embodiments, the engineered ketoreductases are obtained by subjecting the polynucleotide encoding the naturally occurring ketoreductase to mutagenesis and/or directed evolution methods, as discussed above. Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,811,238, 5,830,721, 5,834,252, 5,837,458, 5,928,905, 6,096,548, 6,117,679, 6,132,970, 6,165,793, 6,180,406, 6,251,674, 6,265,201, 6,277,638, 6,287,861, 6,287,862, 6,291,242, 6,297,053, 6,303,344, 6,309,883, 6,319,713, 6,319,714, 6,323,030, 6,326,204, 6,335,160, 6,335,198, 6,344,356, 6,352,859, 6,355,484, 6,358,740, 6,358,742, 6,365,377, 6,365,408, 6,368,861, 6,372,497, 6,337,186, 6,376,246, 6,379,964, 6,387,702, 6,391,552, 6,391,640, 6,395,547, 6,406,855, 6,406,910, 6,413,745, 6,413,774, 6,420,175, 6,423,542, 6,426,224, 6,436,675, 6,444,468, 6,455,253, 6,479,652, 6,482,647, 6,483,011, 6,484,105, 6,489,146, 6,500,617, 6,500,639, 6,506,602, 6,506,603, 6,518,065, 6,519,065, 6,521,453, 6,528,311, 6,537,746, 6,573,098, 6,576,467, 6,579,678, 6,586,182, 6,602,986, 6,605,430, 6,613,514, 6,653,072, 6,686,515, 6,703,240, 6,716,631, 6,825,001, 6,902,922, 6,917,882, 6,946,296, 6,961,664, 6,995,017, 7,024,312, 7,058,515, 7,105,297, 7,148,054, 7,220,566, 7,288,375, 7,384,387, 7,421,347, 7,430,477, 7,462,469, 7,534,564, 7,620,500, 7,620,502, 7,629,170, 7,702,464, 7,747,391, 7,747,393, 7,751,986, 7,776,598, 7,783,428, 7,795,030, 7,853,410, 7,868,138, 7,783,428, 7,873,477, 7,873,499, 7,904,249, 7,957,912, 7,981,614, 8,014,961, 8,029,988, 8,048,674, 8,058,001, 8,076,138, 8,108,150, 8,170,806, 8,224,580, 8,377,681, 8,383,346, 8,457,903, 8,504,498, 8,589,085, 8,762,066, 8,768,871, 9,593,326, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). The stereochemistry of the products can be ascertained by various known techniques, and as provided in the Examples. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical ligation methods, or polymerase mediated methods) to form any desired continuous sequence. For example, polynucleotides and oligonucleotides of the invention can be prepared by chemical synthesis (e.g., using the classical phosphoramidite method described by Beaucage et al., Tet. Lett., 22:1859-69 [1981], or the method described by Matthes et al., EMBO J., 3:801-05 [1984], as it is typically practiced in automated synthetic methods). According to the phosphoramidite method, oligonucleotides are synthesized (e.g., in an automatic DNA synthesizer), purified, annealed, ligated and cloned in appropriate vectors. In addition, essentially any nucleic acid can be obtained from any of a variety of commercial sources (e.g., The Midland Certified Reagent Company, Midland, TX, The Great American Gene Company, Ramona, CA, ExpressGen Inc. Chicago, IL, Operon Technologies Inc., Alameda, CA, and many others).

Engineered ketoreductase enzymes and engineered phosphite dehydrogenase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as E. coli, are commercially available under the trade name CelLytic B™ (Sigma-Aldrich).

Chromatographic techniques for isolation of the ketoreductase and/or phosphite dehydrogenase polypeptides include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques are used to isolate the improved ketoreductase enzymes and/or improved phosphite dehydrogenase enzymes. For affinity chromatography purification, any antibody which specifically binds the ketoreductase polypeptide or the phosphite dehydrogenase polypeptide may be used. For the production of antibodies, various host animals, including but not limited to rabbits, mice, rats, etc., may be immunized by injection with the ketoreductase or the phosphite dehydrogenase. The ketoreductase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacillus* Calmette Guerin) and *Corynebacterium parvum*.

The ketoreductases and/or the phosphite dehydrogenases may be prepared and used in the form of cells expressing the enzymes, as crude extracts, or as isolated or purified preparations. The ketoreductases and/or the phosphite dehydrogenases may be prepared as lyophilizates, in powder form (e.g., acetone powders), or prepared as enzyme solutions. In some embodiments, the ketoreductases or the phosphite dehydrogenases can be in the form of substantially pure preparations.

In some embodiments, the ketoreductase polypeptides and/or the phosphite dehydrogenase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, NADP$^+$ (nicotinamide adenine dinucleotide phosphate), NADPH (the reduced form of NADP$^+$), NAD$^+$ (nicotinamide adenine dinucleotide) and NADH (the reduced form of NAD$^+$). Generally, the reduced form of the cofactor is added to the reaction mixture. The reduced NAD(P)H form can be optionally regenerated from the oxidized NAD(P)$^+$ form using a cofactor regeneration system. The term "cofactor regeneration system" refers to a set of reactants that participate in a reaction that reduces the oxidized form of the cofactor (e.g., NADP$^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD$^+$ or NADP$^+$, respectively, are known in the art and may be used in the methods described herein.

Experimental

Various features and embodiments of the invention are illustrated in the following representative examples, which are intended to be illustrative, and not limiting.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); RT (room temperature); CDS (coding sequence); DNA (deoxyribonucleic acid); RNA (ribonucleic acid); HPLC (high performance liquid chromatography); FIOPC (fold improvement over positive control); HTP (high throughput); LB (Luria broth); Sigma-Aldrich (Sigma-Aldrich, St. Louis, MO); Millipore (Millipore, Corp., Billerica MA); Difco (Difco Laboratories, BD Diagnostic Systems, Detroit, MI); Daicel (Daicel, West Chester, PA); Genetix (Genetix USA, Inc., Beaverton, OR); Molecular Devices (Molecular Devices, LLC, Sunnyvale, CA); Applied Biosystems (Applied Biosystems, part of Life Technologies, Corp., Grand Island, NY), Agilent (Agilent Technologies, Inc., Santa Clara, CA); Thermo Scientific (part of Thermo Fisher Scientific, Waltham, MA); Corning (Corning, Inc., Palo Alto, CA); and Bio-Rad (Bio-Rad Laboratories, Hercules, CA).

Example 1

Figure 3:
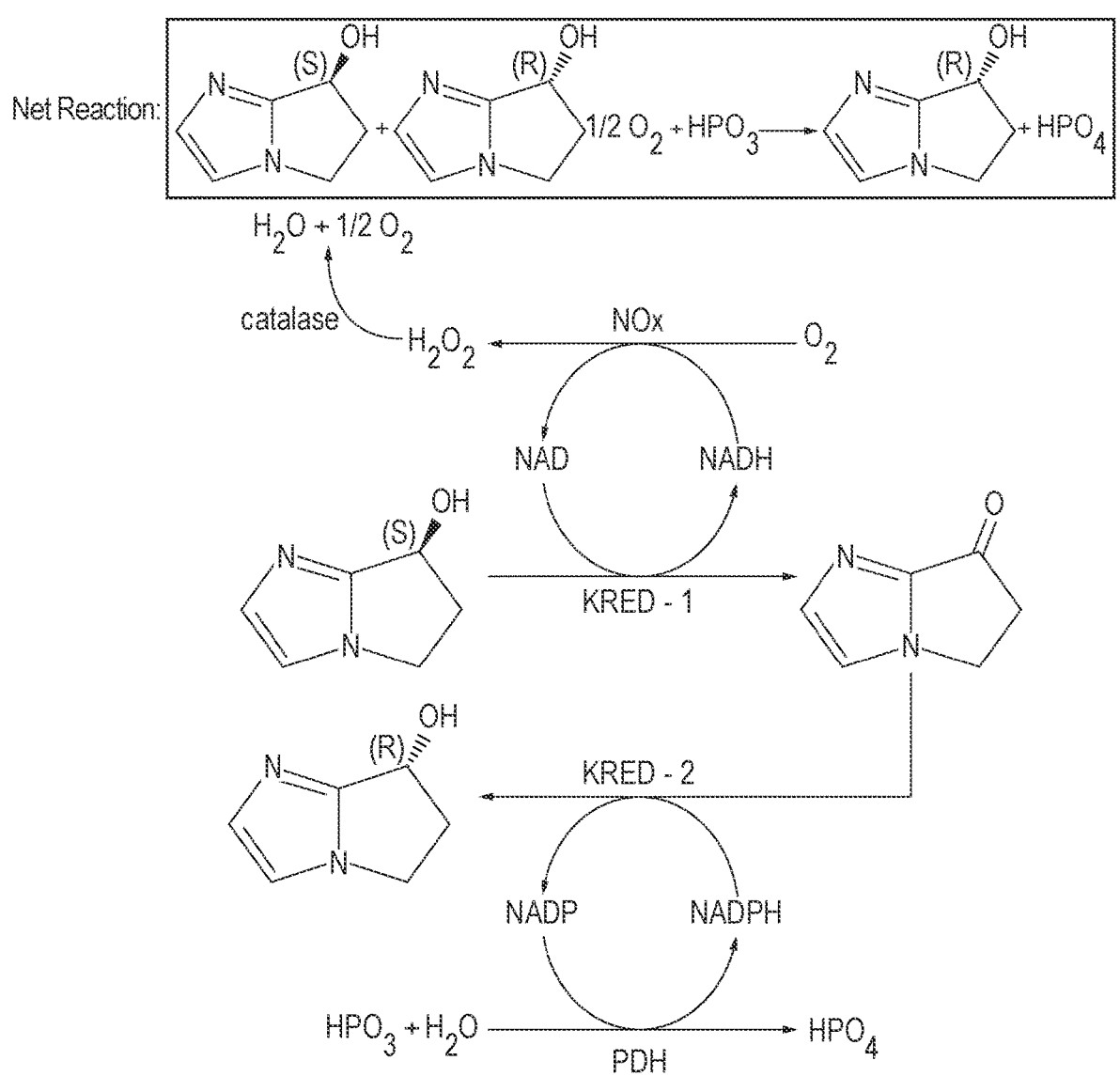
FIG. 3 provides the one-pot, multi-enzyme reaction scheme.
Figure 4:
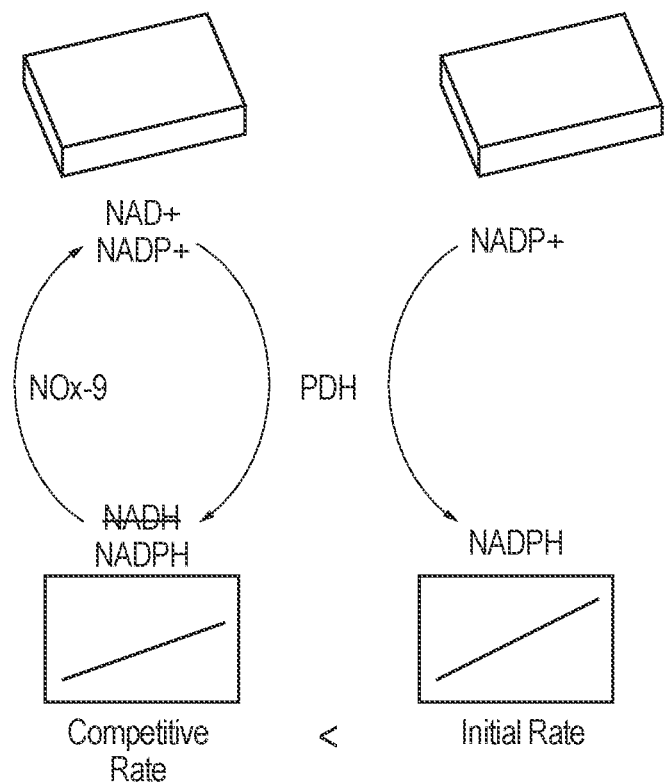
FIGS. 4 and 5 provide the cofactor competition assay schemes.
Figure 5:
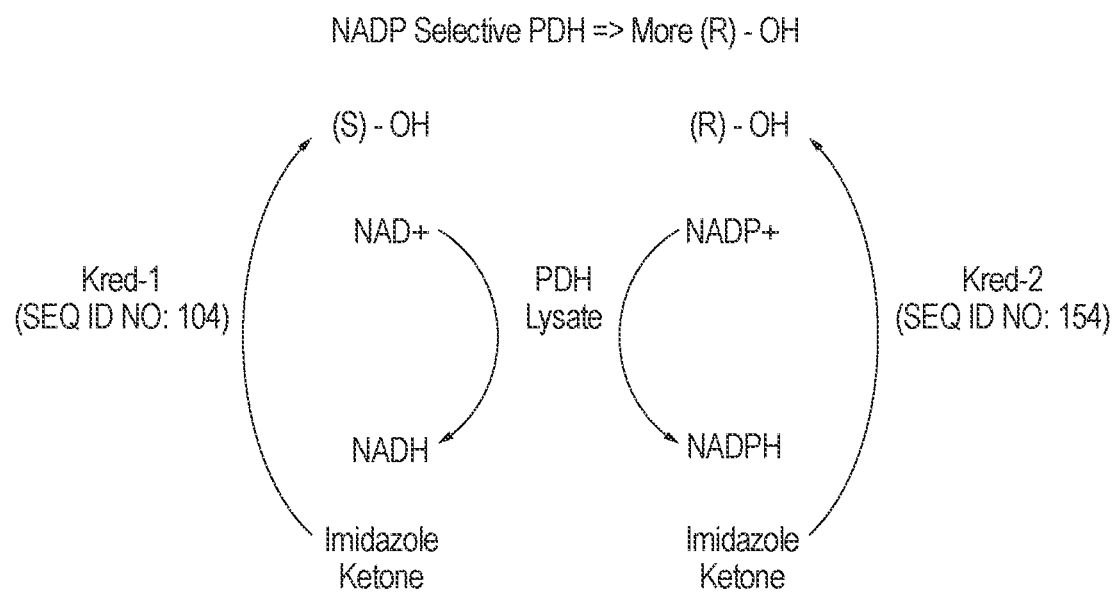
Figure 6:
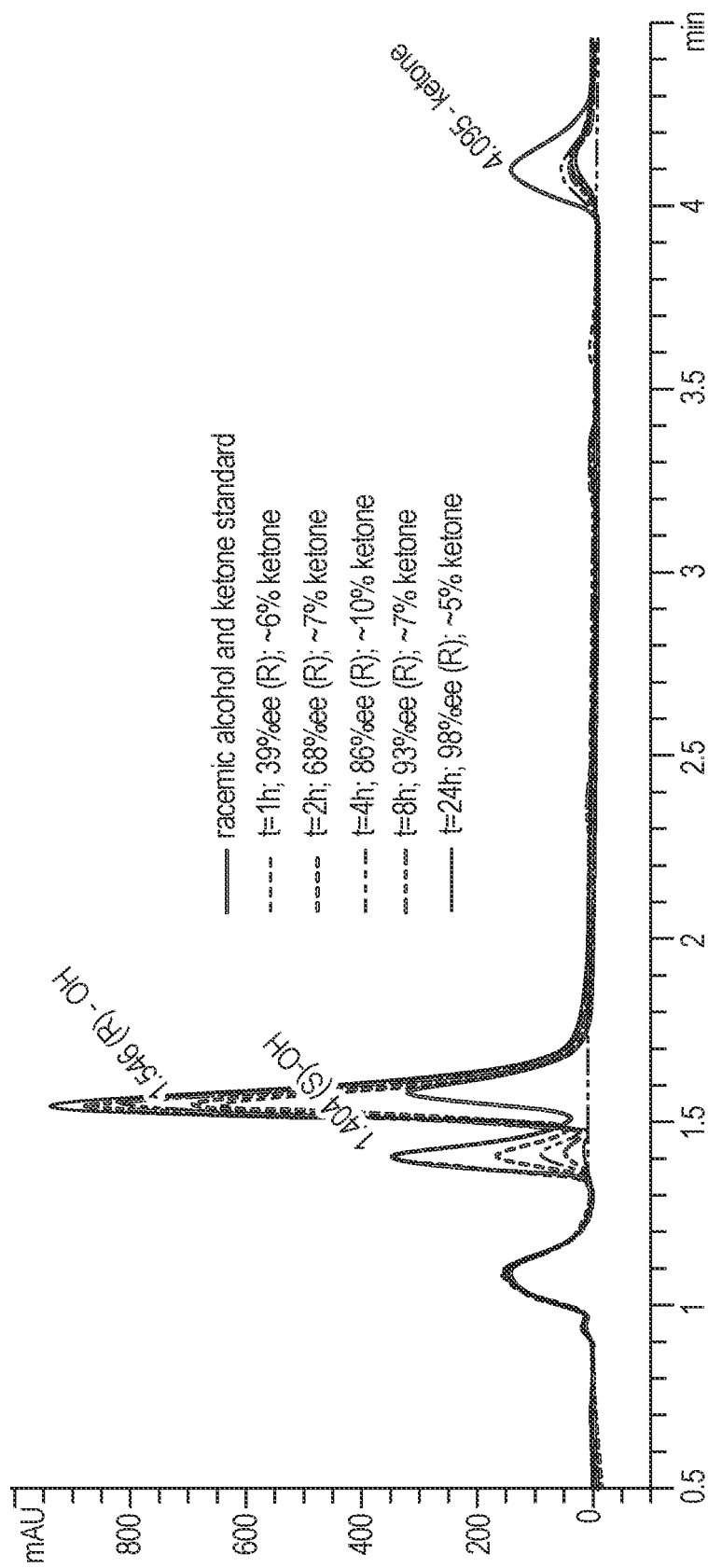
FIG. 6 provides the HPLC chromatogram of products obtained in one-pot, multi-enzyme reactions.

Ketoreductase and Phosphite Dehydrogenase Gene Construction and Expression Vectors The wild-type *Candida parapsilois* ketoreductase (KRED) encoding gene was amplified from genomic DNA and cloned into expression vector pCK11 0900 (See, FIG. 3 of US Pat. Appln. Publn. No. 2006/0195947, herein incorporated by reference) under the control of a lac promoter. The expression vector also contained the P15a origin of replication and the chloramphenicol resistance gene. The activity of the wild-type ketoreductase was confirmed as described in WO2008/042876. Polynucleotides encoding engineered ketoreductases of the present invention were likewise cloned into vector pCK11 0900 for expression in *E. coli* W311 0. Directed evolution of the KRED gene was carried out by first selecting the parent gene (i.e., SEQ ID NOS: 2, 6, 104) followed by library construction of variant genes in which positions associated with certain structural features were subjected to mutagenesis. These libraries were then plated, grown-up, and screened using HTP assays as described in Examples 2, 5 and 12.

The wild-type *Sporidiobolus salmonicolor* ketoreductase (KRED) encoding gene was synthesized for expression in *E. coli* based on the reported amino acid sequence of the ketoreductase and a codon optimization algorithm as described in Example 1 of WO2008/042876, incorporated herein by reference. The gene was synthesized using oligonucleotides composed of 42 nucleotides and cloned into expression vector pCK11 0900 (See, FIG. 3 of US Pat. Appln. Pubin. No. 2006/0195947, herein incorporated by reference) under the control of a lac promoter. The expression vector also contained the P15a origin of replication and the chloramphenicol resistance gene. The activity of the wild-type ketoreductase was confirmed as described in WO2008/042876. Polynucleotides encoding engineered ketoreductases of the present invention were likewise cloned into vector pCK11 0900 for expression in *E. coli* W311 0. Directed evolution of the KRED gene was caried out by first selecting the parent gene (i.e., SEQ ID NOS: 112, 124, 138) followed by library construction of variant genes in which positions associated with certain structural features were subjected to mutagenesis. These libraries were then plated, grown, and screened using HTP assays as described in Examples 3, 6, 7, 8 and 12.

A variant of the wild-type *Pseudomonas stutzeri* phosphite dehydrogenase (PDH) encoding gene was cloned into expression vector pCK11 0900 (See, FIG. 3 of US Pat. Appln. Publn. No. 2006/0195947, herein incorporated by reference) under the control of a lac promoter. The expression vector also contained the P15a origin of replication and the chloramphenicol resistance gene. The activity of the phosphite dehydrogenase was confirmed as described in WO2008/042876.

Polynucleotides encoding engineered phosphite dehydrogenases of the present invention were likewise cloned into vector pCK11 0900 for expression in *E. coli* W311 0. Directed evolution of the PDH gene was carried out by first selecting the parent gene (i.e., SEQ ID NOS: 172, 182, 200, 208, 260) followed by library construction of variant genes in which positions associated with certain structural features were subjected to mutagenesis. These libraries were then plated, grown, and screened using HTP assays as described in Examples 4, and 9 through 12.

Example 2

Production and Analysis of Engineered KRED Polypeptides for Oxidation

Plasmid libraries obtained through directed evolution and containing evolved ketoreductase genes were transformed into *E. coli* W3110 and placed on Luria-Bertani (LB) agar medium containing 1% glucose and 30 μg/ml chloramphenicol (CAM). After incubation for at least 16 h at 30° C., colonies were picked using a Q-bot® robotic colony picker (Genetix) into a 96-well shallow well microtiter plate containing 200 μL of LB, 1% glucose, and 30 μg/ml CAM. Cells were grown 18-20 h at 30° C., with shaking at 200 rpm. Twenty L of this culture was then transferred to 360 μL of Terrific Broth (TB), 1 mM $MgCl_2$, 2 mM $ZnSO_4$ and 30 μg/ml CAM. After incubation of deep well plates at 30° C. with shaking at 250 rpm for 2.5 h ($OD_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 μL of 20 mM Tris, 2 mM $ZnSO_4$, 1 mM $MgCl_2$ pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 5 and 12.

Example 3

Production and Analysis of Engineered KRED Polypeptides for Reduction

Plasmid libraries obtained through directed evolution and containing evolved ketoreductase genes were transformed into *E. coli* W3110 and placed on Luria-Bertani (LB) agar medium containing 1% glucose and 30 μg/ml chloramphenicol (CAM). After incubation for at least 16 h at 30° C., colonies were picked using a Q-bot® robotic colony picker (Genetix) into a 96-well shallow well microtiter plate containing 200 μL of LB, 1% glucose, and 30 μg/ml CAM. Cells were grown 18-20 h at 30° C., with shaking at 200 rpm. Twenty L of this culture was then transferred to 360 μL of Terrific Broth (TB), 1 mM $MgSO_4$, and 30 μg/ml CAM. After incubation of deep well plates at 30° C. with shaking at 250 rpm for 2.5 h ($OD_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 μL of 20 mM Tris, 1 mM $MgSO_4$, pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 6 through 8, and Example 12.

Example 4

Production and Analysis of Engineered Phosphite Dehydrogenase Polypeptides

Plasmid libraries obtained through directed evolution and containing evolved phosphite dehydrogenase genes were transformed into *E. coli* W3110 and placed on Luria-Bertani (LB) agar medium containing 1% glucose and 30 μg/ml chloramphenicol (CAM). After incubation for at least 16 h at 30° C., colonies were picked using a Q-bot® robotic colony picker (Genetix) into a 96-well shallow well microtiter plate containing 200 μL of LB, 1% glucose, and 30 μg/ml CAM. Cells were grown 18-20 h at 30° C., with shaking at 200 rpm. Twenty L of this culture was then transferred to 360 μL of Terrific Broth (TB) and 30 μg/ml CAM. After incubation of deep well plates at 30° C. with shaking at 250 rpm for 2.5 h ($OD_{600}$ 0.6-0.8), recombinant gene expression was induced by isopropyl thioglycoside (IPTG) to a final concentration of 1 mM. The plates were then incubated at 30° C. with shaking at 250 rpm for 18-21 h.

Cell cultures were pelleted at 3500×g for 20 min, and their supernatants were discarded. Cell pellets were lysed in 300 μL of 20 mM Tris, pH 7.5 with 1 g/L lysozyme and 0.5 g/L polymixin B sulfate by shaking at RT for 2 h. Samples were centrifuged at 3500×g for 20 min to clarify cellular debris, and the supernatant was used to carry out the transformations described in Examples 9 through 12.

Example 5

KRED Variants of SEQ ID NO:2

*E. coli* KRED variants were generated as described in Example 1. To analyze the activity of the variants, 20 μL of supernatant produced as described in Example 2 were added to a mixture of 180 μL racemic alcohol substrate (50 g/L), with 4 g/L $NAD^+$, 10 g/L commercially available NADH oxidase (NOx-9) and 100 mM FAD in 100 mM sodium phosphite pH 8.0. Reactions were incubated at 30° C. for 16-18h, and quenched via addition of 200 μL of 1M HCl. The quenched mixture was added to the sample and briefly mixed. Reaction samples were analyzed by UPLC to quantify residual substrate and products as described above. Significantly improved variants are provided in Table 5.1, below.

TABLE 5.1

Variants With Improved Activity Compared to SEQ ID NO: 2

| SEQ ID NO: | Amino Acid Substitutions (Relative to SEQ ID NO: 2) | Improvement |
|---|---|---|
| 4 | R309F | +++ |
| 6 | C57L | +++ |
| 8 | G114K | +++ |
| 10 | G272V | +++ |
| 12 | G263Y | +++ |
| 14 | L276F | +++ |
| 16 | C57I | +++ |
| 18 | G272P | +++ |
| 20 | G272L | +++ |
| 22 | G114M | ++ |
| 24 | G272S | +++ |
| 26 | G272Q | +++ |
| 28 | G272H | +++ |
| 30 | G272T | +++ |
| 32 | G114H | +++ |
| 34 | G272I | +++ |
| 36 | C57X/W286X | +++ |
| 38 | G272W | ++ |
| 40 | I279H | ++ |
| 42 | G263H | +++ |
| 44 | H45R | +++ |
| 46 | S268M | ++ |
| 48 | S268W | ++ |
| 50 | L274V | ++ |
| 52 | V83I | ++ |
| 54 | Y52D | ++ |
| 56 | I279R | +++ |
| 58 | Y52S | +++ |
| 60 | I279Q | ++ |
| 62 | L274I | ++ |
| 64 | D56L | +++ |
| 66 | K110T | + |
| 68 | P228S | ++ |
| 70 | S138V/A146S/M258V/T289S | + |
| 72 | K211R | + |
| 74 | K37R | + |
| 76 | K37R/K211R/G229R | ++ |
| 78 | K211R/G229R | + |
| 80 | G229R | ++ |
| 82 | K37R/G229R | + |
| 84 | K37R/K211R | ++ |
| 86 | L276M | +++ |
| 88 | I79T/V83S/A275N/L276M | +++ |
| 90 | V83S/A275N/L276M | ++ |
| 92 | V83S/L276M | ++ |
| 94 | A275N/L276M | +++ |
| 96 | L55F/C57A/L276M | + |
| 98 | A104G | ++ |
| 100 | C57I/A104G/G114H | ++++ |
| 102 | C57L/A104G/G114H/G229R | ++++ |
| 104 | Y52S/C57L/G272H\I279H/L296F | ++++ |
| 106 | Y52D/C57L/G272H | ++++ |
| 108 | Y52S/C57L/G272H/L274V/I279H/L296F | ++++ |
| 110 | Y52S/C57L/K110T/G272H/L296F | ++++ |

Key for Table 5.1
++++ >6
+++ >4 and <6
++ >2.5 and <4
+ >1.2 and <2.5

Example 6

KRED Variants of SEQ ID NO:112

*E. coli* KRED variants were generated as described in Example 1. To analyze the activity of the variants, 5 μL supernatant produced as described in Example 3 were added to 95 μL of 0.3 M phosphite buffer pH 7.9 containing 0.25 mM NADPH; 19 g/L ketone substrate and 5 g/L PDH. Reactions were incubated at room temperature for 16-18 hours with gentle shaking. Reactions were quenched via addition of 100 μL of 1M HCl. The quenched mixture (10 μL) was diluted into 190 μL of water. Reaction samples (10 μL) were analyzed by HPLC to quantify residual substrates and products as described above. Significantly improved variants are provided in Table 6.1, below.

TABLE 6.1

Variants With Improved Activity and Selectivity Compared to SEQ ID NO: 112

| SEQ ID NO: | Amino Acid Substitutions (Relative to SEQ ID NO: 112) | Activity Improvement | Selectivity Improvement |
|---|---|---|---|
| 114 | V24I/S220G/P314R/S315A | + | n.d. |
| 116 | V24I/T106P/S136A/S220G/L258V/C260A/P314R/S315A | + | n.d. |
| 118 | V24I/T106P/F214L/A250V/L258V/C260A/P314R/S315A | + | n.d. |
| 120 | T122E/I159V/L316E/I318L | ++ | n.d. |
| 122 | I159V/V251Q/Y272F/T277P/L316E/I318L/I330L | + | + |
| 124 | N207G | +++ | +++ |
| 126 | N207G | +++ | +++ |
| 128 | V135F | ++ | ++ |
| 130 | V135F | ++ | ++ |
| 132 | I139V/N207S | +++ | +++ |

Key for Table 6.1
| | Activity | Selectivity |
|---|---|---|
| +++ | >4 | >5 |
| ++ | >2.5 and <4 | >2 and <5 |
| + | >1.5 and <2.5 | >1 and <2 |

Example 7

KRED Variants of SEQ ID NO:124

*E. coli* KRED variants were generated as described in Example 1. To analyze the activity of the variants, 7.5 μL supernatant produced as described in Example 3 were added to 192.5 μL of 0.3 M phosphite buffer pH 7.9 containing 0.25 mM NADPH; 50 g/L ketone substrate and 5 g/L PDH. Reactions were incubated at room temperature for 16-18 hours with gentle shaking. Reactions were quenched via addition of 100 μL of 1M HCl. The quenched mixture (10 μL) was diluted into 190 μL of water. Reaction samples (10 μL) were analyzed by HPLC to quantify residual substrates and products as described above. Significantly improved variants are provided in Table 7.1, below.

TABLE 7.1

Variants With Improved Activity Compared to SEQ ID NO: 124

| SEQ ID NO: | Amino Acid Substitutions (Relative to SEQ ID NO: 124) | Activity Improvement |
|---|---|---|
| 134 | V95T | +++ |
| 136 | V24I/V95T/M228T | +++ |
| 138 | V95T/V135F/I139V/G207N | ++++ |
| 140 | K3Y/V95T | +++ |
| 142 | K3Y/V95T/M228T/P314R | +++ |
| 144 | A2T/Y101P/A179L/T182M/M228R/A238L/T282E | ++ |
| 146 | I159V/M228L/K309Q/I330L | + |

Key for Table 7.1
++++ >4
+++ >3 and <4
++ >2 and <3
+ >1.5 and <2

Example 8

KRED Variants of SEQ ID NO:138

E. coli KRED variants were generated as described in Example 1. To analyze the co-factor preference of the variants, four separate assays were utilized. First, 10 μL supernatant produced as described in Example 3 were added to 90 μL of 0.2 M phosphite buffer pH 7.9 containing 1 g/L ketone and 1 g/L of NADPH. The initial rate of NADPH consumption of the samples was analyzed via fluorescence with Ex λ=330 nm Em λ=445 nm, acquired for 180 seconds every 21 seconds.

Second, 20 μL supernatant produced as described in Example 3 were added to 190 μL of 0.2 M phosphite buffer pH 7.9 containing 1 g/L racemic alcohol and 2 g/L of NAD$^+$. The initial rate of NAD$^+$ consumption was analyzed via kinetic readings at UV 340 nm, data were acquired every 9 seconds for 5 minutes.

Third, 20 μL supernatant produced as described in Example 3 were added to 180 μL of 500 mM sodium phosphite containing 2 g/L imidazole ketone and 16.4 mM of NADPH; the samples were incubated at room temperature for 2 hr, shaking at 300 rpm. Reactions were quenched via addition of 200 μL of MeCN. After shaking for 5 minutes, 100 μL of the quenched reaction was transferred to a Millipore filter plate (45 micron pore size) with a co-star round bottom plate containing 100 μL of water to collect the filtrate and the mixture was spun at 4000 rpm for 2 minutes. Reaction samples (10 μL) were analyzed by HPLC to quantify residual substrate and product as described above.

Fourth, 20 μL superatant produced as described in Example 3 were added to 180 IL of 500 mM sodium phosphite containing 2 g/L imidazole ketone and 16.4 mM of NADPH; the samples were incubated at room temperature for 2 hr, shaking at 300 rpm. Reactions were quenched via addition of 200 μL of MeCN. After shaking for 5 minutes, 100 μL of the quenched reaction was transferred to a Millipore filter plate (45 micron pore size) with a co-star round bottom plate containing 100 μL of water to collect the filtrate and the mixture was spun at 4000 rpm for 2 minutes. Reaction samples (10 μL) were analyzed by HPLC to quantify residual substrate and product as described above. Co-factor specificity was calculated as (amount of product generated with NADPH)/
(amount of product generated with NADH)

Significantly improved variants are provided in Table 8.1, below.

TABLE 8.1

Variants With Improved Activity and Co-factor Specificity Compared to SEQ ID NO: 138

| SEQ ID NO: | Amino Acid Substitutions (Relative to SEQ ID NO: 138) | Activity Improvement | Co-factor Specificity Improvement |
|---|---|---|---|
| 148 | V24I/A43V/S47E/L49N/A67V/V68E/E70P/I91V/S220G | + | + |
| 150 | V24I/V68E/I91V/T218N/S220G | + | ++ |
| 152 | Y78F/P107G | + | ++ |
| 154 | K74A/Q75E/Y78F/A108V | ++ | +++ |
| 156 | Q75E/Y78F/N99P/A108V/D215S/S224A | ++ | +++ |
| 158 | G19S | +++ | ++ |
| 160 | T95C | +++ | + |
| 162 | S96G | +++ | + |
| 164 | G19S | +++ | + |
| 166 | M72Q | +++ | ++ |
| 168 | A67W | + | ++ |
| 170 | N114V | + | ++ |

Key for Table 8.1

| | Activity Improvement | Co-factor Specificity Improvement |
|---|---|---|
| +++ | >4 | >3 |
| ++ | >2 and <4 | >2 and <3 |
| + | >1 and <2 | >1 and <2 |

Example 9

PDH Variants of SEQ ID NO: 172

E. coli PDH variants were generated as described in Example 1. To analyze the activity of the variants, 5 μL supernatant produced as described in Example 3 were added to 95 μL of 0.5 M sodium phosphite buffer pH 7.9 containing 0.25 mM NADPH; 50 g/L ketone substrate and 2 g/L KRED of SEQ ID NO: 138. Reactions were incubated at 25° C. for 16-18 hours with gentle shaking. Reactions were quenched via addition of 100 μL of 1M HCL. The quenched mixture (10 μL) was diluted into 190 μL of water. Reaction samples (10 μL) were analyzed by HPLC to quantify residual substrates and products as described above. Significantly improved variants are provided in Table 9.1, below.

TABLE 9.1

Variants With Improved Activity Compared to SEQ ID NO: 172

| SEQ ID NO: | Amino Acid Substitutions (Relative to SEQ ID NO: 172) | Activity Improvement |
|---|---|---|
| 174 | R10K/C73A/R137Q | + |
| 176 | R10K/C73A/F78Y/V233I/N323D | + |
| 178 | R137Q/V233I/E303A/N323D | + |
| 180 | R10K/C73A/F78Y/R137Q/N323D/V325A | + |
| 182 | R44A/R132Q/N145G | + |
| 184 | E13D/R41A/Q63A/R132Q/A193S/S195E | + |
| 186 | R41A/R44A/A88R/A193S/S195E | + |
| 188 | E266V | + |
| 190 | E266W | + |
| 192 | E266S | + |
| 194 | R44A/R132Q/P136D/R137Q/N145G/I293L | ++ |
| 196 | R44A/R132Q/R137I/N145G/V233I/A308V/N323D | ++ |
| 198 | R44A/R132Q/Q135A/P136D/R137I/N145G/I293L | ++ |
| 200 | R44A/R132Q/R137I/N145G/I293L/N323D | ++ |

TABLE 9.1-continued

| | Variants With Improved Activity Compared to SEQ ID NO: 172 | |
|---|---|---|
| 202 | R44A/R132Q/N145G/S195E/I293L/N323D | ++ |
| 204 | R44A/V113S/R132Q/N145G | ++ |
| 206 | L18M/R44A/L119F/A124E/R132Q/R137I/N145G/I293L/N323D/A334K/C336R | +++ |
| 208 | R44A/L119F/R132Q/R137I/N145G/L158K/A175S/K177T/I293L/A317R/N323D | +++ |
| 210 | L18M/R44A/L119F/A124E/R132Q/R137I/N145G/L158K/K177T/I293L/N323D | +++ |
| 212 | L18M/R44A/L119F/A124E/R132Q/R137I/N145G/L158K/A175S/K177T/I293L/A317R/N323D | +++ |
| 214 | R44A/R69K/R120V/R132Q/R137I/N145G/A175T/S195E/I293L/N323D | +++ |
| 216 | S32V/R44A/R132Q/R137I/N145G/R186T/V233I/I293L/N323D/C336S | +++ |

Key for Table 9.1
+++   >4
++    >2 and <4
+     >1 and <2

Example 10

PDH Variants of SEQ ID NO:208

*E. coli* PDH variants were generated as described in Example 1. To analyze the co-factor preference of the variants, supernatant produced as described in Example 3 was diluted 4-fold with 50 mM Tris-HCl buffer, pH 7.5. Twenty μL of the diluted lysate was added to 180 μL of 0.1 M sodium phosphite buffer pH 7.9 and incubated overnight to consume residual NAD$^+$ and NADP$^+$ present in the lysate. The variants were then screened in three separate assays to analyze their co-factor specificity. First, for the initial rate NADP$^+$ assay, 0.2 mM NADP$^+$ in 0.1 M sodium phosphite buffer pH 7.9 was added and initial rate measured via fluorescence assay over 2 minutes. Second, for initial rate NAD$^+$ assay, 0.2 mM NAD$^+$ in 0.1M sodium phosphite buffer pH 7.9 was added and initial rate measured via fluorescence assay over 2 minutes. Third, a co-factor competition assay was performed. For this assay, 100 mM phosphite pH 7.9 containing 100 uM NADP, 1 mM NAD and 1 g/L NADH oxidase NOx-9 was added to the reaction. NOx-9 consumes all NADH immediately, leaving only NADPH signal, reduced by competition between NADP$^+$ and NAD$^+$. Reactions were quenched via addition of 100 μL of 1M HCl. The quenched mixture (10 μL) was diluted into 190 μL of water. Diluted reaction samples (10 μL) were analyzed by HPLC to quantify residual substrates and products as described above. Significantly improved variants are provided in Table 10.1, below.

TABLE 10.1

| | Variants With Improved Co-factor Specificity Compared to SEQ ID NO: 208 | | |
|---|---|---|---|
| SEQ ID NO: | Amino Acid Substitutions (Relative to SEQ ID NO: 208) | NADP+ Initial Rate Improvement | Cofactor Specificity Improvement |
| 218 | F78Y/F150I/F198L/R327S/L328P | + | + |
| 220 | N211A/D213Q/I322Q | + | + |
| 222 | A178P/C194L/N211A/D213Q/I322Q | + | + |
| 224 | F95I/N211A/D213Q/I322M | + | + |
| 226 | S32V/A59M/A124E/T177S/Q191H/R327D | + | + |
| 228 | L215P | + | + |
| 230 | L206N | + | + |
| 232 | T104F | ++ | + |
| 234 | T104L | ++ | + |
| 236 | E266S | + | + |
| 238 | V262P | + | + |
| 240 | V262D | + | + |
| 242 | V83A/E266A | + | + |
| 244 | D323N | + | + |

Key for Table 10.1
++   >2
+    >1 and <2

Example 11

Additional PDH Variants of SEQ ID NO:208

*E. coli* PDH variants were generated as described in Example 1. To analyze the co-factor preference of the variants, supernatant produced as described in Example 3 was diluted 4-fold with 50 mM Tris-HCl buffer, pH 7.5. Twenty µL of the diluted lysate was added to 180 µL of 0.1 M sodium phosphate buffer pH 7.9 and incubated overnight to consume residual NAD$^+$ and NADP$^+$ present in the lysate. The variants were then screened in three separate assays to analyze their co-factor specificity. First, for the initial rate NADP$^+$ assay 0.2 mM NADP$^+$ in 0.1 M sodium phosphate buffer pH 7.9 was added and initial rate measured via fluorescence assay over 2 minutes. Second, for initial rate NAD$^+$ assay, 0.2 mM NAD$^+$ in 0.1M sodium phosphate buffer pH 7.9 was added and initial rate measured via fluorescence assay over 2 minutes. Third, a co-factor competition assay was performed. For this assay, three µL of pre-incubated lysate was added to 97 µL of 200 mM phosphite pH 7.9 containing 2 mM NAD, 0.2 mM NADP, 2 g/L KRED of SEQ ID NO:138, 4 g/L KRED of SEQ ID NO: 104 and 10 g/L ketone (2). Reactions were quenched via addition of 100 µL of 1M HCl. The quenched mixture (10 µL) was diluted into 190 µL of water. Diluted reaction samples (10 µL) were analyzed by reverse phase HPLC to quantify residual substrate and both enantiomers of the product as described above. Significantly improved variants are provided in Table 11.1, below.

| SEQ ID NO: | Amino Acid Substitutions (Relative to SEQ ID NO: 208) | Cofactor Specificity Improvement |
|---|---|---|
| 246 | V83A/T104L/L206N | +++ |
| 248 | A74T/V83A/L206N | ++ |
| 250 | T104L/V262L | +++ |
| 252 | T104L/L206N | +++ |
| 254 | S295R | +++ |
| 256 | V96G | +++ |
| 258 | T104M | + |

Key for Table 11.1
+++ >8
++ >4 and <8
+ >2 and <4

Example 12

Production of Engineered Polypeptides and Performance Validation

Plasmids comprising variants obtained through directed evolution of the KRED of SEQ ID NO:2 and containing evolved ketoreductase genes were transformed into *E. coli* W3110 and placed on Luria-Bertani (LB) agar medium containing 1% glucose and 30 µg/ml chloramphenicol (CAM). After incubation for at least 16 h at 30° C., a single colony was picked into 5 mL of LB, 1% glucose, and 30 µg/ml CAM. Cells were grown 18-20 h at 30° C., with shaking at 250 rpm. This culture was then transferred into Terrific Broth (TB), 2 mM ZnSO$_4$, 1 mM MgSO$_4$, and 30 µg/ml CAM at a final OD$_{600}$ of ~0.02 and a final volume of 250 mL. After incubation of the flasks at 30° C. with shaking at 250 rpm for 3.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5 containing 2 mM ZnSO$_4$ and 1 mM MgSO$_4$, resuspended in 30 ml of the same buffer, and lysed using a cell disruptor at 18-20 kpsi. Lysates were clarified at 10000×g for 60 min, and clarified supernatants were lyophilized to an off white powder.

Plasmids of comprising variants obtained through directed evolution of the KRED of SEQ ID NOS: 112 and 138, and containing evolved ketoreductase genes were transformed into *E. coli* W3110 and placed on Luria-Bertani (LB) agar medium containing 1% glucose and 30 µg/ml chloramphenicol (CAM). After incubation for at least 16 h at 30° C., a single colony was picked into 5 mL of LB, 1% glucose, and 30 µg/ml CAM. Cells were grown 18-20 h at 30° C., with shaking at 250 rpm. This culture was then transferred into Terrific Broth (TB), and 30 µg/ml CAM at a final OD$_{600}$ of ~0.02 and a final volume of 250 mL. After incubation of the flasks at 30° C. with shaking at 250 rpm for 3.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5, resuspended in 30 ml of the same buffer, and lysed using a cell disruptor at 18-20 kpsi. Lysates were clarified at 10000×g for 60 min, and clarified supernatants were lyophilized to an off white powder.

Plasmids comprising variants obtained through directed evolution of the PDH of SEQ ID NOS: 172 and 208, and containing evolved phosphite dehydrogenase genes were transformed into *E. coli* W3110 and placed on Luria-Bertani (LB) agar medium containing 1% glucose and 30 µg/ml chloramphenicol (CAM). After incubation for at least 16 h at 30° C., a single colony was picked into 5 mL of LB, 1% glucose, and 30 µg/ml CAM. Cells were grown 18-20 h at 30° C., with shaking at 250 rpm. This culture was then transferred into Terrific Broth (TB), and 30 µg/ml CAM at a final OD$_{600}$ of ~0.02 and a final volume of 250 mL. After incubation of the flasks at 30° C. with shaking at 250 rpm for 3.5 h (OD$_{600}$ 0.6-0.8), recombinant gene expression was induced by isopropyl thioglycoside (IPTG) to a final concentration of 1 mM. The flask was then incubated at 30° C. with shaking at 250 rpm for 18-21 h. Cells were pelleted at 3500×g for 20 min, and the supernatant was discarded. The cell pellet was washed in 50 mL ice cold 50 mM sodium phosphate pH 7.5, resuspended in 30 ml of the same buffer, and lysed using a cell disruptor at 18-20 kpsi. Lysates were clarified at 10000×g for 60 min, and clarified supernatants were lyophilized to an off white powder.

To evaluate the final compound under process like conditions, 50 g/L of racemic alcohol substrate in 500 mM sodium phosphite buffer pH 7.9, 0.1 g/L NAD, 0.1 g/L NADP, 2.5 g/L KRED of SEQ ID NO: 104, 10 g/L commercially available NADH oxidase NOx-9, 2.5 g/L KRED of SEQ ID: 154, 10 g/L PDH of SEQ ID NO:250 was stirred under stream of oxygen with 1% v/v antifoam at room temperature for 24 hours resulting in 93% conversion of substrate and 99.5% enantiomeric excess of (R)-alcohol 1a. Reaction samples were analyzed by reverse phase HPLC to quantify residual substrate and products as described above.

While various specific embodiments have been illustrated and described, it will be appreciated that various changes can be made without departing from the spirit and scope of the invention(s).

All publications, patents, patent applications and other documents cited in this application are hereby incorporated by reference in their entireties for all purposes to the same extent as if each individual publication, patent, patent application or other document were individually indicated to be incorporated by reference for all purposes.

The invention claimed is:

1. An engineered phosphite dehydrogenase variant having at least 90% sequence identity to the polypeptide sequence SEQ ID NO: 172 wherein said engineered phosphite dehydrogenase variant comprises an alanine at position 44 as compared to SEQ ID NO: 172.

2. The engineered phosphite dehydrogenase variant of claim 1, wherein said engineered phosphite dehydrogenase variant further comprises at least one substitution or substitution set as compared to SEQ ID NO: 172 at one or more positions selected from positions 10/73/78/137/323/325, 10/73/78/233/323, 10/73/137, 13/41/63/132/193/195, 18/119/124/132/137/145/158/175/177/293/317/323, 18/119/124/132/137/145/158/177/293/323, 18/119/124/132/137/145/293/323/334/336, 32/132/137/145/186/233/293/323/336, 41/88/193/195, 69/120/132/137/145/175/195/293/323, 113/132/145, 119/132/137/145/158/175/177/293/317/323, 132/135/136/137/145/293, 132/136/137/145/293, 132/137/145/233/308/323, 132/137/145/293/323, 132/145, 132/145/195/293/323, 137/233/303/323, and 266, wherein said positions are numbered with reference to SEQ ID NO: 172.

3. The engineered phosphite dehydrogenase variant of claim 1, wherein said engineered phosphite dehydrogenase variant has at least 95% sequence identity to SEQ ID NO: 172.

4. The engineered phosphite dehydrogenase variant of claim 1, wherein said engineered phosphite dehydrogenase variant comprises a substitution set as compared to SEQ ID NO: 172 as in any of the engineered phosphite dehydrogenase variants selected from SEQ ID NOS: 182, 186, 194, 196, 198, 198, 200, 204, 206, 208, 210, 212, 214, 216, 218, 220, 222, 224, 226, 228, 230, 232, 235, 236, 238, 240, 242, 244, 246, 248, 250, 252, 254, 256, 258, and 260.

5. The engineered phosphite dehydrogenase variant of claim 1, wherein said engineered phosphite dehydrogenase variant comprises a polypeptide sequence selected from the sequences set forth in SEQ ID NOS: 182, 186, 194, 196, 198, 198, 200, 204, 206, 208, 210, 212, 214, 216, 218, 220, 222, 224, 226, 228, 230, 232, 235, 236, 238, 240, 242, 244, 246, 248, 250, 252, 254, 256, 258, and 260.

6. A composition comprising at least one phosphite dehydrogenase variant set forth in claim 1.

* * * * *

SEQUENCE LISTING

```
Sequence total quantity: 260
SEQ ID NO: 1              moltype = DNA   length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 1
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc gcgtaacct gtctcgtatc  420
ccggataacg tatctgctga tgttgctgct gcttctaccg acgctgttct gactccgtac  480
cacgctatca aatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aggtgttat catgccggtt  780
ggtctggtgg ctccgaacct gtcttttaac ctgggtgacc tggctctgcg tgaaatccgt  840
atcctgggtt ctttctgggg taccaccaac gacctggacg acgttctgaa actggtttct  900
gaaggtaaag ttaaaccggt tgtacgttct gctaaactga agaactgcc ggaatacatc  960
gaaaaactgc gtaacaacgc ttacgaaggt cgtgttgttt tcaacccgta a          1011

SEQ ID NO: 2              moltype = AA   length = 336
FEATURE                   Location/Qualifiers
REGION                    1..336
                          note = KRED-NADH-102 variant
source                    1..336
                          mol_type = protein
                          organism = synthetic construct
SEQUENCE: 2
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                            336

SEQ ID NO: 3              moltype = DNA   length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 3
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc gcgtaacct gtctcgtatc  420
ccggataacg tatctgctga tgttgctgct gcttctaccg acgctgttct gactccgtac  480
cacgctatca aatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aggtgttat catgccggtt  780
ggtctggtgg ctccgaacct gtcttttaac ctgggtgacc tggctctgcg tgaaatccgt  840
atcctgggtt ctttctgggg taccaccaac gacctggacg acgttctgaa actggtttct  900
gaaggtaaag ttaaaccggt tgtatttcct gctaaactga agaactgcc ggaatacatc  960
gaaaaactgc gtaacaacgc ttacgaaggt cgtgttgttt tcaacccgta a          1011

SEQ ID NO: 4              moltype = AA   length = 336
FEATURE                   Location/Qualifiers
REGION                    1..336
                          note = KRED-NADH-102 variant
source                    1..336
                          mol_type = protein
                          organism = synthetic construct
SEQUENCE: 4
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
```

```
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLALREIR ILGSFWGTTN DLDDVLKLVS    300
EGKVKPVVFS AKLKELPEYI EKLRNNAYEG RVVFNP                             336

SEQ ID NO: 5            moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 5
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactt gggtgacaac    180
tacgttatgg gtcacgaaat cgctggtacc gttgctgctg ttggtgatga cgttatcaac    240
tacaaagtag gtgaccgtgt agcttgtgtt ggtccgaacg gtgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa agaagctcg tgaccaggct aaaaaactgg gtgctgacgc tgtttacgaa    660
acctgccgg aatctatctc tccgggttct ttctctgctt gcttcgactt cgtttctgtt    720
caggctacct cgacgtttg ccagaaatac gttgaaccga aaggtgttat catgccggtt    780
ggtctgggtg ctccgaacct gtctttttaac ctgggtgacc tggctctgcg tgaaatccgt    840
atcctgggtt cttctctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 6            moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 6
MSIPSSQYGF VFNKQSGLKL RNDLPVHKPK AGQLLLKVDA VGLCHSDLHV IYEGLDLGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLALREIR ILGSFWGTTN DLDDVLKLVS    300
EGKVKPVVRS AKLKELPEYI EKLRNNAYEG RVVFNP                             336

SEQ ID NO: 7            moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 7
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg aagactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa agaagctcg tgaccaggct aaaaaactgg gtgctgacgc tgtttacgaa    660
acctgccgg aatctatctc tccgggttct ttctctgctt gcttcgactt cgtttctgtt    720
caggctacct cgacgtttg ccagaaatac gttgaaccga aaggtgttat catgccggtt    780
ggtctgggtg ctccgaacct gtctttttaac ctgggtgacc tggctctgcg tgaaatccgt    840
atcctgggtt cttctctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 8            moltype = AA   length = 336
FEATURE                 Location/Qualifiers
REGION                  1..336
                        note = KRED-NADH-102 variant
source                  1..336
                        mol_type = protein
                        organism = synthetic construct
```

```
SEQUENCE: 8
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFKDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                           336

SEQ ID NO: 9            moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 9
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc gcgtaacct gtctcgtatc  420
ccggataacg tatctgctga tgttgctgct gcttctaccg acgctgttct gactccgtac  480
cacgctatca aatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aaggtgttat catgccggtt  780
ggtctgggtg ctccgaacct gtcttttaac ctggttgacc tggctctgcg tgaaatccgt  840
atcctgggtt cttttctgggg taccaccaac gacctggacg acgttctgaa actggttttct  900
gaaggtaaag ttaaaccggt tgtacgttct gctaaactga agaactgcc ggaatacatc  960
gaaaaactgc gtaacaacgc ttacgaaggt cgtgttgttt tcaaccgta a            1011

SEQ ID NO: 10           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 10
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LVDLALREIR ILGSFWGTTN DLDDVLKLVS  300
EGKVKPVVRS AKLKELPEYI EKLRNNAYEG RVVFNP                           336

SEQ ID NO: 11           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 11
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc gcgtaacct gtctcgtatc  420
ccggataacg tatctgctga tgttgctgct gcttctaccg acgctgttct gactccgtac  480
cacgctatca aatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aaggtgttat catgccggtt  780
ggtctgtatg ctccgaacct gtcttttaac ctgggtgacc tggctctgcg tgaaatccgt  840
atcctgggtt cttttctgggg taccaccaac gacctggacg acgttctgaa actggttttct  900
gaaggtaaag ttaaaccggt tgtacgttct gctaaactga agaactgcc ggaatacatc  960
gaaaaactgc gtaacaacgc ttacgaaggt cgtgttgttt tcaaccgta a            1011

SEQ ID NO: 12           moltype = AA   length = 336
FEATURE                 Location/Qualifiers
REGION                  1..336
                        note = KRED-NADH-102 variant
```

```
source                    1..336
                          mol_type = protein
                          organism = synthetic construct
SEQUENCE: 12
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLYAPNLSFN LGDLALREIR ILGSFWGTTN DLDDVLKLVS   300
EGKVKPVVRS AKLKELPEYI EKLRNNAYEG RVVFNP                             336

SEQ ID NO: 13             moltype = DNA  length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 13
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc gcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaaactcg tgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggcttttcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 14             moltype = AA  length = 336
FEATURE                   Location/Qualifiers
REGION                    1..336
                          note = KRED-NADH-102 variant
source                    1..336
                          mol_type = protein
                          organism = synthetic construct
SEQUENCE: 14
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLAFREIR ILGSFWGTTN DLDDVLKLVS   300
EGKVKPVVRS AKLKELPEYI EKLRNNAYEG RVVFNP                             336

SEQ ID NO: 15             moltype = DNA  length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 15
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggacat ggtgacaac    180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc gcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaaactgg tgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggcttttcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 16             moltype = AA  length = 336
```

```
FEATURE                 Location/Qualifiers
REGION                  1..336
                        note = KRED-NADH-102 variant
source                  1..336
                        mol_type = protein
                        organism = synthetic construct
SEQUENCE: 16
MSIPSSQYGF VFNKQSGLKL RNDLPVHKPK AGQLLLKVDA VGLCHSDLHV IYEGLDIGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                           336

SEQ ID NO: 17           moltype = DNA  length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 17
atgtctatcc cgtcttctca gtatggtttc gtatttaaca acagtctgg tctgaaactg    60
cgcaacgatc tgccagtaca caagccgaaa gctggtcaac tgctgctgaa agtagatgca  120
gtaggtctgt gccactctga tctgcacgtt atctacgaag gctggactg cggtgacaac   180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aaggtgttat catgccggtt  780
ggtctgggtg ctccgaacct gtcttttaac ctgccagacc tggctctgcg tgaaatccgt  840
atcctggtt ctttctgggg taccaccaac gacctggacg acgttctgaa actggtttct  900
gaaggtaaag ttaaaccggt tgtacgttct gctaaactga agaactgcc ggaatacatc  960
gaaaaactgc gtaacaacgc ttacgaaggt cgtgttgttt tcaacccgta a           1011

SEQ ID NO: 18           moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 18
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LPDLALREIR ILGSFWGTTN DLDDVLKLVS  300
EGKVKPVVRS AKLKELPEYI EKLRNNAYEG RVVFNP                           336

SEQ ID NO: 19           moltype = DNA  length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 19
atgtctatcc cgtcttctca gtatggtttc gtatttaaca acagtctgg tctgaaactg    60
cgcaacgatc tgccagtaca caagccgaaa gctggtcaac tgctgctgaa agtagatgca  120
gtaggtctgt gccactctga tctgcacgtt atctacgaag gctggactg cggtgacaac   180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccctgctg gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aaggtgttat catgccggtt  780
ggtctgggtg ctccgaacct gtcttttaac ctgccagacc tggctctgcg tgaaatccgt  840
atcctggtt ctttctgggg taccaccaac gacctggacg acgttctgaa actggtttct  900
gaaggtaaag ttaaaccggt tgtacgttct gctaaactga agaactgcc ggaatacatc  960
```

```
gaaaaactgc gtaacaacgc ttacgaaggt cgtgttgttt tcaacccgta a           1011

SEQ ID NO: 20          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 20
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LLDLALREIR ILGSFWGTTN DLDDVLKLVS  300
EGKVKPVVRS AKLKELPEYI EKLRNNAYEG RVVFNP                            336

SEQ ID NO: 21          moltype = DNA   length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 21
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccggtgg ttgcggtggt ttgcaaatac  300
tgccgtggtg ctatcgacaa cgtttgcaaa aacgctttca tggactggtt cggtctgggt  360
tatgatggtg gctatcaaca ataccgctgt gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaact ctgctgatc ggtgctggt   540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aggtgttat catgccggtt  780
ggtctgggtg ctccgaacct gtcttttaac ctgggtgact tggctctgcg tgaaatccgt  840
atcctgggtt ctttctgggg taccaccaac gacctggacg acgttctgaa actggtttct  900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 22          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 22
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFMDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                            336

SEQ ID NO: 23          moltype = DNA   length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 23
atgtctatcc cgtcttctca gtatggtttc gtatttaaca aacagtctgg tctgaaactg   60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg tgactggtt cggtctgggt   360
tatgatggtg gctatcaaca ataccgctgt gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct tcgacgtttg ccagaaatac gttgaaccga aggtgttat catgccggtt   780
```

```
ggtctgggtg ctccgaacct gtcttttaac ctgagtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a             1011
```

```
SEQ ID NO: 24            moltype = AA   length = 336
FEATURE                  Location/Qualifiers
REGION                   1..336
                         note = KRED-NADH-102 variant
source                   1..336
                         mol_type = protein
                         organism = synthetic construct
SEQUENCE: 24
MSIPSSQYGF VFNKQSGLKL RNDLPVHKPK AGQLLLKVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LSDLALREIR ILGSFWGTTN DLDDVLKLVS    300
EGKVKPVVRS AKLKELPEYI EKLRNNAYEG RVVFNP                              336
```

```
SEQ ID NO: 25            moltype = DNA   length = 1011
FEATURE                  Location/Qualifiers
misc_feature             1..1011
                         note = KRED-NADH-102 variant
source                   1..1011
                         mol_type = other DNA
                         organism = synthetic construct
SEQUENCE: 25
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg taacgctat ccaggttgct aaagcattcg gtgctaaagt taccgttctg    600
gacaaaaaaa aagaagctcg tgaccaggct aaaaaactgg gtgctgacgc tgtttacgaa    660
acc ctgccgg aatctatctc tccgggttct ttctctgctt gcttcgactt cgtttctgtt    720
caggctacct cgacgtttg ccagaaatac gttgaaccga aaggtgttat catgccggtt     780
ggtctgggtg ctccgaacct gtcttttaac ctgcaagacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011
```

```
SEQ ID NO: 26            moltype = AA   length = 336
FEATURE                  Location/Qualifiers
REGION                   1..336
                         note = KRED-NADH-102 variant
source                   1..336
                         mol_type = protein
                         organism = synthetic construct
SEQUENCE: 26
MSIPSSQYGF VFNKQSGLKL RNDLPVHKPK AGQLLLKVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LQDLALREIR ILGSFWGTTN DLDDVLKLVS    300
EGKVKPVVRS AKLKELPEYI EKLRNNAYEG RVVFNP                              336
```

```
SEQ ID NO: 27            moltype = DNA   length = 1011
FEATURE                  Location/Qualifiers
misc_feature             1..1011
                         note = KRED-NADH-102 variant
source                   1..1011
                         mol_type = other DNA
                         organism = synthetic construct
SEQUENCE: 27
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg taacgctat ccaggttgct aaagcattcg gtgctaaagt taccgttctg    600
```

```
gacaaaaaaa aagaagctcg tgaccaggct aaaaaactgg gtgctgacgc tgtttacgaa    660
accctgccgg aatctatctc tccgggttct ttctctgctt gcttcgactt cgttctgtt     720
caggctacct tcgacgtttg ccagaaatac gttgaaccga aggtgttat catgccggtt     780
ggtctgggtg ctccgaacct gtcttttaac ctgcatgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc     960
gaaaaactgc gtaacaacgc ttacgaaggt cgtgttgttt tcaacccgta a             1011

SEQ ID NO: 28              moltype = AA   length = 336
FEATURE                    Location/Qualifiers
REGION                     1..336
                           note = KRED-NADH-102 variant
source                     1..336
                           mol_type = protein
                           organism = synthetic construct
SEQUENCE: 28
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LHDLALREIR ILGSFWGTTN DLDDVLKLVS   300
EGKVKPVVRS AKLKELPEYI EKLRNNAYEG RVVFNP                             336

SEQ ID NO: 29              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 29
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgccgtac                480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgttctgtt    720
caggctacct tcgacgtttg ccagaaatac gttgaaccga aggtgttat catgccggtt    780
ggtctgggtg ctccgaacct gtcttttaac ctgacagacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a             1011

SEQ ID NO: 30              moltype = AA   length = 336
FEATURE                    Location/Qualifiers
REGION                     1..336
                           note = KRED-NADH-102 variant
source                     1..336
                           mol_type = protein
                           organism = synthetic construct
SEQUENCE: 30
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LTDLALREIR ILGSFWGTTN DLDDVLKLVS   300
EGKVKPVVRS AKLKELPEYI EKLRNNAYEG RVVFNP                             336

SEQ ID NO: 31              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 31
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcc gtgactggtt cggtctgggt   360
tatgatggtg gctatcaaca atacctgctg gtaactcgcc cgcgtaacct gtctcgtatc   420
```

```
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttcgaaggt cgtgttgttt caaccccgta a              1011

SEQ ID NO: 32          moltype = AA  length = 336
FEATURE                Location/Qualifiers
REGION                 1..336
                       note = KRED-NADH-102 variant
source                 1..336
                       mol_type = protein
                       organism = synthetic construct
SEQUENCE: 32
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFHDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 33          moltype = DNA  length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 33
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gctgcggtgg ttgcaaatac   300
tgccgtggtg ctatcgacaa cgtttgcaaa aacgctttcg gtgactggtt cggtctgggt   360
tatgatggtg gctatcaaca ataccttgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgattgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttcgaaggt cgtgttgttt caaccccgta a              1011

SEQ ID NO: 34          moltype = AA  length = 336
FEATURE                Location/Qualifiers
REGION                 1..336
                       note = KRED-NADH-102 variant
source                 1..336
                       mol_type = protein
                       organism = synthetic construct
SEQUENCE: 34
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LIDLALREIR ILGSFWGTTN DLDDVLKLVS   300
EGKVKPVVRS AKLKELPEYI EKLRNNAYEG RVVFNP                             336

SEQ ID NO: 35          moltype = DNA  length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 35
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggackk yggtgacaac   180
tacgttatgg gtcacgaaat cgctggtacc gttgctgctg ttggtgatga cgttatcaac   240
```

```
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca atacctgctg gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctaccct tcgacgtttg ccagaaatac gttgaaccga aagtgttat catgccggtt  780
ggtctgggtg ctccgaacct gtcttttaac ctgggtgacc tggctctgcg tgaaatccgt  840
atcctgggtt ctttcyrrgg taccaccaac gacctggacg acgttctgaa actggtttct  900
gaaggtaaag ttaaaccggt tgtacgttct gctaaactga agaactgcc ggaatacatc  960
gaaaaactgc gtaacaacgc ttcgaaggt cgtgttgttt tcaacccgta a            1011

SEQ ID NO: 36              moltype = AA   length = 336
FEATURE                    Location/Qualifiers
SITE                       286
                           note = unsure - KRED-NADH-102 variant, Xaa = Phe, Cys, Gly,
                           Val, Xaa = Gln, Ter, Trp, Arg
source                     1..336
                           mol_type = protein
                           organism = synthetic construct
SEQUENCE: 36
MSIPSSQYGF VFNKQSGLKL RNDLPVHKPK AGQLLLKVDA VGLCHSDLHV IYEGLDXGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFXGTTN DLDDVLKLVS   300
EGKVKPVVRS AKLKELPEYI EKLRNNAYEG RVVFNP                             336

SEQ ID NO: 37              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 37
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctaccct tcgacgtttg ccagaaatac gttgaaccga aagtgttat catgccggtt   780
ggtctgggtg ctccgaacct gtcttttaac ctgtgggacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttcgaaggt cgtgttgttt tcaacccgta a            1011

SEQ ID NO: 38              moltype = AA   length = 336
FEATURE                    Location/Qualifiers
REGION                     1..336
                           note = KRED-NADH-102 variant
source                     1..336
                           mol_type = protein
                           organism = synthetic construct
SEQUENCE: 38
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LWDLALREIR ILGSFWGTTN DLDDVLKLVS   300
EGKVKPVVRS AKLKELPEYI EKLRNNAYEG RVVFNP                             336

SEQ ID NO: 39              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 39
```

```
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccTgctg gtaactcgcc gcgtaacct gtctcgtatc    420
ccggataaca tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgcatg ctccgaacct gtcttttaac ctgggtgacc tggctctgcg tgaaatccgt   840
atcctgggtt ctttctgggg taccaccaac gacctggacg acgttctgaa actggttttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011

SEQ ID NO: 42           moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 42
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLHAPNLSFN LGDLALREIR ILGSFWGTTN DLDDVLKLVS   300
EGKVKPVVRS AKLKELPEYI EKLRNNAYEG RVVFNP                            336

SEQ ID NO: 43           moltype = DNA  length = 1011
FEATURE                 Location/Qualifiers
misc_feature            1..1011
                        note = KRED-NADH-102 variant
source                  1..1011
```

```
                    mol_type = other DNA
                    organism = synthetic construct
SEQUENCE: 43
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccgttctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct cgacgtttg ccagaaatac gttgaaccga aggtgttat catgccggtt      780
ggtctggtg ctccgaacct gtcttttaac ctgggtgacc tggctctgcg tgaaatccgt     840
atcctgggtt cttttctgggg taccaccaac gacctggacg acgttctgaa actggtttct    900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011

SEQ ID NO: 44        moltype = AA length = 336
FEATURE              Location/Qualifiers
REGION               1..336
                     note = KRED-NADH-102 variant
source               1..336
                     mol_type = protein
                     organism = synthetic construct
SEQUENCE: 44
MSIPSSQYGF VFNKQSGLKL RNDLPVHKPK AGQLLLKVDA VGLCRSDLHV IYEGLDCGDN    60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLALREIR ILGSFWGTTN DLDDVLKLVS    300
EGKVKPVVRS AKLKELPEYI EKLRNNAYEG RVVFNP                              336

SEQ ID NO: 45        moltype = DNA length = 1011
FEATURE              Location/Qualifiers
misc_feature         1..1011
                     note = KRED-NADH-102 variant
source               1..1011
                     mol_type = other DNA
                     organism = synthetic construct
SEQUENCE: 45
atgtctatcc cgtcttctca gtatggtttc gtatttaaca acagtctgg tctgaaactg      60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct cgacgtttg ccagaaatac gttgaaccga aggtgttat catgccggtt      780
ggtctggtg ctccgaacct gatgtttaac ctgggtgacc tggctctgcg tgaaatccgt     840
atcctgggtt cttttctgggg taccaccaac gacctggacg acgttctgaa actggtttct    900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011

SEQ ID NO: 46        moltype = AA length = 336
FEATURE              Location/Qualifiers
REGION               1..336
                     note = KRED-NADH-102 variant
source               1..336
                     mol_type = protein
                     organism = synthetic construct
SEQUENCE: 46
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLMFN LGDLALREIR ILGSFWGTTN DLDDVLKLVS    300
EGKVKPVVRS AKLKELPEYI EKLRNNAYEG RVVFNP                              336

SEQ ID NO: 47        moltype = DNA length = 1011
FEATURE              Location/Qualifiers
```

-continued

```
misc_feature            1..1011
                        note = KRED-NADH-102 variant
source                  1..1011
                        mol_type = other DNA
                        organism = synthetic construct
SEQUENCE: 47
atgtctatcc cgtcttctca gtatggtttc gtatttaaca acagtctggt ctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctggtg ctccgaacct gtggtttaac ctgggtgacc tggctctgcg tgaaatccgt   840
atcctggtt cttctggggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 48           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 48
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLWFN LGDLALREIR ILGSFWGTTN DLDDVLKLVS   300
EGKVKPVVRS AKLKELPEYI EKLRNNAYEG RVVFNP                             336

SEQ ID NO: 49           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 49
atgtctatcc cgtcttctca gtatggtttc gtatttaaca acagtctggt ctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctggtg ctccgaacct gtctttaac ctgggtgacg ttgctctgcg tgaaatccgt   840
atcctggtt cttctggggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 50           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 50
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDVALREIR ILGSFWGTTN DLDDVLKLVS   300
EGKVKPVVRS AKLKELPEYI EKLRNNAYEG RVVFNP                             336
```

```
SEQ ID NO: 51           moltype = DNA  length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 51
atgtctatcc cgtcttctca gtatggtttc gtatttaaca aacagtctgg tctgaaactg    60
cgcaacgatc tgccagtaca caagcccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaaattg gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtt actatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct cgacgtttgc cagaaatacg ttgaaccgaa aggtgtattc atgccgttg   780
ggtctgggtg ctccgaacct gtcttttaac ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 52           moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 52
MSIPSSQYGF VFNKQSGLKL RNDLPVHKPK AGQLLLKVDA VGLCHSDLHV IYEGLDCGDN    60
YVMGHEIAGT VAAVGDDVIN YKIGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 53           moltype = DNA  length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 53
atgtctatcc cgtcttctca gtatggtttc gtatttaaca aacagtctgg tctgaaactg    60
cgcaacgatc tgccagtaca caagcccgaaa gctggtcaac tgctgctgaa agtagatgca   120
gtaggtctgt gccactctga tctgcacgtt atcgatgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtt actatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct cgacgtttgc cagaaatacg ttgaaccgaa aggtgttat catgccggtt    780
ggtctgggtg ctccgaacct gtcttttaac ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 54           moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 54
MSIPSSQYGF VFNKQSGLKL RNDLPVHKPK AGQLLLKVDA VGLCHSDLHV IDEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
```

```
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLALRERR ILGSFWGTTN DLDDVLKLVS    300
EGKVKPVVRS AKLKELPEYI EKLRNNAYEG RVVFNP                              336

SEQ ID NO: 55             moltype = DNA   length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 55
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccteftctga gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct cgacgtttg ccagaaatac gttgaaccga aagtgttat catgccggtt       780
ggtctgggtg ctccgaacct gtcttttaac ctgggtgacc tggctctgcg tgaaaggcgt    840
atcctgggtt ctttctgggg taccaccaac gacctggacg acgttctgaa actggttctt    900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011

SEQ ID NO: 56             moltype = AA   length = 336
FEATURE                   Location/Qualifiers
REGION                    1..336
                          note = KRED-NADH-102 variant
source                    1..336
                          mol_type = protein
                          organism = synthetic construct
SEQUENCE: 56
MSIPSSQYGF VFNKQSGLKL RNDLPVHKPK AGQLLLKVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLALRERR ILGSFWGTTN DLDDVLKLVS    300
EGKVKPVVRS AKLKELPEYI EKLRNNAYEG RVVFNP                              336

SEQ ID NO: 57             moltype = DNA   length = 1011
FEATURE                   Location/Qualifiers
misc_feature              1..1011
                          note = KRED-NADH-102 variant
source                    1..1011
                          mol_type = other DNA
                          organism = synthetic construct
SEQUENCE: 57
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atcagtgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca ataccteftctga gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct cgacgtttg ccagaaatac gttgaaccga aagtgttat catgccggtt       780
ggtctgggtg ctccgaacct gtcttttaac ctgggtgacc tggctctgcg tgaaatccgt    840
atcctgggtt ctttctgggg taccaccaac gacctggacg acgttctgaa actggttctt    900
gaaggtaaag ttaaaccggt tgtacgttct gctaaactga agaactgcc ggaatacatc      960
gaaaaactgc gtaacaacgc ttacgaaggt cgtgttgttt tcaacccgta a             1011

SEQ ID NO: 58             moltype = AA   length = 336
FEATURE                   Location/Qualifiers
REGION                    1..336
                          note = KRED-NADH-102 variant
source                    1..336
                          mol_type = protein
                          organism = synthetic construct
SEQUENCE: 58
```

```
MSIPSSQYGF VFNKQSGLKL RNDLPVHKPK AGQLLLKVDA VGLCHSDLHV ISEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 59           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 59
atgtctatcc cgtcttctca gtatggtttc gtatttaaca acagtctgg tctgaaactg     60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaacaacgt   840
atcctgggtt cttctggggg taccaccaac gacctggacg acgttctgaa actgtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a            1011

SEQ ID NO: 60           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 60
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREQR ILGSFWGTTN DLDDVLKLVS   300
EGKVKPVVRS AKLKELPEYI EKLRNNAYEG RVVFNP                             336

SEQ ID NO: 61           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 61
atgtctatcc cgtcttctca gtatggtttc gtatttaaca acagtctgg tctgaaactg     60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgaca ttgctctgcg tgaaatccgt   840
atcctgggtt cttctggggg taccaccaac gacctggacg acgttctgaa actgtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a            1011

SEQ ID NO: 62           moltype = AA   length = 336
FEATURE                 Location/Qualifiers
REGION                  1..336
                        note = KRED-NADH-102 variant
source                  1..336
```

```
                        mol_type = protein
                        organism = synthetic construct
SEQUENCE: 62
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDIALREIR ILGSFWGTTN DLDDVLKLVS   300
EGKVKPVVRS AKLKELPEYI EKLRNNAYEG RVVFNP                             336

SEQ ID NO: 63           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 63
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctgctttg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctggtg ctccgaacct gtctttaac ctgggtgacc tggctctgcg tgaaatccgt   840
atcctgggtt ctttctggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 64           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 64
MSIPSSQYGF VFNKQSGLKL RNDLPVHKPK AGQLLLKVDA VGLCHSDLHV IYEGLLCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDIALREIR ILGSFWGTTN DLDDVLKLVS   300
EGKVKPVVRS AKLKELPEYI EKLRNNAYEG RVVFNP                             336

SEQ ID NO: 65           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 65
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaca aacgctttcg gtgactggtt cggtctgggt   360
tatgatggtg gctatcaaca ataccgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaaatccgt   840
atcctgggtt ctttctgggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 66           moltype = AA   length = 336
FEATURE                 Location/Qualifiers
```

```
REGION                      1..336
                            note = KRED-NADH-102 variant
source                      1..336
                            mol_type = protein
                            organism = synthetic construct
SEQUENCE: 66
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCT NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                           336

SEQ ID NO: 67               moltype = DNA  length = 1011
FEATURE                     Location/Qualifiers
misc_feature                1..1011
                            note = KRED-NADH-102 variant
source                      1..1011
                            mol_type = other DNA
                            organism = synthetic construct
SEQUENCE: 67
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tagtggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaaatccgt   840
atcctgggtt ctttctgggg taccaccaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011

SEQ ID NO: 68               moltype = AA  length = 336
FEATURE                     Location/Qualifiers
REGION                      1..336
                            note = KRED-NADH-102 variant
source                      1..336
                            mol_type = protein
                            organism = synthetic construct
SEQUENCE: 68
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISSGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                           336

SEQ ID NO: 69               moltype = DNA  length = 1011
FEATURE                     Location/Qualifiers
misc_feature                1..1011
                            note = KRED-NADH-102 variant
source                      1..1011
                            mol_type = other DNA
                            organism = synthetic construct
SEQUENCE: 69
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ccatcgacaa cgtttgcaaa aacgctttcg gtgactggtt cggtctgggt   360
tatgatggtg gctatcaaca atacctgctg gtaactcgcc cgcgtaacct gtctccgtatc   420
ccggataacg tatcttcgga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat cgtgccggtt   780
ggtctgggtg ctccgaacct gtcttttaac ctgggtgacc tggctctgcg tgaaatccgt   840
atcctgggtt ctttctgggg taccagcaac gacctggacg acgttctgaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011
```

```
SEQ ID NO: 70            moltype = AA   length = 336
FEATURE                  Location/Qualifiers
REGION                   1..336
                         note = KRED-NADH-102 variant
source                   1..336
                         mol_type = protein
                         organism = synthetic construct
SEQUENCE: 70
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLVRI PDNVSSDVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIVPV GLGAPNLSFN LGDLALREIR ILGSFWGTSN DLDDVLKLVS  300
EGKVKPVVRS AKLKELPEYI EKLRNNAYEG RVVFNP                           336

SEQ ID NO: 71            moltype = DNA   length = 1011
FEATURE                  Location/Qualifiers
misc_feature             1..1011
                         note = KRED-NADH-102 variant
source                   1..1011
                         mol_type = other DNA
                         organism = synthetic construct
SEQUENCE: 71
atgtcgatcc cgtcttctca gtatggtttc gtatttaaca acagtctgg tctgaaactg    60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactgttg cggtctgggt  360
tatgatggtg gctatcaaca ataccrgctga gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct cgacgtttg ccagaaatac gttgaaccga aaggtgttat catgccggtt  780
ggtctggtgt ctccgaacct gtcttttaac ctgggtgacc tggctctgcg tgaaatccgt  840
atcctgggtt ctttctgggg taccaccaac gacctggacg acgttctgaa actggtttct  900
gaaggtaaag ttaaaccggt tgtacgttcc gctaaactga agaactgcc ggaatacatc   960
gaaaaactgc gtaacaacgc ttacgaaggt cgtgttgttt tcaacccgta a           1011

SEQ ID NO: 72            moltype = AA   length = 336
FEATURE                  Location/Qualifiers
REGION                   1..336
                         note = KRED-NADH-102 variant
source                   1..336
                         mol_type = protein
                         organism = synthetic construct
SEQUENCE: 72
MSIPSSQYGF VFNKQSGLKL RNDLPVHKPK AGQLLLKVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA RKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                           336

SEQ ID NO: 73            moltype = DNA   length = 1011
FEATURE                  Location/Qualifiers
misc_feature             1..1011
                         note = KRED-NADH-102 variant
source                   1..1011
                         mol_type = other DNA
                         organism = synthetic construct
SEQUENCE: 73
atgtcgatcc cgtcttctca gtatggtttc gtatttaaca acagtctgg tctgaaactg    60
cgcaacgatc tgccagtaca caagccgaaa gctggtcaac tgctgctgag agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgatggtg gctatcaaca ataccrgctga gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct aaaaaactgg gtgctgacgc tgtttacgaa  660
accctgccgg aatctatctc tccgggttct ttctctgctt gcttcgactt cgtttctgtt  720
caggctacct cgacgtttg ccagaaatac gttgaaccga aaggtgttat catgccggtt  780
ggtctggtgt ctccgaacct gtcttttaac ctgggtgacc tggctctgcg tgaaatccgt  840
```

```
atcctgggtt ctttctgggg taccaccaac gacctggacg acgttctgaa actggtttct  900
gaaggtaaag ttaaaccggt tgtacgttct gctaaactga agaactgcc ggaatacatc  960
gaaaaactgc gtaacaacgc ttacgaaggt cgtgttgttt tcaacccgta a          1011

SEQ ID NO: 74           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 74
MSIPSSQYGF VFNKQSGLKL RNDLPVHKPK AGQLLLRVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA KKLGADAVYE TLPESISPGS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                            336

SEQ ID NO: 75           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 75
atgtctatcc cgtcttctca gtatggtttc gtatttaaca acagtctgg tctgaaactg    60
cgcaacgatc tgccagtaca caagccgaaa gctggtcaac tgctgctgag agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgacggtg gctatcaaca atacctgctg gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct agaaaactgg gtgctgacgc tgtttacgaa  660
accctgccgg aatctatctc tccgcgttct ttctctgactt gcttcgactt cgtttctgtt  720
caggctacct tcgacgtttg ccagaaatac gttgaaccga aaggtgttat catgccggtt  780
ggtctgggtg ctccgaacct gtcttttaac ctgggtgacc tggctctgcg tgaaatccgt  840
atcctgggtt ctttctgggg taccaccaac gacctggacg acgttctgaa actggtttct  900
gaaggtaaag ttaaaccggt tgtacgttct gctaaactga agaactgcc ggaatacatc  960
gaaaaactgc gtaacaacgc ttacgaaggt cgtgttgttt tcaacccgta a          1011

SEQ ID NO: 76           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 76
MSIPSSQYGF VFNKQSGLKL RNDLPVHKPK AGQLLLRVDA VGLCHSDLHV IYEGLDCGDN   60
YVMGHEIAGT VAAVGDDVIN YKVGDRVACV GPNGCGGCKY CRGAIDNVCK NAFGDWFGLG  120
YDGGYQQYLL VTRPRNLSRI PDNVSADVAA ASTDAVLTPY HAIKMAQVSP TSNILLIGAG  180
GLGGNAIQVA KAFGAKVTVL DKKKEARDQA RKLGADAVYE TLPESISPRS FSACFDFVSV  240
QATFDVCQKY VEPKGVIMPV GLGAPNLSFN LGDLALREIR ILGSFWGTTN DLDDVLKLVS  300
EGKVKPVVRS AKLKELPEYI EKLRNNAYEG RVVFNP                            336

SEQ ID NO: 77           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 77
atgtcgatcc cgtcttctca gtatggtttc gtatttaaca acagtctgg tctgaaactg    60
cgcaacgatc tgccagtaca caagccgaaa gctggtcaac tgctgctgaa agtagatgca  120
gtaggtctgt gccactctga tctgcacgtt atctacgaag gcctggactg cggtgacaac  180
tacgttatgg gtcacgaaat cgctggtacc gttgctgctg ttggtgatga cgttatcaac  240
tacaaagtag gtgaccgtgt agcttgtgtt ggtccgaacg gttgcggtgg ttgcaaatac  300
tgccgtggtg ctatcgacaa cgtttgcaaa aacgctttcg gtgactggtt cggtctgggt  360
tatgacggtg gctatcaaca atacctgctg gtaactcgcc cgcgtaacct gtctcgtatc  420
ccggataacg tatctgctga tgttgctgct gcttctaccg acgctgttct gactccgtac  480
cacgctatca aaatggctca ggtttctccg acctctaaca tcctgctgat cggtgctggt  540
ggtctgggtg gtaacgctat ccaggttgct aaagcattcg gtgctaaagt taccgttctg  600
gacaaaaaaa aagaagctcg tgaccaggct agaaaactgg gtgctgacgc tgtttacgaa  660
```

```
acccrgccgg aatctatctc tccgcgttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaaatccgt   840
atcctggggtt ctttctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a            1011

SEQ ID NO: 78           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 78
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA RKLGADAVYE TLPESISPRS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 79           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 79
atgtcgatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctgctgat cggtgctggt             540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
acccgtgccgg aatctatctc tccgcgttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgggtgacc tggctctgcg tgaaatccgt   840
atcctggggtt ctttctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a            1011

SEQ ID NO: 80           moltype = AA   length = 336
FEATURE                 Location/Qualifiers
REGION                  1..336
                        note = KRED-NADH-102 variant
source                  1..336
                        mol_type = protein
                        organism = synthetic construct
SEQUENCE: 80
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPRS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 81           moltype = DNA   length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 81
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gccggactg cggtgacaac    180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgacggtg gctatcaaca ataccctgctg gtaactcgcc cgcgtaacct gtctcgtatc   420
ccggataacg tatctgctga tgttgctgct gcttctaccg acgctgttct gactccgtac   480
```

```
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgcgttct ttctctgctt gcttcgactt cgtttctgtt    720
caggctacct tcgacgtttg ccagaaatac gttgaaccga aaggtgttat catgccggtt    780
ggtctgggtg ctccgaacct gtcttttaac ctggggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a             1011

SEQ ID NO: 82              moltype = AA   length = 336
FEATURE                    Location/Qualifiers
REGION                     1..336
                           note = KRED-NADH-102 variant
source                     1..336
                           mol_type = protein
                           organism = synthetic construct
SEQUENCE: 82
MSIPSSQYGF VFNKQSGLKL RNDLPVHKPK AGQLLLRVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPRS FSACFDFVSV    240
QATFDVCQKY VEPKGVIMPV GLGAPNLSFN LGDLALREIR ILGSFWGTTN DLDDVLKLVS    300
EGKVKPVVRS AKLKELPEYI EKLRNNAYEG RVVFNP                              336

SEQ ID NO: 83              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 83
atgtcgatcc cgtcttctca gtatggtttc gtatttaaca aacagtctgg tctgaaactg     60
cgcaacgatc tgccagtaca caagccgaaa gctggtcaac tgctgctgag agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
tgccgtggcg ctatcgacaa cgtttgcaaa aacgctttcg gtgactggtt cggtctgggt    360
tatgatggtg gctatcaaca ataccctgctg gtaactcgcc gcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct agaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aaggtgttat catgccggtt    780
ggtctgggtg ctccgaacct gtcttttaac ctggggtgacc tggctctgcg tgaaatccgt    840
atcctgggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a             1011

SEQ ID NO: 84              moltype = AA   length = 336
FEATURE                    Location/Qualifiers
REGION                     1..336
                           note = KRED-NADH-102 variant
source                     1..336
                           mol_type = protein
                           organism = synthetic construct
SEQUENCE: 84
MSIPSSQYGF VFNKQSGLKL RNDLPVHKPK AGQLLLRVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA RKLGADAVYE TLPESISPGS FSACFDFVSV    240
QATFDVCQKY VEPKGVIMPV GLGAPNLSFN LGDLALREIR ILGSFWGTTN DLDDVLKLVS    300
EGKVKPVVRS AKLKELPEYI EKLRNNAYEG RVVFNP                              336

SEQ ID NO: 85              moltype = DNA   length = 1011
FEATURE                    Location/Qualifiers
misc_feature               1..1011
                           note = KRED-NADH-102 variant
source                     1..1011
                           mol_type = other DNA
                           organism = synthetic construct
SEQUENCE: 85
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactg cggtgacaac    180
tacgttatgg gtcacgaaat cgctggtacc gttgctgctg ttggtgatga cgttatcaac    240
tacaaagtag gtgaccgtgt agcttgtgtt ggtccgaacg gttgcggtgg ttgcaaatac    300
```

```
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780
ggtctggtg ctccgaacct gtcttttaac ctgggtgacc tggcgatgcg tgaaatccgt    840
atcctggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 86          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 86
MSIPSSQYGF VFNKQSGLKL RNDLPVHKPK AGQLLLKVDA VGLCHSDLHV IYEGLDCGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLAMREIR ILGSFWGTTN DLDDVLKLVS    300
EGKVKPVVRS AKLKELPEYI EKLRNNAYEG RVVFNP                              336

SEQ ID NO: 87          moltype = DNA   length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 87
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
gtaggtctgt gccactctga tctgcacgtt atctacgaag gcctggactg tggtgacaac    180
tacgttatgg gtcacgaaat cgctggtacc gttgctgctg ttggtgatga cgttaccaac    240
tacaaatccg gtgaccgtgt agcttgtgtt ggtccgaacg gttgcggtgg ttgcaaatac    300
tgccgtggtg ctatcgacaa cgtttgcaaa aacgctttcg gtgactggtt cggtctgggt    360
tatgatggtg gctatcaaca atacctgctg gtaactcgcc cgcgtaacct gtctcgtatc    420
ccggataacg tatctgctga tgttgctgct gcttctaccg acgctgttct gactccgtac    480
cacgctatca aaatggctca ggtttctccg acctctaaca tcctgctgat cggtgctggt    540
ggtctgggtg gtaacgctat ccaggttgct aaagcattcg gtgctaaagt taccgttctg    600
gacaaaaaaa aagaagctcg tgaccaggct aaaaaactgg gtgctgacgc tgtttacgaa    660
accctgccgg aatctatctc tccgggttct ttctctgctt gcttcgactt cgtttctgtt    720
caggctacct tcgacgtttg ccagaaatac gttgaaccga aggtgttat catgccggtt    780
ggtctggtg ctccgaacct gtcttttaac ctgggtgacc tgaacatgcg tgaaatccgt    840
atcctggtt ctttctgggg taccaccaac gacctggacg acgttctgaa actggtttct    900
gaaggtaaag ttaaaccggt tgtacgttct gctaaactga agaactgcc ggaatacatc    960
gaaaaactgc gtaacaacgc ttacgaaggt cgtgttgttt tcaacccgta a            1011

SEQ ID NO: 88          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 88
MSIPSSQYGF VFNKQSGLKL RNDLPVHKPK AGQLLLKVDA VGLCHSDLHV IYEGLDCGDN     60
YVMGHEIAGT VAAVGDDVTN YKSGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LGDLNMREIR ILGSFWGTTN DLDDVLKLVS    300
EGKVKPVVRS AKLKELPEYI EKLRNNAYEG RVVFNP                              336

SEQ ID NO: 89          moltype = DNA   length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 89
atgtctatcc cgtcttctca gtatggtttc gtatttaaca aacagtctgg tctgaaactg     60
cgcaacgatc tgccagtaca caagccgaaa gctggtcaac tgctgctgaa agtagatgca    120
```

```
gtaggtctgt gccactctga tctgcacgtt atctacgaag gccttgactg tggtgacaac   180
tacgttatgg gtcacgaaat cgctggtacc gttgctgctg ttggtgatga cgttatcaac   240
tacaaatccg gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccgctgt gtaactcgcc cgcgtaacct gtctcgtatc   420
ccggataacg tatctgctga tgttgctgct gcttctaccg acgctgttct gactccgtac   480
cacgctatca aatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgttctgtt   720
caggctacct tcgacgtttg ccagaaatac gttgaaccga aaggtgttat catgccggtt   780
ggtctgggtg ctccgaacct gtcttttaac ctgggtgacc tgaacatgcg tgaaatccgt   840
atcctgggtt ctttctgggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta  a          1011

SEQ ID NO: 90               moltype = AA length = 336
FEATURE                     Location/Qualifiers
REGION                      1..336
                            note = KRED-NADH-102 variant
source                      1..336
                            mol_type = protein
                            organism = synthetic construct
SEQUENCE: 90
MSIPSSQYGF VFNKQSGLKL RNDLPVHKPK AGQLLLKVDA VGLCHSDLHV IYEGLDCGDN    60
YVMGHEIAGT VAAVGDDVIN YKSGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLNMREIR ILGSFWGTTN DLDDVLKLVS   300
EGKVKPVVRS AKLKELPEYI EKLRNNAYEG RVVFNP                             336

SEQ ID NO: 91               moltype = DNA length = 1011
FEATURE                     Location/Qualifiers
misc_feature                1..1011
                            note = KRED-NADH-102 variant
source                      1..1011
                            mol_type = other DNA
                            organism = synthetic construct
SEQUENCE: 91
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaatccg gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca ataccgctgt gtaactcgcc cgcgtaacct gtctcgtatc   420
ccggataacg tatctgctga tgttgctgct gcttctaccg acgctgttct gactccgtac   480
cacgctatca aatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgttctgtt   720
caggctacct tcgacgtttg ccagaaatac gttgaaccga aaggtgttat catgccggtt   780
ggtctgggtg ctccgaacct gtcttttaac ctgggtgacc tggcgatgcg tgaaatccgt   840
atcctgggtt ctttctgggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta  a          1011

SEQ ID NO: 92               moltype = AA length = 336
FEATURE                     Location/Qualifiers
REGION                      1..336
                            note = KRED-NADH-102 variant
source                      1..336
                            mol_type = protein
                            organism = synthetic construct
SEQUENCE: 92
MSIPSSQYGF VFNKQSGLKL RNDLPVHKPK AGQLLLKVDA VGLCHSDLHV IYEGLDCGDN    60
YVMGHEIAGT VAAVGDDVIN YKSGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLAMREIR ILGSFWGTTN DLDDVLKLVS   300
EGKVKPVVRS AKLKELPEYI EKLRNNAYEG RVVFNP                             336

SEQ ID NO: 93               moltype = DNA length = 1011
FEATURE                     Location/Qualifiers
misc_feature                1..1011
                            note = KRED-NADH-102 variant
source                      1..1011
                            mol_type = other DNA
                            organism = synthetic construct
```

```
SEQUENCE: 93
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccattctga tctgcacgtt atctacgaag gcctggactg tggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
acccctgccgg aatctatctc tccgggttct ttctctgctt gcttcgactt cgtttctgtt   720
caggctacct tcgacgtttg ccagaaatac gttgaaccga aagtgttat catgccggtt   780
ggtctgggtg ctccgaacct gtcttttaac ctgggtgacc tgaatatgcg tgaaatccgt   840
atcctgggtt ctttctgggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 94          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 94
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLNMREIR ILGSFWGTTN DLDDVLKLVS   300
EGKVKPVVRS AKLKELPEYI EKLRNNAYEG RVVFNP                             336

SEQ ID NO: 95          moltype = DNA   length = 1011
FEATURE                Location/Qualifiers
misc_feature           1..1011
                       note = KRED-NADH-102 variant
source                 1..1011
                       mol_type = other DNA
                       organism = synthetic construct
SEQUENCE: 95
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag ctttgacgc gggtgacaac   180
tacgttatgg gtcacgaaat cgctggtacc gttgctgctg ttggtgatga cgttatcaac   240
tacaaagttg gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
acccctgccgg aatctatctc tccgggttct ttctctgctt gcttcgactt cgtttctgtt   720
caggctacct tcgacgtttg ccagaaatac gttgaaccga aagtgttat catgccggtt   780
ggtctgggtg ctccgaacct gtcttttaac ctgggtgacc tggcgatgcg tgaaatccgt   840
atcctgggtt ctttctgggg taccaccaac gacctggacg acgttctgaa actggttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 96          moltype = AA   length = 336
FEATURE                Location/Qualifiers
REGION                 1..336
                       note = KRED-NADH-102 variant
source                 1..336
                       mol_type = protein
                       organism = synthetic construct
SEQUENCE: 96
MSIPSSQYGF VFNKQSGLKL RNDLPVHKPK AGQLLLKVDA VGLCHSDLHV IYEGFDAGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLAMREIR ILGSFWGTTN DLDDVLKLVS   300
EGKVKPVVRS AKLKELPEYI EKLRNNAYEG RVVFNP                             336

SEQ ID NO: 97          moltype = DNA   length = 1011
FEATURE                Location/Qualifiers
misc_feature           1..1011
                       note = KRED-NADH-102 variant
```

```
source                  1..1011
                        mol_type = other DNA
                        organism = synthetic construct
SEQUENCE: 97
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctacgaag gcctggactg cggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg gcatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aagttgttat catgccggtt   780
ggtctgggtg ctccgaacct gtcttttaac ctgggtgacc tggctctgcg tgaaatccgt   840
atcctgggtt ctttctgggg taccaccaac gacctggacg acgttctgaa actggttttct  900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011

SEQ ID NO: 98           moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 98
MSIPSSQYGF VFNKQSGLKL RNDLPVHKPK AGQLLLKVDA VGLCHSDLHV IYEGLDCGDN    60
YVMGHEIAGT VAAVGDDVIN YKVGDRVACV GPNGCGGCKY CRGGIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 99           moltype = DNA  length = 1011
FEATURE                 Location/Qualifiers
misc_feature            1..1011
                        note = KRED-NADH-102 variant
source                  1..1011
                        mol_type = other DNA
                        organism = synthetic construct
SEQUENCE: 99
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccattctga tctgcacgtt atctacgaag gcctggacat aggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg gcatcgacaa cgtttgcaaa aacgctttcc atgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aagttgttat catgccggtt   780
ggtctgggcg ctccgaacct gtcttttaac ctgggtgacc tggctctgcg tgaaatccgt   840
atcctgggtt ctttctgggg taccaccaac gacctggacg acgttctgaa actggttttct  900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011

SEQ ID NO: 100          moltype = AA  length = 336
FEATURE                 Location/Qualifiers
REGION                  1..336
                        note = KRED-NADH-102 variant
source                  1..336
                        mol_type = protein
                        organism = synthetic construct
SEQUENCE: 100
MSIPSSQYGF VFNKQSGLKL RNDLPVHKPK AGQLLLKVDA VGLCHSDLHV IYEGLDIGDN    60
YVMGHEIAGT VAAVGDDVIN YKVGDRVACV GPNGCGGCKY CRGGIDNVCK NAFHDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336

SEQ ID NO: 101          moltype = DNA  length = 1011
```

| FEATURE | Location/Qualifiers |
|---|---|
| misc_feature | 1..1011 |
| | note = KRED-NADH-102 variant |
| source | 1..1011 |
| | mol_type = other DNA |
| | organism = synthetic construct |

SEQUENCE: 101
```
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccattctga tctgcacgtt atctcgacgt ggctggactt aggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg gcatcgacaa cgtttgcaaa aacgctttcc atgactggtt cggtctgggt   360
tatgatggtg gctatcaaca atacctgctg taactcgcg cgcgtaacct gtctcgtatc   420
ccggataacg tatctgctga tgttgctgct gcttctaccg acgctgttct gactccgtac   480
cacgctatca aatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgcgttct ttctctgctt gcttcgactt cgtttctgtt   720
caggctacct tcgacgtttg ccagaaatac gttgaaccga aaggtgttat catgccggtt   780
ggtctgggcg ctccgaacct gtctttaac ctgggtgacc tggcgttgcg tgaaatccgt   840
atcctgggtt cttctctgggg taccaccaac gacctggacg acgttctgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011
```

| SEQ ID NO: 102 | moltype = AA length = 336 |
|---|---|
| FEATURE | Location/Qualifiers |
| REGION | 1..336 |
| | note = KRED-NADH-102 variant |
| source | 1..336 |
| | mol_type = protein |
| | organism = synthetic construct |

SEQUENCE: 102
```
MSIPSSQYGF VFNKQSGLKL RNDLPVHKPK AGQLLLKVDA VGLCHSDLHV IYEGLDLGDN    60
YVMGHEIAGT VAAVGDDVIN YKVGDRVACV GPNGCGGCKY CRGGIDNVCK NAFHDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPRS FSACFDFVSV   240
QATFDVCQKY VEPKGVIMPV GLGAPNLSFN LGDLALREIR ILGSFWGTTN DLDDVLKLVS   300
EGKVKPVVRS AKLKELPEYI EKLRNNAYEG RVVFNP                             336
```

| SEQ ID NO: 103 | moltype = DNA length = 1011 |
|---|---|
| FEATURE | Location/Qualifiers |
| misc_feature | 1..1011 |
| | note = KRED-NADH-102 variant |
| source | 1..1011 |
| | mol_type = other DNA |
| | organism = synthetic construct |

SEQUENCE: 103
```
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctcagcgt ggctgggtt gggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg gctatcgaca acgtttgcaaa aacgctttcg tgactggtt cggtctgggt   360
tatgatggtg gctatcaaca atacctgctg taactcgcg cgcgtaacct gtctcgtatc   420
ccggataacg tatctgctga tgttgctgct gcttctaccg acgctgttct gactccgtac   480
cacgctatca aatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtctttaac ctgcatgacc ttgctctgcg tgaacaccgt   840
atcctgggtt cttctctgggg taccaccaac gacctggacg acgttttaa actggttct    900
gaaggtaaag ttaaaccggt tgtacgatct gctaaactga agaactgcc ggaatacatc   960
gaaaaactgc gtaacaacgc ttacgaaggt cgtgttgttt tcaacccgta a           1011
```

| SEQ ID NO: 104 | moltype = AA length = 336 |
|---|---|
| FEATURE | Location/Qualifiers |
| REGION | 1..336 |
| | note = KRED-NADH-102 variant |
| source | 1..336 |
| | mol_type = protein |
| | organism = synthetic construct |

SEQUENCE: 104
```
MSIPSSQYGF VFNKQSGLKL RNDLPVHKPK AGQLLLKVDA VGLCHSDLHV ISEGLDLGDN    60
YVMGHEIAGT VAAVGDDVIN YKVGDRVACV GPNGCGGCKY CRGAIDNVCK NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LHDLALREHR ILGSFWGTTN DLDDVFKLVS   300
```

EGKVKPVVRS AKLKELPEYI EKLRNNAYEG RVVFNP                                336

SEQ ID NO: 105              moltype = DNA   length = 1011
FEATURE                     Location/Qualifiers
misc_feature                1..1011
                            note = KRED-NADH-102 variant
source                      1..1011
                            mol_type = other DNA
                            organism = synthetic construct
SEQUENCE: 105
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atcgatgaag gcctggattt gggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtctttaac ctgcatgacc ttgctctgcg tgaaatacgt   840
atcctggttt ctttctgggg taccaccaac gacctggacg acgttttgaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 106              moltype = AA   length = 336
FEATURE                     Location/Qualifiers
REGION                      1..336
                            note = KRED-NADH-102 variant
source                      1..336
                            mol_type = protein
                            organism = synthetic construct
SEQUENCE: 106
MSIPSSQYGF VFNKQSGLKL RNDLPVHKPK AGQLLLKVDA VGLCHSDLHV IDEGLDLGDN     60
YVMGHEIAGT VAAVGDDVIN YKVGDRVACV GPNGCGGCKY CRGAIDNVCK NAFGDWFGLG    120
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LHDLALREIR ILGSFWGTTN DLDDVLKLVS    300
EGKVKPVVRS AKLKELPEYI EKLRNNAYEG RVVFNP                              336

SEQ ID NO: 107              moltype = DNA   length = 1011
FEATURE                     Location/Qualifiers
misc_feature                1..1011
                            note = KRED-NADH-102 variant
source                      1..1011
                            mol_type = other DNA
                            organism = synthetic construct
SEQUENCE: 107
atgtctatcc cgtcttctca gtatggtttc gtatttaaca aacagtctgg tctgaaactg    60
cgcaacgatc tgccagtaca caagccgaaa gctggtcaac tgctgctgaa agtagatgca   120
gtaggtctgt gccactctga tctgcacgtt atctcagaag gcctggattt gggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaaa aacgctttcg gtgactggtt cggtctgggt   360
tatgatggtg gctatcaaca atacctgctg gtaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
accctgccgg aatctatctc tccgggttct ttctctgctt gcttcgactt cgtttctgtt   720
caggctacct tcgacgtttg ccagaaatac gttgaaccga aaggtgttat catgccggtt   780
ggtctgggtg ctccgaacct gtcttttaac ctgcatgacg ttgctctgcg tgaacaccgt   840
atcctggttt ctttctgggg taccaccaac gacctggacg acgttttcaa actggtttct   900
gaaggtaaag ttaaaccggt tgtacgttct gctaaactga agaactgcc ggaatacatc   960
gaaaaactgc gtaacaacgc ttacgaaggt cgtgttgttt tcaacccgta a           1011

SEQ ID NO: 108              moltype = AA   length = 336
FEATURE                     Location/Qualifiers
REGION                      1..336
                            note = KRED-NADH-102 variant
source                      1..336
                            mol_type = protein
                            organism = synthetic construct
SEQUENCE: 108
MSIPSSQYGF VFNKQSGLKL RNDLPVHKPK AGQLLLKVDA VGLCHSDLHV ISEGLDLGDN     60
YVMGHEIAGT VAAVGDDVIN YKVGDRVACV GPNGCGGCKY CRGAIDNVCK NAFGDWFGLG    120

```
YDGGYQQYLL VTRPRNLSRI PDNVSADVAA ASTDAVLTPY HAIKMAQVSP TSNILLIGAG    180
GLGGNAIQVA KAFGAKVTVL DKKKEARDQA KKLGADAVYE TLPESISPGS FSACFDFVSV    240
QATFDVCQKY VEPKGVIMPV GLGAPNLSFN LHDVALREHR ILGSFWGTTN DLDDVFKLVS    300
EGKVKPVVRS AKLKELPEYI EKLRNNAYEG RVVFNP                              336

SEQ ID NO: 109           moltype = DNA  length = 1011
FEATURE                  Location/Qualifiers
misc_feature             1..1011
                         note = KRED-NADH-102 variant
source                   1..1011
                         mol_type = other DNA
                         organism = synthetic construct
SEQUENCE: 109
atgtctatcc cgtcttctca gtatggtttc gtatttaaca aacagtctgg tctgaaactg      60
cgcaacgatc tgccagtaca caagcccgaaa gctggtcaac tgctgctgaa agtagatgca   120
gtaggtctgt gccactctga tctgcacgtt atctcagaag gcctggattt gggtgacaac   180
tacgttatgg gtcacgaaat cgctggtacc gttgctgctg ttggtgatga cgttatcaac   240
tacaaagtag gtgaccgtgt agcttgtgtt ggtccgaacg gttgcggtgg ttgcaaatac   300
tgccgtggtg ctatcgacaa cgtttgcaca aacgctttcg gtgactggtt cggtctgggt   360
tatgatggtg gctatcaaca ataccgctgg taaactcgcc cgcgtaacct gtctcgtatc   420
ccggataacg tatctgctga tgttgctgct gcttctaccg acgctgttct gactccgtac   480
cacgctatca aaatggctca ggtttctccg acctctaaca tcctgctgat cggtgctggt   540
ggtctgggtg gtaacgctat ccaggttgct aaagcattcg gtgctaaagt taccgttctg   600
gacaaaaaaa aagaagctcg tgaccaggct aaaaaactgg gtgctgacgc tgtttacgaa   660
acccctgccg aatctatctc tccgggttct ttctctgctt gcttcgactt cgtttctgtt   720
caggctacct cgacgtttg ccagaaatac gttgaaccga aaggtgttat catgccggtt    780
ggtctgggtg ctccgaacct gtcttttaac ctgcatgacc ttgctctgcg tgaaatccgt   840
atcctgggtt ctttctgggg taccaccaac gacctggacg acgttttcaa actggtttct   900
gaaggtaaag ttaaaccggt tgtacgttct gctaaactga agaactgcc ggaatacatc    960
gaaaaactgc gtaacaacgc ttacgaaggt cgtgttgttt tcaacccgta a           1011

SEQ ID NO: 110           moltype = AA  length = 336
FEATURE                  Location/Qualifiers
REGION                   1..336
                         note = KRED-NADH-102 variant
source                   1..336
                         mol_type = protein
                         organism = synthetic construct
SEQUENCE: 110
MSIPSSQYGF VFNKQSGLKL RNDLPVHKPK AGQLLLKVDA VGLCHSDLHV ISEGLDLGDN     60
YVMGHEIAGT VAAVGDDVIN YKVGDRVACV GPNGCGGCKY CRGAIDNVCT NAFGDWFGLG   120
YDGGYQQYLL VTRPRNLSRI PDNVSADVAA ASTDAVLTPY HAIKMAQVSP TSNILLIGAG   180
GLGGNAIQVA KAFGAKVTVL DKKKEARDQA KKLGADAVYE TLPESISPGS FSACFDFVSV   240
QATFDVCQKY VEPKGVIMPV GLGAPNLSFN LHDLALREIR ILGSFWGTTN DLDDVFKLVS   300
EGKVKPVVRS AKLKELPEYI EKLRNNAYEG RVVFNP                              336

SEQ ID NO: 111           moltype = DNA  length = 1032
FEATURE                  Location/Qualifiers
misc_feature             1..1032
                         note = KRED-101 variant
source                   1..1032
                         mol_type = other DNA
                         organism = synthetic construct
SEQUENCE: 111
atggctaaaa tcgataacgc agttctgccg gaaggttccc tggttctggt taccggtgct     60
aacggtttcg ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttccg ttgtttcctt ctccaacaaa   300
tacgacgaag ttgttacccc ggctatcggt ggtaccttga acgtctctgcg tgctgctgct   360
gctaccccgt ccgttaaacg tttcgttctg acctcctcca ccgtttccgc tctgattccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcatcc   540
aagaccgaag tgaactggc tgcatggaaa tttatgaatg agaacaagcc acacttcact   600
ctgaacgctg tactgccaaa ctacactatt ggcactattt cgatccgga aactcagtac   660
ggttccacct ccgttggat gatgtccctg tttaacggcg aggtttcccc ggctctggct   720
ctgatgccac cgcagtacta cgtttccgct gttgatattg cctgctgca cctgggttgc   780
ctggttctgc cacaaatcga acgtcgtcgt gtttacggta cggctggtac ttttgattgg   840
aacaccgttc tggctccctt ccgtaaactg tacccgtcca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgctt aa                                                       1032

SEQ ID NO: 112           moltype = AA  length = 343
FEATURE                  Location/Qualifiers
REGION                   1..343
                         note = KRED-101 variant
source                   1..343
                         mol_type = protein
```

```
                        organism = synthetic construct
SEQUENCE: 112
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYVSA VDIGLLHLGC LVLPQIERRR VYGTAGTFDW NTVLATFRKL YPSKTFPADF    300
PDQGQDLSKF DTAPSLEILK SLGRPGWRSI EESIKDLVGS ETA                    343

SEQ ID NO: 113          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 113
atggctaaaa tcgataacgc agttctgccg gaaggttccc tggttctggt taccggtgct    60
aacggtttca ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttcc ttgtttcctt ctccaacaaa   300
tacgacgaag ttgttacccc ggctatcggt ggtaccttga acgctctgcg tgctgctgct   360
gctaccccgt ccgttaaacg tttcgttctg acctcctcca ccgtttcggc tctgattccg    420
aaaccgaacg ttgaaggtat ctacctggac gaaaaatcct ggaacctgga atccatcgac    480
aaagctaaaa ccctgccgga atccgacccg cagaaatcc tgtgggtata cgctgcatcc    540
aagaccgaag ctgaactggc tgcatggaaa tttatggatg agaacaagcc acacttcact    600
ctgaacgctg tactgccaaa ctacactatt ggcactattt cgatccgga aactcagggc    660
ggttccacct ccgttggat gatgtccctg tttaacggcg aggtttcccc ggctctggct    720
ctgatgccac cgcagtacta cgtttccgct gttgatattg gctgctgca cgtgggtgca    780
ctggttctgc cacaaatcga acgtcgtcgt gtttacggta cggctggtac tttcgattgg    840
aacaccgttc tggctacctt ccgtaaactg taccgtcca aaaccttccc ggctgacttc    900
ccagatcaag tcaggacct gtctaaattc gacaccgctc gggcgctgga aattctgaaa    960
tctctgggtc gccaggttg cgttccatc gaagaatcca tcaaagacct ggttggttcc   1020
gaaaccgctt aa                                                     1032

SEQ ID NO: 114          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 114
MAKIDNAVLP EGSLVLVTGA NGFIGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPNYTI GTIFDPETQG GSTSGWMMSL FNGEVSPALA   240
LMPPQYVSA VDIGLLHLGC LVLPQIERRR VYGTAGTFDW NTVLATFRKL YPSKTFPADF    300
PDQGQDLSKF DTARALEILK SLGRPGWRSI EESIKDLVGS ETA                    343

SEQ ID NO: 115          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 115
atggctaaaa tcgataacgc agttctgccg gaaggttccc tggttctggt taccggtgct    60
aacggtttca ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttatgacgaa    240
gttatcaaag gtgcttctgg tgttgctcac atcgcttcc ttgtttcctt ctccaacaaa   300
tacgacgaag ttgttccgcc ggctatcggt ggtaccttga acgctctgcg tgctgctgct   360
gctaccccgt ccgttaaacg tttcgttctg acctcctcca ccgttgcgg ctctgattccg   420
aaaccgaacg ttgaaggtat ctacctggac gaaaaatcct ggaacctgga atccatcgac    480
aaagctaaaa ccctgccgga atccgacccg cagaaatcc tgtgggtata cgctgcatcc    540
aagaccgaag ctgaactggc tgcatggaaa tttatggatg agaacaagcc acacttcact    600
ctgaacgctg tactgccaaa ctacactatt ggcactattt cgatccgga aactcagggc    660
ggttccacct ccgttggat gatgtccctg tttaacggcg aggtttcccc ggctctggct    720
ctgatgccac cgcagtacta cgtttccgct gttgatattg gctgctgca cgtgggtgca    780
ctggttctgc cacaaatcga acgtcgtcgt gtttacggta cggctggtac tttcgattgg    840
aacaccgttc tggctacctt ccgtaaactg taccgtcca aaaccttccc ggctgacttc    900
ccagatcaag tcaggacct gtctaaattc gacaccgctc gggcgctgga aattctgaaa    960
tctctgggtc gccaggttg cgttccatc gaagaatcca tcaaagacct ggttggttcc   1020
gaaaccgctt aa                                                     1032

SEQ ID NO: 116          moltype = AA  length = 343
```

```
FEATURE              Location/Qualifiers
REGION               1..343
                     note = KRED-101 variant
source               1..343
                     mol_type = protein
                     organism = synthetic construct
SEQUENCE: 116
MAKIDNAVLP EGSLVLVTGA NGFIGSHVVE QLLEHGYKVR GTARSASKLA NLQKRWDAKY   60
PGRFETAVVE DMLKQGAYDE VIKGAAGVAH IASVVSFSNK YDEVVPPAIG GTLNALRAAA  120
ATPSVKRFVL TSSTVAALIP KPNVEGIYLD EKSWNLESID KAKTLPESDP QKSLWVYAAS  180
KTEAELAAWK FMDENKPHFT LNAVLPNYTI GTIFDPETQG GSTSGWMMSL FNGEVSPALA  240
LMPPQYYVSA VDIGLLHVGA LVLPQIERRR VYGTAGTFDW NTVLATFRKL YPSKTFPADF  300
PDQGQDLSKF DTARALEILK SLGRPGWRSI EESIKDLVGS ETA                   343

SEQ ID NO: 117       moltype = DNA   length = 1032
FEATURE              Location/Qualifiers
misc_feature         1..1032
                     note = KRED-101 variant
source               1..1032
                     mol_type = other DNA
                     organism = synthetic construct
SEQUENCE: 117
atggctaaaa tcgataacgc agttctgccg gaaggttccc tggttctggt taccggtgct    60
aacggtttca ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttatgacgaa    240
gttatcaaag gtgctgctgg tgttgctcac atcgcttccg ttgtttcctt ctccaacaaa   300
tacgacgaag ttgttccgcc ggctatcggt ggtaccttga cgctctgcg tgctgctgct    360
gctacccgt ccgttaaacg tttcgttctg acctcctcca ccgtttccgc tctgattccg    420
aaaccgaacg ttgaaggtat ctacctggac gaaaaatcc ggaacctgga atccatcgaa    480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacactatt ggcactattt tagatccgga aactcagtcc   660
ggttccacct ccggttggat gatgtccctg tttaacggcg aggttccccc ggctctggct   720
ctgatgccac cgcagtacta cgtttccgtg gttgatattg gcctgctgca cgtgggtgca   780
ctggttctgc cacaaatcga acgtcgtcgt gtttacggta cggctggtac tttcgattgg   840
aacaccgttc tggctacctt ccgtaaactg taccgtccaa aaaccttccc ggctgacttc   900
ccagatcaag tcaggacct gtctaaattc gacaccgctc gggcgctgga aattctgaaa   960
tctctgggtc gcccaggttg gcgttccatc gaagaatcca tcaaagacct ggttggttcc  1020
gaaaccgctt aa                                                     1032

SEQ ID NO: 118       moltype = AA   length = 343
FEATURE              Location/Qualifiers
REGION               1..343
                     note = KRED-101 variant
source               1..343
                     mol_type = protein
                     organism = synthetic construct
SEQUENCE: 118
MAKIDNAVLP EGSLVLVTGA NGFIGSHVVE QLLEHGYKVR GTARSASKLA NLQKRWDAKY   60
PGRFETAVVE DMLKQGAYDE VIKGAAGVAH IASVVSFSNK YDEVVPPAIG GTLNALRAAA  120
ATPSVKRFVL TSSTVSALIP KPNVEGIYLD EKSWNLESID KAKTLPESDP QKSLWVYAAS  180
KTEAELAAWK FMDENKPHFT LNAVLPNYTI GTILDPETQS GSTSGWMMSL FNGEVSPALA  240
LMPPQYYVSV VDIGLLHVGA LVLPQIERRR VYGTAGTFDW NTVLATFRKL YPSKTFPADF  300
PDQGQDLSKF DTARALEILK SLGRPGWRSI EESIKDLVGS ETA                   343

SEQ ID NO: 119       moltype = DNA   length = 1032
FEATURE              Location/Qualifiers
misc_feature         1..1032
                     note = KRED-101 variant
source               1..1032
                     mol_type = other DNA
                     organism = synthetic construct
SEQUENCE: 119
atggctaaaa tcgataacgc agttcttccg gaaggttccc tggttctggt taccggtgct    60
aacggtttcg ttggttccca cgttgttgaa cagctgctgg aacacggtta caaagttcgt   120
ggtaccgctc gttccgcttc caaactggct aatctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttccg ttgtttcctt ctccaacaaa   300
tacgacgaag ttgttacccc ggctatcggt ggtaccttga cgctctgcg tgctgctgct    360
gctgagccgt ccgttaaacg tttcgttctg acctcctcca ccgtttccgc tctgattccg    420
aaaccgaacg ttgaaggtat ctacctggac gaaaaatcct ggaacctgga atccgttgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacactatt ggcactattt cgatccgga aactcagtcc   660
ggttccacct ccggttggat gatgtccctg tttaacggcg aggttccccc ggctctggct   720
ctgatgccac cgcagtacta cgtttccgct gtagatattg gcctgctgca cctgggttgc   780
ctggttctgc cacaaatcga acgtcgtcgt gtttacggta cggctggtac tttcgattgg   840
aacaccgttc tggctacctt ccgtaaactg taccgtccaa aaaccttccc ggctgacttc   900
```

```
ccagatcaag gtcaggacct gtctaaattc gacaccgctc cgtccgaaga acttctgaaa    960
tctctgggtc gcccaggttg gcgttccatc gaagaatcca tcaaagacct ggttggttcc   1020
gaaaccgctt aa                                                        1032

SEQ ID NO: 120          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 120
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
AEPSVKRFVL TSSTVSALIP KPNVEGIYLD EKSWNLESVD KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSEELLK SLGRPGWRSI EESIKDLVGS ETA                     343

SEQ ID NO: 121          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 121
atggctaaaa tcgataacgc agttcttccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac   180
ccgggtcgtt tcgaaaccgc tgttgttgaa gacatgctga acagggtgc ttacgacgaa    240
gttatcaaag gtgctgctgg tgttgctcac atcgcttccg ttgtttcctt ctccaacaaa   300
tacgacgaag ttgttacccc ggctatcggt ggtaccttga cgctctgcg tgctgctgct    360
gctacccgt ccgttaaacg tttcgttctg acctcctccg ccgtttccgc tctgattccg    420
aaaccgaacg ttgaaggtat ctacctggac gaaaaatcct ggaacctgga atccgttgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacaccatt ggcactattt cgatccgga aactcagtcc    660
ggttccacct ccggttggat gatgtccctg tttaacggcg aggtttcccc ggctctggct   720
ctgatgccac cgcagtacta cgtttccgct caggatattg gcctgctgca cctgggttgc   780
ctggttctgc cacaaatcga acgtcgtcgt gttttgtta cggctggtcc gttcgattgg    840
aacaccgttc tggctaccct ccgtaaactg taccgtccca aaaccttccc ggctgacttc   900
ccagatcaag gtcaggacct gtctaaattc gacaccgctc cgtccgaaga acttctgaaa   960
tctctgggtc gcccaggttg gcgttccctt gaagaatcca tcaaagacct ggttggttcc  1020
gaaaccgctt aa                                                       1032

SEQ ID NO: 122          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 122
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESVD KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA QDIGLLHLGC LVLPQIERRR VFGTAGPFDW NTVLATFRKL YPSKTFPADF   300
PDQGQDLSKF DTAPSEELLK SLGRPGWRSL EESIKDLVGS ETA                     343

SEQ ID NO: 123          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 123
atggctaaaa tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac   180
ccgggtcgtt tcgaaaccgc tgttgttgaa gacatgctga acagggtgc ttacgacgaa    240
gttatcaaag gtgctgctgg tgttgctcac atcgcttccg ttgtttcctt ctccaacaaa   300
tacgacgaag ttgttacccc ggctatcggt ggtaccttga cgctctgcg tgctgctgct    360
gctacccgt ccgttaaacg tttcgttctg acctcctcca ccgtttccgc tctgattccg    420
aaaccgaacg ttgaaggtat ctacctggac gaaaaatcct ggaacctgga atccgtcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
```

```
ctgaacgctg tactgccagg gtacactatt ggcactattt tcgatccgga aactcagtcc  660
ggttccacct ccggttggat gatgtccctg tttaacggcg aggtttcccc ggctctggct  720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaccgttc tggctacctt ccgtaaactg tacccgtccc aaaaccttcc ggctgacttc  900
ccagatcaag gtcaggacct gtctaaattc gacaccgctc cgtccctgga aattctgaaa  960
tctctgggtc gcccaggttg gcgttccatc gaagaatcca tcaaagacct ggttggttcc  1020
gaaaccgctt aa                                                     1032

SEQ ID NO: 124          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 124
MAKIDNAVLP EGSLVLVTGA NGFVGSHVVE QLLEHGYKVR GTARSASKLA NLQKRWDAKY   60
PGRFETAVVE DMLKQGAYDE VIKGAAGVAH IASVVSFSNK YDEVVTPAIG GTLNALRAAA  120
ATPSVKRFVL TSSTVSALIP KPNVEGIYLD EKSWNLESID KAKTLPESDP QKSLWVYAAS  180
KTEAELAAWK FMDENKPHFT LNAVLPGYTI GTIFDPETQS GSTSGWMMSL FNGEVSPALA  240
LMPPQYYVSA VDIGLLHLGC LVLPQIERRR VYGTAGTFDW NTVLATFRKL YPSKTFPADF  300
PDQGQDLSKF DTAPSLEILK SLGRPGWRSI EESIKDLVGS ETA                   343

SEQ ID NO: 125          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 125
atggctaaaa tcgataacgc agttctgccg gaaggttccc tggttctggt taccggtgct   60
aacggtttcg ttggttccca cgttgttgaa cagctgctgg aacacggtta caaagttcgt  120
ggtaccgctc gttccgcttc caaactggct aacctgcaga aacgttggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttgtttcctt ctccaacaaa  300
tacgacgaag ttgttacccc ggctatcggt ggtaccttga acgctctgcg tgctgctgct  360
gctaccccgt ccgttaaacg tttcgttctg acctcctcca ccgtttccgc tctgatccg   420
aaaccgaacg ttgaaggtat ctacctggac gaaaaaatcc tggaacctgga atccatcgac  480
aaagctaaaa ccctgccgga atccgacccg cagaaatccc tgtgggtata cgctgcatcc  540
aagaccgaag ctgaactggc tgcatggaaa tttatggatg agaacaagcc acacttcact  600
ctgaacgctg tactgccagg gtacactatt ggcactattt tcgatccgga aactcagtcc  660
ggttccacct ccggttggat gatgtccctg tttaacggcg aggtttcccc ggctctggct  720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaccgttc tggctacctt ccgtaaactg tacccgtccc aaaaccttcc ggctgacttc  900
ccagatcaag gtcaggacct gtctaaattc gacaccgctc cgtccctgga aattctgaaa  960
tctctgggtc gcccaggttg gcgttccatc gaagaatcca tcaaagacct ggttggttcc  1020
gaaaccgctt aa                                                     1032

SEQ ID NO: 126          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 126
MAKIDNAVLP EGSLVLVTGA NGFVGSHVVE QLLEHGYKVR GTARSASKLA NLQKRWDAKY   60
PGRFETAVVE DMLKQGAYDE VIKGAAGVAH IASVVSFSNK YDEVVTPAIG GTLNALRAAA  120
ATPSVKRFVL TSSTVSALIP KPNVEGIYLD EKSWNLESID KAKTLPESDP QKSLWVYAAS  180
KTEAELAAWK FMDENKPHFT LNAVLPGYTI GTIFDPETQS GSTSGWMMSL FNGEVSPALA  240
LMPPQYYVSA VDIGLLHLGC LVLPQIERRR VYGTAGTFDW NTVLATFRKL YPSKTFPADF  300
PDQGQDLSKF DTAPSLEILK SLGRPGWRSI EESIKDLVGS ETA                   343

SEQ ID NO: 127          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 127
atggctaaaa tcgataacgc agttctgccg gaaggttccc tggttctggt taccggtgct   60
aacggtttcg ttggttccca cgttgttgaa cagctgctgg aacacggtta caaagttcgt  120
ggtaccgctc gttccgcttc caaactggct aacctgcaga aacgttggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttgtttcctt ctccaacaaa  300
```

```
tacgacgaag ttgttacccc ggctatcggt ggtaccttga acgctctgcg tgctgctgct   360
gctaccccgt ccgttaaacg tttcgttctg acctcctcca ccttttccgc tctgattccg   420
aaaccgaacg ttgaaggtat ctaccggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct ccgttggat gatgtccctg tttaacggcg aggttccccc ggctctggct   720
ctgatgccac cgcagtacta cgtttccgct gttgatattg gctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaacctttcc ggctgacttc   900
ccagatcaag gtcaggacct gtctaaattc gacaccgctc cgtccctgga aattttgaaa   960
tctctgggtc gcccaggttg gcgttccatc gaagaatcca tcaaagacct ggttggttcc  1020
gaaaccgctt aa                                                      1032

SEQ ID NO: 128            moltype = AA   length = 343
FEATURE                   Location/Qualifiers
REGION                    1..343
                          note = KRED-101 variant
source                    1..343
                          mol_type = protein
                          organism = synthetic construct
SEQUENCE: 128
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTFSALIP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 129            moltype = DNA   length = 1032
FEATURE                   Location/Qualifiers
misc_feature              1..1032
                          note = KRED-101 variant
source                    1..1032
                          mol_type = other DNA
                          organism = synthetic construct
SEQUENCE: 129
atggctaaaa tcgataacgc agttctgccg gaaggttccc tggttctggt taccggtgct    60
aacggttttg ttggttccca cgttgttgaa cagctgctgg aacacggtta caaagttcgt   120
ggtaccgctc gttccgcttc caaactggct aacctgcaga acgttggga cgctaaatac   180
ccgggtcgtt tcgaaaccgc tgttgttgaa gacatgctga acagggtgc ttacgacgaa   240
gttatcaaag gtgctgctgg tgttgctcac atcgcttccg ttgtttcctt ctccaacaaa   300
tacgacgaag ttgttacccc ggctatcggt ggtaccttga acgctctgcg tgctgctgct   360
gctaccccgt ccgttaaacg tttcgttctg acctcctcca ccttttccgc tctgattccg   420
aaaccgaacg ttgaaggtat ctaccggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct ccgttggat gatgtccctg tttaacggcg aggttccccc ggctctggct   720
ctgatgccac cgcagtacta cgtttccgct gttgatattg gctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaacctttcc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgctt aa                                                      1032

SEQ ID NO: 130            moltype = AA   length = 343
FEATURE                   Location/Qualifiers
REGION                    1..343
                          note = KRED-101 variant
source                    1..343
                          mol_type = protein
                          organism = synthetic construct
SEQUENCE: 130
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTFSALIP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 131            moltype = DNA   length = 1032
FEATURE                   Location/Qualifiers
misc_feature              1..1032
                          note = KRED-101 variant
source                    1..1032
                          mol_type = other DNA
                          organism = synthetic construct
SEQUENCE: 131
```

```
atggctaaaa tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttcag ttgtttcctt ctccaacaaa   300
tacgacgaag ttgttacccc ggctatcggt ggtaccttga acgctctgcg tgctgctgct   360
gctaccccgt ccgttaaacg tttcgttctg acctcctcca ccgtttccgc tctggttccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccatc gtacactatt ggcactattt cgatccgga aactcagtcc    660
ggttccacct ccgttggat gatgtccctg tttaacggcg aggtttcccc ggctctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgt    840
aacaccgttc tggctacctt ccgtaaactg tacccgtcca aaaccttccc ggctgacttc    900
ccagatcaag gtcaggacct gtctaaattc gacaccgctc cgtccctgga aattttgaaa    960
tctttgggtc gcccaggttg gcgttccatc gaagaatcca tcaaagacct ggttggttcc   1020
gaaaccgctt aa                                                       1032

SEQ ID NO: 132          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 132
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALVP KPNVEGIYLD EKSWNLESID KAKTLPESDP QKSLWVYAAS   180
KTEAELAAWK FMDENKPHFT LNAVLPSYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 133          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 133
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttcag ttacatcctt ctccaacaaa   300
tacgacgaag ttgttacccc ggctatcggt ggtaccttga acgctctgcg tgctgctgct   360
gctaccccgt ccgttaaacg tttcgttctg acctcctcca ccgtttccgc tctgattccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccagg gtacactatt ggcactattt cgatccgga aactcagtcc    660
ggttccacct ccgttggat gatgtccctg tttaacggcg aggtttcccc ggccctggct    720
ctgatgccac cgcagtacta cgtttccgct gttgatattg gcctgctgca cctgggttgc    780
ctggttctgc cacaaatcga acgtcgtcgt gtttacggta cggctggtac tttcgattgt    840
aacaccgttc tggctacctt ccgtaaactg tacccgtcca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgctt aa                                                       1032

SEQ ID NO: 134          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 134
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVTSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPGYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 135          moltype = DNA  length = 1032
FEATURE                 Location/Qualifiers
misc_feature            1..1032
```

```
                         note = KRED-101 variant
source                   1..1032
                         mol_type = other DNA
                         organism = synthetic construct
SEQUENCE: 135
atggcaaaga tcgataacgc agttctgccg gaaggttccc tggttctggt taccggtgct    60
aacggtttca ttggttccca cgttgttgaa cagctgctgg aacacggtta caaagttcgt   120
ggtaccgctc gttccgcttc caaactggct aacctgcaga aacgttggga cgctaaatac   180
ccgggtcgtt tcgaaaccgc tgttgttgaa gacatgctga aacgggtgc ttacgacgaa    240
gttatcaaag gtgctgctgg tgttgctcac atcgcttccg ttacatcctt ctccaacaaa   300
tacgacgaag ttgttacccc ggctatcggt ggtaccttga cgctctgcg tgctgctgct    360
gctaccccgt ccgttaaacg tttcgttctg acctcctcca ccgtttccgc tctgattccg   420
aaaccgaacg ttgaaggtat ctacctggac gaaaaaatcc ggaactggga atccatcgac   480
aaagctaaaa ccctgccgga atccgacccg cagaaatccc tgtgggtata cgctgcatcc   540
aagaccgaag ctgaactggc tgcatggaaa tttatggatg agaacaagcc acacttcact   600
ctgaacgctg tactgccagg atacactatt ggcactattt cgatccgga aactcagtcc    660
ggttccacct ccgttggat gacgtccctg tttaacggcg aggtttcccc ggccctggct    720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg taccgtccca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgctt aa                                                      1032

SEQ ID NO: 136          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 136
MAKIDNAVLP EGSLVLVTGA NGFIGSHVVE QLLEHGYKVR GTARSASKLA NLQKRWDAKY    60
PGRFETAVVE DMLKQGAYDE VIKGAAGVAH IASVTSFSNK YDEVVTPAIG GTLNALRAAA   120
ATPSVKRFVL TSSTVSALIP KPNVEGIYLD EKSWNLESID KAKTLPESDP QKSLWVYAAS   180
KTEAELAAWK FMDENKPHFT LNAVLPGYTI GTIFDPETQS GSTSGWMTSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 137          moltype = DNA  length = 1032
FEATURE                 Location/Qualifiers
misc_feature            1..1032
                        note = KRED-101 variant
source                  1..1032
                        mol_type = other DNA
                        organism = synthetic construct
SEQUENCE: 137
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga aacgttggga cgctaaatac   180
ccgggtcgtt tcgaaaccgc tgttgttgaa gacatgctga aacagggtgc ttacgacgaa   240
gttatcaaag gtgctgctgg tgttgctcac atcgcttccg ttacatcctt ctccaacaaa   300
tacgacgaag ttgttacccc ggctatcggt ggtaccttga cgctctgcg tgctgctgct    360
gctaccccgt ccgttaaacg tttcgttctg acctcctcca ccttttccgc tctggttccg   420
aaaccgaacg ttgaaggtat ctacctggac gaaaaaatcc ggaactggga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt cgatccgga aactcagtcc    660
ggttccacct ccgttggat gatgtccctg tttaacggcg aggtttcccc ggctctggct    720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg taccgtccca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgctt aa                                                      1032

SEQ ID NO: 138          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 138
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVTSFSNK YDEVVTPAIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
```

-continued

```
PDQGQDLSKF DTAPSLEILK SLGRPGWRSI EESIKDLVGS ETA              343

SEQ ID NO: 139          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 139
atggcataca tcgataacgc agttctgccg gaaggttccc tggttctggt taccggtgct  60
aacggtttcg ttggttccca cgttgttgaa cagctgctgg aacacggtta caagttcgt  120
ggtaccgctc gttccgcttc caaactggct aacctgcaga aacgttggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttacatcctt ctccaacaaa  300
tacgacgaag ttgttacccc ggctatcggt ggtaccttga cgctctgcg tgctgctgct  360
gctacccccgt ccgttaaacg tttcgttctg acctcctcca ccgtttccgc tctgattccg  420
aaaccgaacg ttgaaggtat ctacctggac gaaaaatcct ggaacctgga atccatcgac  480
aaagctaaaa ccctgccgga atccgacccg cagaaatccc tgtgggtata cgctgcatcc  540
aagaccgaag ctgaactggc tgcatggaaa tttatggatg agaacaagcc acacttcact  600
ctgaacgctg tactgccagg gtacactatt ggcactattt cgatccggga aactcagtcc  660
ggttccacct ccggttggat gatgtccctg tttaacggcg aggttcccc ggccctggct  720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaccgttc tggctacctt ccgtaaactg tacccgtcca aaccttccc ggctgacttc  900
ccagatcaag gtcaggacct gtctaaattc gacaccgctc cgtccctgga aattctgaaa  960
tctctgggtc gccaggttg gcgttccatc gaagaatcca tcaaagacct ggttggttcc 1020
gaaaccgctt aa                                                    1032

SEQ ID NO: 140          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 140
MAYIDNAVLP EGSLVLVTGA NGFVGSHVVE QLLEHGYKVR GTARSASKLA NLQKRWDAKY  60
PGRFETAVVE DMLKQGAYDE VIKGAAGVAH IASVTSFSNK YDEVVTPAIG GTLNALRAAA 120
ATPSVKRFVL TSSTVSALIP KPNVEGIYLD EKSWNLESID KAKTLPESDP QKSLWVYAAS 180
KTEAELAAWK FMDENKPHFT LNAVLPGYTI GTIFDPETQS GSTSGWMMSL FNGEVSPALA 240
LMPPQYYVSA VDIGLLHLGC LVLPQIERRR VYGTAGTFDW NTVLATFRKL YPSKTFPADF 300
PDQGQDLSKF DTAPSLEILK SLGRPGWRSI EESIKDLVGS ETA              343

SEQ ID NO: 141          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 141
atggcataca tcgataacgc agttctgccg gaaggttccc tggttctggt taccggtgct  60
aacggtttcg ttggttccca cgttgttgaa cagctgctgg aacacggtta caagttcgt  120
ggtaccgctc gttccgcttc caaactggct aacctgcaga aacgttggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttacatcctt ctccaacaaa  300
tacgacgaag ttgttacccc ggctatcggt ggtaccttga cgctctgcg tgctgctgct  360
gctacccccgt ccgttaaacg tttcgttctg acctcctcca ccgtttccgc tctgattccg  420
aaaccgaacg ttgaaggtat ctacctggac gaaaaatcct ggaacctgga atccatcgac  480
aaagctaaaa ccctgccgga atccgacccg cagaaatccc tgtgggtata cgctgcatcc  540
aagaccgaag ctgaactggc tgcatggaaa tttatggatg agaacaagcc acacttcact  600
ctgaacgctg tactgccagg atacactatt ggcactattt cgatccggga aactcagtcc  660
ggttccacct ccggttggat gatgtccctg tttaacggcg aggttcccc ggccctggct  720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaccgttc tggctacctt ccgtaaactg tacccgtcca aaccttccc ggctgacttc  900
ccagatcaag gtcaggacct gtctaaattc gacaccgctc cggtccctga aattctgaaa  960
tctctgggtc gccaggttg gcgttccatc gaagaatcca tcaaagacct ggttggttcc 1020
gaaaccgctt aa                                                    1032

SEQ ID NO: 142          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 142
```

```
MAYIDNAVLP EGSLVLVTGA NGFVGSHVVE QLLEHGYKVR GTARSASKLA NLQKRWDAKY   60
PGRFETAVVE DMLKQGAYDE VIKGAAGVAH IASVTSFSNK YDEVVTPAIG GTLNALRAAA  120
ATPSVKRFVL TSSTVSALIP KPNVEGIYLD EKSWNLESID KAKTLPESDP QKSLWVYAAS  180
KTEAELAAWK FMDENKPHFT LNAVLPGYTI GTIFDPETQS GSTSGWMTSL FNGEVSPALA  240
LMPPQYYVSA VDIGLLHLGC LVLPQIERRR VYGTAGTFDW NTVLATFRKL YPSKTFPADF  300
PDQGQDLSKF DTARSLEILK SLGRPGWRSI EESIKDLVGS ETA                   343

SEQ ID NO: 143          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 143
atgactaaga tcgataacgc agttctgccg aaggttccc tggttctggt taccggtgct    60
aacggtttcg ttggttccca cgttgttgaa cagctgctgg aacacggtta caaagttcgt  120
ggtaccgctc gttccgcttc caaactggct aacctgcaga acgttgggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttgtttcctt ctccaacaaa  300
cctgacgaag ttgttacccc ggctatcggt ggtaccttga cgctctgcg tgctgctgct  360
gctacccgt ccgttaaacg tttcgttctg acctcctccg ccgtttccgc tctgattccg  420
aaaccgaacg ttgaaggtat ctacctggac gaaaaatcct ggaacctgga atccatcgac  480
aaagctaaaa ccctgccgga atccgaccgg cagaaatccc tgtgggtata cgctctgtcc  540
aagatggaag ctgaactggc tgcatggaaa tttatggatg agaacaagcc acacttcact  600
ctgaacgctg tactgccagg gtacactatt ggcactattt cgatccgga aactcagtcc  660
ggttccacct ccggttggat gaggtccctg tttaacggcg aggttcccc gttgctggct  720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaaggttc tggctacctt ccgtaaactg tacccgtcca aaaccttccc ggctgacttc  900
ccagatcaag gtcaggacct gtctaaattc gacaccgctc gtccctgga aattctgaaa  960
tctctgggtc gcccaggttg gcgttccatc gaagaatcca tcaaagacct ggttggttcc 1020
gaaaccgctt aa                                                    1032

SEQ ID NO: 144          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 144
MTKIDNAVLP EGSLVLVTGA NGFVGSHVVE QLLEHGYKVR GTARSASKLA NLQKRWDAKY   60
PGRFETAVVE DMLKQGAYDE VIKGAAGVAH IASVVSFSNK PDEVVTPAIG GTLNALRAAA  120
ATPSVKRFVL TSSTVSALIP KPNVEGIYLD EKSWNLESID KAKTLPESDP QKSLWVYALS  180
KMEAELAAWK FMDENKPHFT LNAVLPGYTI GTIFDPETQS GSTSGWMRSL FNGEVSPLLA  240
LMPPQYYVSA VDIGLLHLGC LVLPQIERRR VYGTAGTFDW NEVLATFRKL YPSKTFPADF  300
PDQGQDLSKF DTAPSLEILK SLGRPGWRSI EESIKDLVGS ETA                   343

SEQ ID NO: 145          moltype = DNA   length = 1032
FEATURE                 Location/Qualifiers
misc_feature            1..1032
                        note = KRED-101 variant
source                  1..1032
                        mol_type = other DNA
                        organism = synthetic construct
SEQUENCE: 145
atggctaaaa tcgataacgc agttctgccg aaggttccc tggttctggt taccggtgct    60
aacggtttcg ttggttccca cgttgttgaa cagctgctgg aacacggtta caaagttcgt  120
ggtaccgctc gttccgcttc caaactggct aacctgcaga acgttgggga cgctaaatac  180
ccgggtcgtt tcgaaaccgc tgttgttgaa gacatgctga aacagggtgc ttacgacgaa  240
gttatcaaag gtgctgctgg tgttgctcac atcgcttccg ttgtttcctt ctccaacaaa  300
tacgacgaag ttgttacccc ggctatcggt ggtaccttga cgctctgcg tgctgctgct  360
gctacccgt ccgttaaacg tttcgttctg acctcctccg ccgtttccgc tctgattccg  420
aagccgaacg ttgaaggtat ctacctggac gaaaagtcct ggaacctgga tccgttgac   480
aaagctaaaa ccctgccgga atccgaccgg cagaaatccc tgtgggtata cgctgcatcc  540
aagaccgaag ctgaactggc tgcatggaaa tttatggatg agaacaagcc acacttcact  600
ctgaacgctg tactgccagg gtacactattt tcgatccgga aactcagtcc             660
ggttccacct ccggttggat gctgtccctg tttaacggcg aggttcgc ggctctggct    720
ctgatgccac cgcagtacta cgtttccgct gttgatattg gcctgctgca cctgggttgc  780
ctggttctgc cacaaatcga acgtcgtcgt gtttacggta cggctggtac tttcgattgg  840
aacaccgttc tggctacctt ccgtaaactg tacccgtcca aaaccttccc ggctgacttc  900
ccagatcaag gtcaggacct gtctcaattc gacaccgctc gtccctgga aattctgaaa   960
tctctgggtc gcccaggttg gcgttccctt gaagaatcca tcaaagacct ggttggttcc 1020
gaaaccgctt aa                                                    1032

SEQ ID NO: 146          moltype = AA   length = 343
FEATURE                 Location/Qualifiers
REGION                  1..343
```

```
                        note = KRED-101 variant
source                  1..343
                        mol_type = protein
                        organism = synthetic construct
SEQUENCE: 146
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVVSFSNK YDEVVTPAIG GTLNALRAAA   120
ATPSVKRFVL TSSTVSALIP KPNVEGIYLD EKSWNLESVD KAKTLPESDP QKSLWVYAAS   180
KTEAELAAWK FMDENKPHFT LNAVLPGYTI GTIFDPETQS GSTSGWMLSL FNGEVSPALA   240
LMPPQYYVSA VDIGLLHLGC LVLPQIERRR VYGTAGTFDW NTVLATFRKL YPSKTFPADF   300
PDQGQDLSQF DTAPSLEILK SLGRPGWRSL EESIKDLVGS ETA                    343

SEQ ID NO: 147          moltype = DNA  length = 1029
FEATURE                 Location/Qualifiers
misc_feature            1..1029
                        note = KRED-101 variant
source                  1..1029
                        mol_type = other DNA
                        organism = synthetic construct
SEQUENCE: 147
atggcaaaga tcgataacgc agttctgccg gaaggttccc tggttctggt taccggtgct    60
aacggtttca ttggttccca cgttgttgaa cagctgctgg aacacggtta caaagttcgt   120
ggtaccgtgc gttccgctga aaaaaatgct aacctgcaga acgttggga cgctaaatac   180
ccgggtcgtt tcgaaaccgt ggaagttcca gacatgctga acagggtgc ttacgacgaa   240
gttatcaaag gtgctgctgg tgttgctcac gttgcttccg taacatcctt ctccaacaaa   300
tacgacgaag ttgttacccc ggctatcggt ggtaccttga acgctctgcg tgctgctgct   360
gctaccccgt ccgttaaacg tttcgttctg acctcctcca cctttccgc tctggttccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt tcgatccgga aacccagggc   660
gggtccacct ccggttggat gatgtccctg tttaacggcg aggttccc ggctctggct   720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaacctttcc ggctgacttc   900
ccagatcaag tcaggacct gtctaaattc gacaccgctc cgtccctgga attctctgaaa   960
tctctgggtc gcccaggttg gcgttccatc gaagaatcca tcaaagacct ggttggttcc  1020
gaaaccgct                                                          1029

SEQ ID NO: 148          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 148
MAKIDNAVLP EGSLVLVTGA NGFIGSHVVE QLLEHGYKVR GTVRSAEKNA NLQKRWDAKY    60
PGRFETVEVP DMLKQGAYDE VIKGAAGVAH VASVTSFSNK YDEVVTPAIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                    343

SEQ ID NO: 149          moltype = DNA  length = 1029
FEATURE                 Location/Qualifiers
misc_feature            1..1029
                        note = KRED-101 variant
source                  1..1029
                        mol_type = other DNA
                        organism = synthetic construct
SEQUENCE: 149
atggcaaaga tcgataacgc agttctgccg gaaggttccc tggttctggt taccggtgct    60
aacggtttca ttggttccca cgttgttgaa cagctgctgg aacacggtta caaagttcgt   120
ggtaccgcgc gttccgcttc aaaacttgct aacctgcaga acgttggga cgctaaatac   180
ccgggtcgtt tcgaaaccgc ggaagttgag gacatgctga acagggtgc ttacgacgaa   240
gttatcaaag gtgctgctgg tgttgctcac gttgcttccg taacatcctt ctccaacaaa   300
tacgacgaag ttgttacccc ggctatcggt ggtaccttga acgctctgcg tgctgctgct   360
gctaccccgt ccgttaaacg tttcgttctg acctcctcca cctttccgc tctggttccg   420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt tcgatccgga aacccagggc   660
gggtccacct ccggttggat gatgtccctg tttaacggcg aggttccc ggctctggct   720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaacctttcc ggctgacttc   900
ccagatcaag tcaggacct gtctaaattc gacaccgctc cgtccctgga attctctgaaa   960
tctctgggtc gcccaggttg gcgttccatc gaagaatcca tcaaagacct ggttggttcc  1020
```

```
gaaaccgct                                                              1029

SEQ ID NO: 150          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 150
MAKIDNAVLP EGSLVLVTGA NGFIGSHVVE QLLEHGYKVR GTARSASKLA NLQKRWDAKY   60
PGRFETAEVE DMLKQGAYDE VIKGAAGVAH VASVTSFSNK YDEVVTPAIG GTLNALRAAA  120
ATPSVKRFVL TSSTFSALVP KPNVEGIYLD EKSWNLESID KAKTLPESDP QKSLWVYAAS  180
KTEAELAAWK FMDENKPHFT LNAVLPNYTI GTIFDPENQG GSTSGWMMSL FNGEVSPALA  240
LMPPQYYVSA VDIGLLHLGC LVLPQIERRR VYGTAGTFDW NTVLATFRKL YPSKTFPADF  300
PDQGQDLSKF DTAPSLEILK SLGRPGWRSI EESIKDLVGS ETA                    343

SEQ ID NO: 151          moltype = DNA  length = 1029
FEATURE                 Location/Qualifiers
misc_feature            1..1029
                        note = KRED-101 variant
source                  1..1029
                        mol_type = other DNA
                        organism = synthetic construct
SEQUENCE: 151
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgctta gcaaggtgc ttttgacgaa    240
gttatcaaag gtgctgctgg tgttgctcac atcgcttccg ttcatccctt ttccaacaaa   300
tacgacgagg ttgttaccgg tgcgatcggt ggtaccttga acgctctgcg tgctgctgct   360
gctaccccgt ccgttaaacg ttttgttctg acctcctcca cctttccgc tctggttccg    420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactatct ttgatccgga aactcagtcc   660
ggttccacct ccggttggat gatgtccctg tttaacggcg aggtttcccc ggctctggct   720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg taccgtccca aaaccttccc ggctgacttc   900
ccagatcaag gtcaggacct gtctaaattc gacaccgctc cgtccctgga aattctgaaa   960
tctctgggtc gcccaggttg cgttccatc gaagaatcca tcaaagacct ggttggttcc  1020
gaaaccgct                                                         1029

SEQ ID NO: 152          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 152
MAKIDNAVLP EGSLVLVTGA NGFVGSHVVE QLLEHGYKVR GTARSASKLA NLQKRWDAKY   60
PGRFETAVVE DMLKQGAFDE VIKGAAGVAH IASVTSFSNK YDEVVTGAIG GTLNALRAAA  120
ATPSVKRFVL TSSTFSALVP KPNVEGIYLD EKSWNLESID KAKTLPESDP QKSLWVYAAS  180
KTEAELAAWK FMDENKPHFT LNAVLPNYTI GTIFDPETQS GSTSGWMMSL FNGEVSPALA  240
LMPPQYYVSA VDIGLLHLGC LVLPQIERRR VYGTAGTFDW NTVLATFRKL YPSKTFPADF  300
PDQGQDLSKF DTAPSLEILK SLGRPGWRSI EESIKDLVGS ETA                    343

SEQ ID NO: 153          moltype = DNA  length = 1029
FEATURE                 Location/Qualifiers
misc_feature            1..1029
                        note = KRED-101 variant
source                  1..1029
                        mol_type = other DNA
                        organism = synthetic construct
SEQUENCE: 153
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaatac    180
ccgggtcgtt tcgaaaccgc tgttgttgaa gacatgcttg cagaaggtgc ttttgacgaa   240
gttatcaaag gtgctgctgg tgttgctcac atcgcttccg ttcatccctt ctccaacaaa   300
tacgacgagg ttgttacccc cgtgatcggt ggtaccttga acgctctgcg tgctgctgct   360
gctaccccgt ccgttaaacg ttttgttctg acctcctcca cctttccgc tctggttccg    420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatggatg agaacaagcc acacttcact   600
ctgaacgctg tactgccaaa ctacactatt ggcactattt tcgatccgga aactcagtcc   660
ggttccacct cgggttggat gatgtccctg tttaacggcg aggtttcccc ggctctggct   720
```

```
ctgatgccac cgcaatacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgct                                                          1029
```

```
SEQ ID NO: 154          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 154
MAKIDNAVLP EGSLVLVTGA NGFVGSHVVE QLLEHGYKVR GTARSASKLA NLQKRWDAKY    60
PGRFETAVVE DMLAEGAFDE VIKGAAGVAH IASVTSFSNK YDEVVTPVIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 155          moltype = DNA   length = 1029
FEATURE                 Location/Qualifiers
misc_feature            1..1029
                        note = KRED-101 variant
source                  1..1029
                        mol_type = other DNA
                        organism = synthetic construct
SEQUENCE: 155
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgtgggac gctaaatac    180
ccgggtcgtt tcgaaaccgc tgttgttgaa gacatgctta aggaaggtgc ttttgacgaa   240
gttatcaaag gtgctgctgg tgttgctcac atcgcttccg ttacatcctt ctcccccaaa   300
tacgacgagg ttgttacccc cgtgatcggt ggtaccttga acgctctgcg tgctgctgct   360
gctaccccgt ccgttaaacg tttcgttctg acctcctcca cctttccgc tctggttccg   420
aaaccgaacg ttgaaggtat ctacctggac gaaaaatcct ggaacctgga atccatcgac   480
aaagctaaaa ccctgccgga atccgacccg cagaaatcc tgtgggtata cgctgcgtcc   540
aagaccgaag ctgaactggc tgcatggaaa tttatggatg agaacaagcc acacttcact   600
ctgaacgctg tactgccaaa ctacactatt ggcactatct tttctccgga aactcagtcc   660
ggttccaccc ggggttggat gatgtccctg tttaacggcg aggtttcccc ggctctggct   720
ctgatgccac cgcagtacta cgtttccgct gttgatattg gcctgctgca cctgggttgc   780
ctggttctgc cacaaatcga acgtcgtcgt gtttacggta cggctggtac tttcgattgg   840
aacaccgttc tggctacctt ccgtaaactg tacccgtcca aaaccttccc ggctgacttc   900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgct                                                          1029

SEQ ID NO: 156          moltype = AA   length = 343
FEATURE                 Location/Qualifiers
REGION                  1..343
                        note = KRED-101 variant
source                  1..343
                        mol_type = protein
                        organism = synthetic construct
SEQUENCE: 156
MAKIDNAVLP EGSLVLVTGA NGFVGSHVVE QLLEHGYKVR GTARSASKLA NLQKRWDAKY    60
PGRFETAVVE DMLKEGAFDE VIKGAAGVAH IASVTSFSPK YDEVVTPVIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFSPETQS GSTAGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 157          moltype = DNA   length = 1029
FEATURE                 Location/Qualifiers
misc_feature            1..1029
                        note = KRED-101 variant
source                  1..1029
                        mol_type = other DNA
                        organism = synthetic construct
SEQUENCE: 157
atggcaaaga tcgataacgc agttctgccg gaaggttccc tggttctggt tacctcggct    60
aacggtttcg ttggttccca cgttgttgaa cagctgctgg aacacggtta caaagttcgt   120
ggtaccgctc gttccgcttc caaactggct aacctgcaga acgttgggac gctaaatac    180
ccgggtcgtt tcgaaaccgc tgttgttgaa gacatgctga acagggtgc ttacgacgaa   240
gttatcaaag gtgctgctgg tgttgctcac atcgcttccg ttacatcctt ctccaacaaa   300
tacgacgagg ttgttacccc ggtgatcggt ggtaccttga acgctctgcg tgctgctgct   360
gctacccgt ccgttaaacg tttcgttctg acctcctcca cctttccgc tctggttccg    420
```

```
aaaccgaacg ttgaaggtat ctacctggac gaaaaatcct ggaacctgga atccatcgac    480
aaagctaaaa ccctgccgga atccgacccg cagaaatccc tgtgggtata cgctgcgtcc    540
aagaccgaag ctgaactggc tgcatggaaa tttatggatg agaacaagcc acacttcact    600
ctgaacgctg tactgccaaa ctacactatt ggcactattt cgatccgga aactcagtcc     660
ggttccacct ccgttggat gatgtccctg tttaacggcg aggtttcccc ggctctggct     720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctacctt ccgtaaactg tacccgtcca aaccttccc ggctgacttc     900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                           1029

SEQ ID NO: 158         moltype = AA   length = 343
FEATURE                Location/Qualifiers
REGION                 1..343
                       note = KRED-101 variant
source                 1..343
                       mol_type = protein
                       organism = synthetic construct
SEQUENCE: 158
MAKIDNAVLP EGSLVLVTSA NGFVGSHVVE QLLEHGYKVR GTARSASKLA NLQKRWDAKY     60
PGRFETAVVE DMLKQGAYDE VIKGAAGVAH IASVTSFSNK YDEVVTPAIG GTLNALRAAA    120
ATPSVKRFVL TSSTFSALVP KPNVEGIYLD EKSWNLESID KAKTLPESDP QKSLWVYAAS    180
KTEAELAAWK FMDENKPHFT LNAVLPNYTI GTIFDPETQS GSTSGWMMSL FNGEVSPALA    240
LMPPQYYVSA VDIGLLHLGC LVLPQIERRR VYGTAGTFDW NTVLATFRKL YPSKTFPADF    300
PDQGQDLSKF DTAPSLEILK SLGRPGWRSI EESIKDLVGS ETA                      343

SEQ ID NO: 159         moltype = DNA  length = 1029
FEATURE                Location/Qualifiers
misc_feature           1..1029
                       note = KRED-101 variant
source                 1..1029
                       mol_type = other DNA
                       organism = synthetic construct
SEQUENCE: 159
atggcaaaga tcgataacgc agttctgccg gaaggttccc tggttctggt taccggtgct     60
aacggtttcg ttggttccca cgttgttgaa cagctgctgg aacacggtta caagttcgt    120
ggtaccgctc gttccgcttc caaactggct aacctgcaga acgttggga cgctaaatac    180
ccgggtcgtt tcgaaaccgc tgttgttgaa gacatgctga acaggggtgc ttacgacgaa    240
gttatcaaag gtgctgctgg tgttgctcac atcgcttccg tttgttcctt ctccaacaaa    300
tacgacgaag ttgttacccc ggctatcggt ggtaccttga cgctctgcg tgctgctgct    360
gctacccgt ccgttaaacg tttcgttctg acctcctcca ccttttccgc tctggttccg     420
aaaccgaacg ttgaaggtat ctacctggac gaaaaatcct ggaacctgga atccatcgac    480
aaagctaaaa ccctgccgga atccgacccg cagaaatccc tgtgggtata cgctgcgtcc    540
aagaccgaag ctgaactggc tgcatggaaa tttatggatg agaacaagcc acacttcact    600
ctgaacgctg tactgccaaa ctacactatt ggcactattt cgatccgga aactcagtcc     660
ggttccacct ccgttggat gatgtccctg tttaacggcg aggtttcccc ggctctggct     720
ctgatgccac cgcagtacta cgtttccgct gttgatattg gcctgctgca cctgggttgc    780
ctggttctgc cacaaatcga acgtcgtcgt gtttacggta cggctggtac tttcgattgg    840
aacaccgttc tggctacctt ccgtaaactg tacccgtcca aaccttccc ggctgacttc     900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                           1029

SEQ ID NO: 160         moltype = AA   length = 343
FEATURE                Location/Qualifiers
REGION                 1..343
                       note = KRED-101 variant
source                 1..343
                       mol_type = protein
                       organism = synthetic construct
SEQUENCE: 160
MAKIDNAVLP EGSLVLVTGA NGFVGSHVVE QLLEHGYKVR GTARSASKLA NLQKRWDAKY     60
PGRFETAVVE DMLKQGAYDE VIKGAAGVAH IASVCSFSNK YDEVVTPAIG GTLNALRAAA    120
ATPSVKRFVL TSSTFSALVP KPNVEGIYLD EKSWNLESID KAKTLPESDP QKSLWVYAAS    180
KTEAELAAWK FMDENKPHFT LNAVLPNYTI GTIFDPETQS GSTSGWMMSL FNGEVSPALA    240
LMPPQYYVSA VDIGLLHLGC LVLPQIERRR VYGTAGTFDW NTVLATFRKL YPSKTFPADF    300
PDQGQDLSKF DTAPSLEILK SLGRPGWRSI EESIKDLVGS ETA                      343

SEQ ID NO: 161         moltype = DNA  length = 1029
FEATURE                Location/Qualifiers
misc_feature           1..1029
                       note = KRED-101 variant
source                 1..1029
                       mol_type = other DNA
                       organism = synthetic construct
SEQUENCE: 161
atggcaaaga tcgataacgc agttctgccg gaaggttccc tggttctggt taccggtgct     60
aacggtttcg ttggttccca cgttgttgaa cagctgctgg aacacggtta caagttcgt    120
```

```
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttccg ttacagggtt ctccaacaaa    300
tacgacgaag ttgttacccc ggctatcggt ggtaccttga acgctctgcg tgctgctgct    360
gctaccccgt ccgttaaacg tttcgttctg acctcctcca ccttttccgc tctggttccg    420
aaaccgaacg ttgaaggtat ctacctggac gaaaaatcct ggaacctgga atccatcgac    480
aaagctaaaa ccctgccgga atccgacccg cagaaatccc tgtggtata cgctgcgtcc    540
aagaccgaag ctgaactggc tgcatggaaa tttatggatg agaacaagcc acacttcact    600
ctgaacgctg tactgccaaa ctacactatt ggcactattt tcgatccgga aactcagtcc    660
ggttccacct ccgttggat gatgtccctg tttaacggcg aggtttcccc ggctctggct    720
ctgatgccac cgcagtacta cgtttccgct gttgatattg gctgctgca cctgggttgc    780
ctggttctgc cacaaatcga acgtcgtcgt gtttacggta cggctggtac tttcgattgg    840
aacaccgttc tggctacctt ccgtaaactg taccgtccca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                           1029

SEQ ID NO: 162       moltype = AA   length = 343
FEATURE              Location/Qualifiers
REGION               1..343
                     note = KRED-101 variant
source               1..343
                     mol_type = protein
                     organism = synthetic construct
SEQUENCE: 162
MAKIDNAVLP EGSLVLVTGA NGFVGSHVVE QLLEHGYKVR GTARSASKLA NLQKRWDAKY     60
PGRFETAVVE DMLKQGAYDE VIKGAAGVAH IASVTGFSNK YDEVVTPAIG GTLNALRAAA    120
ATPSVKRFVL TSSTFSALVP KPNVEGIYLD EKSWNLESID KAKTLPESDP QKSLWVYAAS    180
KTEAELAAWK FMDENKPHFT LNAVLPNYTI GTIFDPETQS GSTSGWMMSL FNGEVSPALA    240
LMPPQYYVSA VDIGLLHLGC LVLPQIERRR VYGTAGTFDW NTVLATFRKL YPSKTFPADF    300
PDQGQDLSKF DTAPSLEILK SLGRPGWRSI EESIKDLVGS ETA                      343

SEQ ID NO: 163       moltype = DNA   length = 1029
FEATURE              Location/Qualifiers
misc_feature         1..1029
                     note = KRED-101 variant
source               1..1029
                     mol_type = other DNA
                     organism = synthetic construct
SEQUENCE: 163
atggcaaaga tcgataacgc agttctgccg gaaggttccc tggttctggt tacctcggct     60
aacggtttcg ttggttccca cgttgttgaa cagctgctgg aacacggtta caagttcgt    120
ggtaccgctc gttccgcttc caaactggct aacctgcaga acgttggga cgctaaatac    180
ccgggtcgtt tcgaaaccgc tgttgttgaa gacatgctga acagggtgc ttacgacgaa    240
gttatcaaag gtgctgctgg tgttgctcac atcgcttccg ttacatcctt ctccaacaaa    300
tacgacgaag ttgttacccc ggctatcggt ggtaccttga acgctctgcg tgctgctgct    360
gctaccccgt ccgttaaacg tttcgttctg acctcctcca ccttttccgc tctggttccg    420
aaaccgaacg ttgaaggtat ctacctggac gaaaaatcct ggaacctgga atccatcgac    480
aaagctaaaa ccctgccgga atccgacccg cagaaatccc tgtggtata cgctgcgtcc    540
aagaccgaag ctgaactggc tgcatggaaa tttatggatg agaacaagcc acacttcact    600
ctgaacgctg tactgccaaa ctacactatt ggcactattt tcgatccgga aactcagtcc    660
ggttccacct ccgttggat gatgtccctg tttaacggcg aggtttcccc ggctctggct    720
ctgatgccac cgcagtacta cgtttccgct gttgatattg gctgctgca cctgggttgc    780
ctggttctgc cacaaatcga acgtcgtcgt gtttacggta cggctggtac tttcgattgg    840
aacaccgttc tggctacctt ccgtaaactg taccgtccca aaaccttccc ggctgacttc    900
ccagatcaag gtcaggacct gtctaaattc gacaccgctc cgtccctgga aattctgaaa    960
tctctgggtc gcccaggttg gcgttccatc gaagaatcca tcaaagacct ggttggttcc   1020
gaaaccgct                                                           1029

SEQ ID NO: 164       moltype = AA   length = 343
FEATURE              Location/Qualifiers
REGION               1..343
                     note = KRED-101 variant
source               1..343
                     mol_type = protein
                     organism = synthetic construct
SEQUENCE: 164
MAKIDNAVLP EGSLVLVTSA NGFVGSHVVE QLLEHGYKVR GTARSASKLA NLQKRWDAKY     60
PGRFETAVVE DMLKQGAYDE VIKGAAGVAH IASVTSFSNK YDEVVTPAIG GTLNALRAAA    120
ATPSVKRFVL TSSTFSALVP KPNVEGIYLD EKSWNLESID KAKTLPESDP QKSLWVYAAS    180
KTEAELAAWK FMDENKPHFT LNAVLPNYTI GTIFDPETQS GSTSGWMMSL FNGEVSPALA    240
LMPPQYYVSA VDIGLLHLGC LVLPQIERRR VYGTAGTFDW NTVLATFRKL YPSKTFPADF    300
PDQGQDLSKF DTAPSLEILK SLGRPGWRSI EESIKDLVGS ETA                      343

SEQ ID NO: 165       moltype = DNA   length = 1029
FEATURE              Location/Qualifiers
misc_feature         1..1029
                     note = KRED-101 variant
source               1..1029
```

```
                        mol_type = other DNA
                        organism = synthetic construct
SEQUENCE: 165
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaaatac   180
ccgggtcgtt tcgaaaccgc tgttgttgaa gaccagctga acagggtgc ttacgacgaa    240
gttatcaaag tgctgctgg tgttgctcac atcgcttccg ttacatcctt ctccaacaaa    300
tacgacgaag ttgttacccc ggctatcggt ggtaccttga acgctctgcg tgctgctgct   360
gctaccccgt ccgttaaacg tttcgttctg acctcctcca cctttccgc tctggttccg    420
aaaccgaacg ttgaaggtat ctacctggac gaaaaaatcct ggaacctgga atccatcgac   480
aaagctaaaa ccctgccgga atccgaccc cagaaatccc tgtgggtata cgctgcgtcc   540
aagaccgaag ctgaactggc tgcatggaaa tttatgatg agaacaagcc acacttcact    600
ctgaacgctg tactgccaaa ctacactatt ggcactattt tcgatccgga aactcagtcc   660
ggttccacct ccggttggat gatgtccctg tttaacggcg aggttccccc ggctctggct    720
ctgatgccac cgcagtacta cgtttccgct gttgatattg gctgctgca cctgggttgc    780
ctggttctgc cacaaatcga acgtcgtcgt gtttacggta cggctggtac tttcgattgg   840
aacaccgttc tggctacctt ccgtaaactg tacccgtcca aaaccttccc ggctgacttc    900
ccagatcaag tcaggacct gtctaaattc gacaccgctc cgtccctgga aattctgaaa    960
tctctgggtc gccaggttg gcgttccatc gaagaatcca tcaaagacct ggttggttcc   1020
gaaaccgct                                                          1029

SEQ ID NO: 166         moltype = AA  length = 343
FEATURE                Location/Qualifiers
REGION                 1..343
                       note = KRED-101 variant
source                 1..343
                       mol_type = protein
                       organism = synthetic construct
SEQUENCE: 166
MAKIDNAVLP EGSLVLVTGA NGFVGSHVVE QLLEHGYKVR GTARSASKLA NLQKRWDAKY    60
PGRFETAVVE DQLKQGAYDE VIKGAAGVAH IASVTSFSNK YDEVVTPAIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDGQGQDLSKF DTAPSLEILK SLGRPGWRSI EESIKDLVGS ETA                    343

SEQ ID NO: 167         moltype = DNA  length = 1029
FEATURE                Location/Qualifiers
misc_feature           1..1029
                       note = KRED-101 variant
source                 1..1029
                       mol_type = other DNA
                       organism = synthetic construct
SEQUENCE: 167
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga acgttggga cgctaaaatac   180
ccgggtcgtt tcgaaacctg gttgttgaa gacatgctga acagggtgc ttacgacgaa    240
gttatcaaag tgctgctgg tgttgctcac atcgcttccg ttacatcctt ctccaacaaa    300
tacgacgaag ttgttacccc ggctatcggt ggtaccttga acgctctgcg tgctgctgct   360
gctaccccgt ccgttaaacg tttcgttctg acctcctcca cctttccgc tctggttccg    420
aaaccgaacg ttgaaggtat ctacctggac gaaaaaatcct ggaacctgga atccatcgac   480
aaagctaaaa ccctgccgga atccgaccc cagaaatccc tgtgggtata cgctgcgtcc   540
aagaccgaag ctgaactggc tgcatggaaa tttatgatg agaacaagcc acacttcact    600
ctgaacgctg tactgccaaa ctacactatt ggcactattt tcgatccgga aactcagtcc   660
ggttccacct ccggttggat gatgtccctg tttaacggcg aggttccccc ggctctggct    720
ctgatgccac cgcagtacta cgtttccgct gttgatattg gctgctgca cctgggttgc    780
ctggttctgc cacaaatcga acgtcgtcgt gtttacggta cggctggtac tttcgattgg   840
aacaccgttc tggctacctt ccgtaaactg tacccgtcca aaaccttccc ggctgacttc    900
ccagatcaag tcaggacct gtctaaattc gacaccgctc cgtccctgga aattctgaaa    960
tctctgggtc gccaggttg gcgttccatc gaagaatcca tcaaagacct ggttggttcc   1020
gaaaccgct                                                          1029

SEQ ID NO: 168         moltype = AA  length = 343
FEATURE                Location/Qualifiers
REGION                 1..343
                       note = KRED-101 variant
source                 1..343
                       mol_type = protein
                       organism = synthetic construct
SEQUENCE: 168
MAKIDNAVLP EGSLVLVTGA NGFVGSHVVE QLLEHGYKVR GTARSASKLA NLQKRWDAKY    60
PGRFETWVVE DMLKQGAYDE VIKGAAGVAH IASVTSFSNK YDEVVTPAIG GTLNALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDGQGQDLSKF DTAPSLEILK SLGRPGWRSI EESIKDLVGS ETA                    343
```

```
SEQ ID NO: 169          moltype = DNA  length = 1029
FEATURE                 Location/Qualifiers
misc_feature            1..1029
                        note = KRED-101 variant
source                  1..1029
                        mol_type = other DNA
                        organism = synthetic construct
SEQUENCE: 169
atggcaaaga tcgataacgc agttctgccg gaaggttccc tggttctggt taccggtgct    60
aacggtttcg ttggttccca cgttgttgaa cagctgctgg aacacggtta caaagttcgt   120
ggtaccgctc gttccgcttc caaactggct aacctgcaga aacgttggga cgctaaatac   180
ccgggtcgtt tcgaaaccgc tgttgttgaa gacatgctga acagggtgc ttacgacgaa    240
gttatcaaag gtgctgctgg tgttgctcac atcgcttccg ttacatcctt ctccaacaaa   300
tacgacgaag ttgttacccc ggctatcggt ggtaccttgg ttgctctgcg tgctgctgct   360
gctaccccgt ccgttaaacg tttcgttctg acctcctcca cctttccgc tctggttccg    420
aaaccgaacg ttgaaggtat ctacctggac gaaaaatcct ggaacctgga atccatcgac   480
aaagctaaaa ccctgccgga atccgacccg cagaaatccc tgtgggtata cgctgcgtcc   540
aagaccgaag ctgaactggc tgcatggaaa tttatgdatg agaacaagcc acacttcact   600
ctgaacgctg tactgccaaa ctacactatt ggcactattt tcgatccgga aactcagtcc   660
ggttccacct ccgttggat gatgtccctg tttaacggcg aggttccc ggctctggct     720
ctgatgccac cgcagtacta cgtttccgct gttgatattg gctgctgca cctgggttgc    780
ctggttctgc cacaaatcga acgtcgtcgt gtttacggta ggctggtac tttcgattgg   840
aacaccgttc tggctacctt ccgtaaactg taccgtcca aaaccttccc ggctgacttc     900
ccagatcaag gtcaggacct gtctaaattc gacaccgctc cgtccctgga aattctgaaa   960
tctctgggtc gcccaggttg gcgttccatc gaagaatcca tcaaagacct ggttggttcc  1020
gaaaccgct                                                           1029

SEQ ID NO: 170          moltype = AA  length = 343
FEATURE                 Location/Qualifiers
REGION                  1..343
                        note = KRED-101 variant
source                  1..343
                        mol_type = protein
                        organism = synthetic construct
SEQUENCE: 170
MAKIDNAVLP EGSLVLVTGA NGFVGSHVVE QLLEHGYKVR GTARSASKLA NLQKRWDAKY    60
PGRFETAVVE DMLKQGAYDE VIKGAAGVAH IASVTSFSNK YDEVVTPAIG GTLVALRAAA   120
ATPSVKRFVL TSSTFSALVP KPNVEGIYLD EKSWNLESID KAKTLPESDP QKSLWVYAAS   180
KTEAELAAWK FMDENKPHFT LNAVLPNYTI GTIFDPETQS GSTSGWMMSL FNGEVSPALA   240
LMPPQYYVSA VDIGLLHLGC LVLPQIERRR VYGTAGTFDW NTVLATFRKL YPSKTFPADF   300
PDQGQDLSKF DTAPSLEILK SLGRPGWRSI EESIKDLVGS ETA                     343

SEQ ID NO: 171          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 171
atgctgccga aactcgttat aactcaccga gtacacgaag agatcctgca actgctggcg    60
ccacattgcg agctgataac caaccagacc gacagcacgc tgacgcgcga ggaaattctg   120
cgccgctgtc gcgatgctca ggcgatgatg gcgttcatgc ccgatcgggt cgatgcagac   180
tttcttcaag cctgccctga gctgcgtgta atcggctgcg cgctcaaggg cttcgacaat   240
ttcgatgtgg acgcctgtac tgcccgcggg gtctggctga ccttcgtgcc tgatctgttg   300
acggtcccga ctgccgagct ggcgatcgga ctgggcggtgg ggctggggcg gcatctgcgg   360
gcagcagatg cgttcgtccg ctctggcaag ttccgggct ggcaaccacg gttctacggc    420
acggggctgg ataacgctac ggtcggcttc cttggcatgg cgccatcgg actggccatg    480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctcggta    720
gtggatgaag ccgccgtgct cgcggcgctt gagcgaggcc agctcggcgg gtatgcgcg    780
gatgtattcg aaatggaaga ctgggctcgc gcggaccggc ccagacagat cgatcctgcg   840
ctgctcgcgc atccgaatac gctgttcact ccgcacatag gtcggcagt gcgcgcggtg    900
cgcctggaga ttgaacgttg tgcagcgcag aacatcctcc aggcattggc aggtgagcgc   960
ccaatcaacg ctgtgaaccg tctgcccaag gccgagcctg ccgcatgttg a            1011

SEQ ID NO: 172          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 172
MLPKLVITHR VHEEILQLLA PHCELITNQT DSTLTREEIL RRCRDAQAMM AFMPDRVDAD    60
FLQACPELRV IGCALKGFDN FDVDACTARG VWLTFVPDLL TVPTAELAIG LAVGLGRHLR   120
AADAFVRSGK FRGWQPRFYG TGLDNATVGF LGMGAIGLAM ADRLQGWGAT LQYHARKALD   180
```

```
TQTEQRLGLR QVACSELFAS SDFILLALPL NADTLHLVNA ELLALVRPGA LLVNPCRGSV    240
VDEAAVLAAL ERGQLGGYAA DVFEMEDWAR ADRPQQIDPA LLAHPNTLFT PHIGSAVRAV    300
RLEIERCAAQ NILQALAGER PINAVNRLPK AEPAAC                              336

SEQ ID NO: 173          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 173
atgctgccga aactcgttat aactcacaaa gtacacgaag agatcctgca actgctggcg    60
ccacattgcg agctgataac caaccagacc gacagcacgc tgacgcgcga ggaaattctg    120
cgccgctgtc gcgatgctca ggcgatgatg gcgttcatgc ccgatcgggt cgatgcagac    180
tttcttcaag cctgccctga gctgcgtgta atcggcgctg cgctcaaggg ctttgacaat    240
ttcgatgtgg acgcctgtac tgcccgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcaag ttcggggct ggcaaccaca gttctacggc    420
acggggctgg ataacgctac ggtcggcttc cttggcatgg gcgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcg    660
gagctgcttg ccctcgtacg gccgggcgct ctgcttgtta accccgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag gtcggcagt gcgcgcggtg    900
cgcctggaaa ttgaacgttg cgcagcgcag aacatcctcc aggcattggc aggtgagcgc    960
ccaatcaacg ctgtgaaccg tctgcccaag gccgagcctg ccgcatgttg a            1011

SEQ ID NO: 174          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 174
MLPKLVITHK VHEEILQLLA PHCELITNQT DSTLTREEIL RRCRDAQAMM AFMPDRVDAD    60
FLQACPELRV IGAALKGFDN FDVDACTARG VWLTFVPDLL TVPTAELAIG LAVGLGRHLR    120
AADAFVRSGK FRGWQPQFYG TGLDNATVGF LGMGAIGLAM ADRLQGWGAT LQYHARKALD    180
TQTEQRLGLR QVACSELFAS SDFILLALPL NADTLHLVNA ELLALVRPGA LLVNPCRGSV    240
VDEAAVLAAL ERGQLGGYAA DVFEMEDWAR ADRPQQIDPA LLAHPNTLFT PHIGSAVRAV    300
RLEIERCAAQ NILQALAGER PINAVNRLPK AEPAAC                              336

SEQ ID NO: 175          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 175
atgctgccga aactcgttat aactcacaaa gtacacgaag agatcctgca actgctggcg    60
ccacattgcg agctgataac caaccagacc gacagcacgc tgacgcgcga ggaaattctg    120
cgccgctgtc gcgatgctca ggcgatgatg gcgttcatgc ccgatcgggt cgatgcagac    180
tttcttcaag cctgccctga gctgcgtgta atcggcgctg cgctcaaggg ctatgacaat    240
ttcgatgtgg acgcctgtac tgcccgcggg gtctggctga ccttcgtgcc tgatctgttg    300
acggtcccga ctgccgagct ggccatcgga ctggcggtgg ggctggggcg gcatctgcgg    360
gcagcagatg cgttcgtccg ctctggcaag ttcggggct ggcaaccacg gttctacggc    420
acggggctgg ataacgctac ggtcggcttc cttggcatgg gcgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcg    660
gagctgcttg ccctcgtacg gccgggcgct ctgcttatta ccccgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag gtcggcagt gcgcgcggtg    900
cgcctggaaa ttgaacgttg cgcagcgcag aacatcctcc aggcattggc aggtgagcgc    960
ccaatcgacg ctgtgaaccg tctgcccaag gccgagcctg ccgcatgttg a            1011

SEQ ID NO: 176          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 176
```

```
MLPKLVITHK VHEEILQLLA PHCELITNQT DSTLTREEIL RRCRDAQAMM AFMPDRVDAD    60
FLQACPELRV IGAALKGYDN FDVDACTARG VWLTFVPDLL TVPTAELAIG LAVGLGRHLR   120
AADAFVRSGK FRGWQPRFYG TGLDNATVGF LGMGAIGLAM ADRLQGWGAT LQYHARKALD   180
TQTEQRLGLR QVACSELFAS SDFILLALPL NADTLHLVNA ELLALVRPGA LLINPCRGSV   240
VDEAAVLAAL ERGQLGGYAA DVFEMEDWAR ADRPQQIDPA LLAHPNTLFT PHIGSAVRAV   300
RLEIERCAAQ NILQALAGER PIDAVNRLPK AEPAAC                             336

SEQ ID NO: 177           moltype = DNA   length = 1011
FEATURE                  Location/Qualifiers
misc_feature             1..1011
                         note = PDH-101 variant
source                   1..1011
                         mol_type = other DNA
                         organism = synthetic construct
SEQUENCE: 177
atgctgccga aactcgttat aactcacaga gtacacgaag agatcctgca actgctggcg    60
ccacattgcg agctgataac caaccagacc gacagcacgc tgacgcgcga ggaaattctg   120
cgccgctgtc gcgatgctca ggcgatgatg cgttcatgc ccgatcgggt cgatgcagac   180
tttcttcaag cctgccctga gctgcgtgta atcggctgtg cgctcaaggg ctttgacaat   240
ttcgatgtgg acgcctgtac tgcccgcggg gtctggctga ccttcgtgcc tgatctgttg   300
acggtcccga ctgccgagct ggccatcgga ctggcggtgg gctggggcg gcatctgcgg   360
gcagcagatg cgttcgtccg ctctggcaag ttccggggct ggcaaccaca gttctacgcc   420
acggggctgg ataacgctac ggtcggcttc cttggcatgg gcgccatcgg actggcgcatg   480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata cctgcatct ggtcaacgcc    660
gagctgcttg ccctcgtacg gccgggcgct ctgcttatta accctgtcg tggctcggta   720
gtggatgaag ccgccgtgct cgcggcgctt agcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag gtcggcagt gcgcgcggtg   900
cgcctggcaa ttgaacgttg cgcagcgcag aacatcctcc aggcattggc aggtgagcgc   960
ccaatcgacg ctgcgaaccg tctgcccaag gccgagcctg ccgcatgttg a            1011

SEQ ID NO: 178           moltype = AA   length = 336
FEATURE                  Location/Qualifiers
REGION                   1..336
                         note = PDH-101 variant
source                   1..336
                         mol_type = protein
                         organism = synthetic construct
SEQUENCE: 178
MLPKLVITHR VHEEILQLLA PHCELITNQT DSTLTREEIL RRCRDAQAMM AFMPDRVDAD    60
FLQACPELRV IGCALKGFDN FDVDACTARG VWLTFVPDLL TVPTAELAIG LAVGLGRHLR   120
AADAFVRSGK FRGWQPQFYG TGLDNATVGF LGMGAIGLAM ADRLQGWGAT LQYHARKALD   180
TQTEQRLGLR QVACSELFAS SDFILLALPL NADTLHLVNA ELLALVRPGA LLINPCRGSV   240
VDEAAVLAAL ERGQLGGYAA DVFEMEDWAR ADRPQQIDPA LLAHPNTLFT PHIGSAVRAV   300
RLAIERCAAQ NILQALAGER PIDAVNRLPK AEPAAC                             336

SEQ ID NO: 179           moltype = DNA   length = 1011
FEATURE                  Location/Qualifiers
misc_feature             1..1011
                         note = PDH-101 variant
source                   1..1011
                         mol_type = other DNA
                         organism = synthetic construct
SEQUENCE: 179
atgctgccga aactcgttat aactcacaaa gtacacgaag agatcctgca actgctggcg    60
ccacattgcg agctgataac caaccagacc gacagcacgc tgacgcgcga ggaaattctg   120
cgccgctgtc gcgatgctca ggcgatgatg cgttcatgc ccgatcgggt cgatgcagac   180
tttcttcaag cctgccctga gctgcgtgta atcggctgtg cgctcaaggg ctattgacaat   240
ttcgatgtgg acgcctgtac tgcccgcggg gtctggctga ccttcgtgcc tgatctgttg   300
acggtcccga ctgccgagct ggcgatcgga ctggcggtgg gctggggcg gcatctgcgg   360
gcagcagatg cgttcgtccg ctctggcaag ttccggggct ggcaaccaca gttctacggc   420
acggggctgg ataacgctac ggtcggcttc cttggcatgg gcgccatcgg actggcgcatg   480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata cctgcatct ggtcaacgcc    660
gagctgcttg ccctcgtacg gccgggcgct ctgcttgtaa accctgtcg tggctcggta    720
gtggatgaag ccgccgtgct cgcggcgctt agcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag gtcggcagt gcgcgcggtg    900
cgcctggaga ttgaacgttg tgcagcgcag aacatcctcc aggcattggc aggtgagcgc   960
ccaatcgacg ctgcgaaccg tctgcccaag gccgagcctg ccgcatgttg a            1011

SEQ ID NO: 180           moltype = AA   length = 336
FEATURE                  Location/Qualifiers
REGION                   1..336
                         note = PDH-101 variant
source                   1..336
```

```
                        mol_type = protein
                        organism = synthetic construct
SEQUENCE: 180
MLPKLVITHK VHEEILQLLA PHCELITNQT DSTLTREEIL RRCRDAQAMM AFMPDRVDAD    60
FLQACPELRV IGAALKGYDN FDVDACTARG VWLTFVPDLL TVPTAELAIG LAVGLGRHLR   120
AADAFVRSGK FRGWQPQFYG TGLDNATVGF LGMGAIGLAM ADRLQGWGAT LQYHARKALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHIGSAVRAV   300
RLEIERCAAQ NILQALAGER PIDAANRLPK AEPAAC                             336

SEQ ID NO: 181          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 181
atgctgccga aactcgttat aactcaccga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgcg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg gctggggcg gcatctgcgg     360
gcagcagatg cgttcgtccg ctctggcaag ttccagggct ggcaaccacg gttctacggg   420
acggggctga atggagctac ggtcggcttc cttggcatgg cgccatcgg actggccatg    480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag gtcggcagt gcgcgcggtg    900
cgcctggaga ttgaacgttg tgcagcgcag aacatcctcc aggcattggc aggtgagcgc   960
ccaattaacg ctgtgaaccg tctgcccaag gccgagcctg ccgcatgttg a            1011

SEQ ID NO: 182          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 182
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHLR   120
AADAFVRSGK FQGWQPRFYG TGLDGATVGF LGMGAIGLAM ADRLQGWGAT LQYHARKALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHIGSAVRAV   300
RLEIERCAAQ NILQALAGER PINAVNRLPK AEPAAC                             336

SEQ ID NO: 183          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 183
atgctgccga aactcgttat aactcaccga gtacacgatg agatcctgca actgctggcg     60
ccacattgcg agctgataac caaccagacc gacagcacgc tgacgcgcga ggaaattctg    120
gcacgctgtc gggatgctca ggcgatgatg gcgttcatgc ccgatcgggt cgatgcagat    180
tttcttgctg cctgccctga gctgcgtgta atcggctgcg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg gctggggcg gcatctgcgg     360
gcagcagatg cgttcgtccg ctctggcaag ttccagggct ggcaaccacg gttctacggc   420
acggggctga taacgctac ggtcggcttc cttggcatgg cgccatcgg actggccatg     480
gctgatcgct tgcagggatg gggcgcgacc ctgcagtacc acgcgcggaa ggctctggat   540
acacaaaccg agcaacggct cggcctgcgc caggtgtcgt gcagcgaagaact cttcgccagc 600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag gtcggcagt gcgcgcggtg    900
cgcctggaga ttgaacgttg tgcagcgcag aacatcctcc aggcattggc aggtgagcgc   960
ccaatcaacg ctgtgaaccg tctgcccaag gccgagcctg ccgcatgttg a            1011

SEQ ID NO: 184          moltype = AA  length = 336
FEATURE                 Location/Qualifiers
```

```
REGION                     1..336
                           note = PDH-101 variant
source                     1..336
                           mol_type = protein
                           organism = synthetic construct
SEQUENCE: 184
MLPKLVITHR VHDEILQLLA PHCELITNQT DSTLTREEIL ARCRDAQAMM AFMPDRVDAD    60
FLAACPELRV IGCALKGFDN FDVDACTARG VWLTFVPDLL TVPTAELAIG LAVGLGRHLR   120
AADAFVRSGK FQGWQPRFYG TGLDNATVGF LGMGAIGLAM ADRLQGWGAT LQYHARKALD   180
TQTEQRLGLR QVSCEELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHIGSAVRAV   300
RLEIERCAAQ NILQALAGER PINAVNRLPK AEPAAC                             336

SEQ ID NO: 185             moltype = DNA  length = 1011
FEATURE                    Location/Qualifiers
misc_feature               1..1011
                           note = PDH-101 variant
source                     1..1011
                           mol_type = other DNA
                           organism = synthetic construct
SEQUENCE: 185
atgctgccga aactcgttat aactcaccga gtacacgaag agatcctgca actgctggcg    60
ccacattgcg agctgataac caaccagacc gacagcacgc tgacgcgcga ggaaattctg   120
gcacgctgtg cagatgctca ggcgatgatg gcgttcatgc cgatcgggt cgatgcagat   180
tttcttcagg cctgccctga gctgcgtgta atcggctgcg cgctcaaggg cttcgacaat   240
ttcgatgtgg acgcctgtac tcggcgcggg gtctggctga ccttcgtgcc tgatctgttg   300
acggtcccga ctgccgagct ggcgatcgga ctggcggtgg gctgggcg catctgcgg    360
gcagcagatg cgttcgtccg ctctggcaag ttccggggct ggcaaccacg gttctacggc   420
acggggctgg ataacgctac ggtcggcttc cttggcatgg gcgccatcgg actggccatg   480
gctgatcgct tgcagggatg gggcgcgacc ctgcagtacc acgcgcggaa ggctctggat   540
acacaaaccg agcaacggct cggcctgcgc caggtgtcgt gcgaagaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta   720
gtggatgaag ccgccgtgct cgcggcgctt gagcgaggcc agtcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag gtcggcagt gcgcgcggtg   900
cgcctggaga ttgaacgttg tgcagcgcag aacatcctcc aggcattggc aggtgagcgc   960
ccaatcaacg ctgtgaaccg tctgcccaag gccgagcctg ccgcatgttg a           1011

SEQ ID NO: 186             moltype = AA  length = 336
FEATURE                    Location/Qualifiers
REGION                     1..336
                           note = PDH-101 variant
source                     1..336
                           mol_type = protein
                           organism = synthetic construct
SEQUENCE: 186
MLPKLVITHR VHEEILQLLA PHCELITNQT DSTLTREEIL ARCADAQAMM AFMPDRVDAD    60
FLQACPELRV IGCALKGFDN FDVDACTRRG VWLTFVPDLL TVPTAELAIG LAVGLGRHLR   120
AADAFVRSGK FRGWQPRFYG TGLDNATVGF LGMGAIGLAM ADRLQGWGAT LQYHARKALD   180
TQTEQRLGLR QVSCEELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHIGSAVRAV   300
RLEIERCAAQ NILQALAGER PINAVNRLPK AEPAAC                             336

SEQ ID NO: 187             moltype = DNA  length = 1011
FEATURE                    Location/Qualifiers
misc_feature               1..1011
                           note = PDH-101 variant
source                     1..1011
                           mol_type = other DNA
                           organism = synthetic construct
SEQUENCE: 187
atgctgccga aactcgttat aactcaccga gtacacgaag agatcctgca actgctggcg    60
ccacattgcg agctgataac caaccagacc gacagcacgc tgacgcgcga ggaaattctg   120
cgccgctgtc gcgatgctca ggcgatgatg gcgttcatgc cgatcgggt cgatgcagac   180
tttcttcaag cctgccctga gctgcgtgta atcggctgcg cgctcaaggg cttcgacaat   240
ttcgatgtgg acgcctgtac tgcccgcggg gtctggctga ccttcgtgcc tgatctgttg   300
acggtcccga ctgccgagct ggcgatcgga ctggcggtgg gctgggcg catctgcgg    360
gcagcagatg cgttcgtccg ctctggcaag ttccggggct ggcaaccacg gttctacggc   420
acggggctgg ataacgctac ggtcggcttc cttggcatgg gcgccatcgg actggccatg   480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta   720
gtggatgaag ccgccgtgct cgcggcgctt gagcgaggcc agtcggcgg gtatgcggcg   780
gatgtattcg aaatggttga ctgggctcgc gcggaccggc cgcagcagat cgatcctgcg   840
ctgctcgcgc atccgaatac gctgttcact ccgcacatag gtcggcagt gcgcgcggtg   900
cgcctggaga ttgaacgttg tgcagcgcag aacatcctcc aggcattggc aggtgagcgc   960
ccaatcaacg ctgtgaaccg tctgcccaag gccgagcctg ccgcatgttg a           1011
```

```
SEQ ID NO: 188           moltype = AA  length = 336
FEATURE                  Location/Qualifiers
REGION                   1..336
                         note = PDH-101 variant
source                   1..336
                         mol_type = protein
                         organism = synthetic construct
SEQUENCE: 188
MLPKLVITHR VHEEILQLLA PHCELITNQT DSTLTREEIL RRCRDAQAMM AFMPDRVDAD   60
FLQACPELRV IGCALKGFDN FDVDACTARG VWLTFVPDLL TVPTAELAIG LAVGLGRHLR  120
AADAFVRSGK FRGWQPRFYG TGLDNATVGF LGMGAIGLAM ADRLQGWGAT LQYHARKALD  180
TQTEQRLGLR QVACSELFAS SDFILLALPL NADTLHLVNA ELLALVRPGA LLVNPCRGSV  240
VDEAAVLAAL ERGQLGGYAA DVFEMVDWAR ADRPQQIDPA LLAHPNTLFT PHIGSAVRAV  300
RLEIERCAAQ NILQALAGER PINAVNRLPK AEPAAC                            336

SEQ ID NO: 189           moltype = DNA  length = 1011
FEATURE                  Location/Qualifiers
misc_feature             1..1011
                         note = PDH-101 variant
source                   1..1011
                         mol_type = other DNA
                         organism = synthetic construct
SEQUENCE: 189
atgctgccga aactcgttat aactcaccga gtacacgaag agatcctgca actgctggcg    60
ccacattgcg agctgataac caaccagacc gacagcacgc tgacgcgcga ggaaattctg   120
cgccgctgtc gcgatgctca ggcgatgatg gcgttcatgc ccgatcgggt cgatgcagac   180
tttcttcaag cctgccctga gctgcgtgta atcggctgcg cgctcaaggg cttcgacaat   240
ttcgatgtgg acgcctgtac tgcccgcggg gtctggctga ccttcgtgcc tgatctgttg   300
acggtcccga ctgccgagct ggcgatcgga ctggcggtgg ggctggggcg gcatctgcgg   360
gcagcagatg cgttcgtccg ctctggcaag ttccggggct ggcaaccacg gttctacggc   420
acggggctgg ataacgctac ggtcggcttc cttggcatgg gcgccatcgg actggccatg   480
gctgatcgct tgcagggatg gggcgcgacc ctgcagtacc acgcgcggaa ggctctggat  540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta    720
gtggatgaag ccgccgtgct cgcggcgctt gagcgaggcc agctcggcgg gtatgcggcg   780
gatgtattcg aaatgtggga ctgggctcgc gcggaccggc cgcagcagat cgatcctgcg   840
ctgctcgcgc atccgaatac gctgttcact ccgcacatag gtcggcagt gcgcgcggtg    900
cgcctggaga ttgaacgttg tgcagcgcag aacatcctcc aggcattggc aggtgagcgc   960
ccaatcaacg ctgtgaaccg tctgcccaag gccgagcctg ccgcatgtta a           1011

SEQ ID NO: 190           moltype = AA  length = 336
FEATURE                  Location/Qualifiers
REGION                   1..336
                         note = PDH-101 variant
source                   1..336
                         mol_type = protein
                         organism = synthetic construct
SEQUENCE: 190
MLPKLVITHR VHEEILQLLA PHCELITNQT DSTLTREEIL RRCRDAQAMM AFMPDRVDAD   60
FLQACPELRV IGCALKGFDN FDVDACTARG VWLTFVPDLL TVPTAELAIG LAVGLGRHLR  120
AADAFVRSGK FRGWQPRFYG TGLDNATVGF LGMGAIGLAM ADRLQGWGAT LQYHARKALD  180
TQTEQRLGLR QVACSELFAS SDFILLALPL NADTLHLVNA ELLALVRPGA LLVNPCRGSV  240
VDEAAVLAAL ERGQLGGYAA DVFEMWDWAR ADRPQQIDPA LLAHPNTLFT PHIGSAVRAV  300
RLEIERCAAQ NILQALAGER PINAVNRLPK AEPAAC                            336

SEQ ID NO: 191           moltype = DNA  length = 1011
FEATURE                  Location/Qualifiers
misc_feature             1..1011
                         note = PDH-101 variant
source                   1..1011
                         mol_type = other DNA
                         organism = synthetic construct
SEQUENCE: 191
atgctgccga aactcgttat aactcaccga gtacacgaag agatcctgca actgctggcg    60
ccacattgcg agctgataac caaccagacc gacagcacgc tgacgcgcga ggaaattctg   120
cgccgctgtc gcgatgctca ggcgatgatg gcgttcatgc ccgatcgggt cgatgcagac   180
tttcttcaag cctgccctga gctgcgtgta atcggctgcg cgctcaaggg cttcgacaat   240
ttcgatgtgg acgcctgtac tgcccgcggg gtctggctga ccttcgtgcc tgatctgttg   300
acggtcccga ctgccgagct ggcgatcgga ctggcggtgg ggctggggcg gcatctgcgg   360
gcagcagatg cgttcgtccg ctctggcaag ttccggggct ggcaaccacg gttctacggc   420
acggggctgg ataacgctac ggtcggcttc cttggcatgg gcgccatcgg actggccatg   480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta    720
gtggatgaag ccgccgtgct cgcggcgctt gagcgaggcc agctcggcgg gtatgcggcg   780
gatgtattcg aaatgtctga ctgggctcgc gcggaccggc cgcagcagat cgatcctgcg   840
```

```
ctgctcgcgc atccgaatac gctgttcact ccgcacatag ggtcggcagt gcgcgcggtg    900
cgcctggaga ttgaacgttg tgcagcgcag aacatcctcc aggcattggc aggtgagcgc    960
ccaatcaacg ctgtgaaccg tctgcccaag gccgagcctg ccgcatgttg a            1011

SEQ ID NO: 192        moltype = AA    length = 336
FEATURE               Location/Qualifiers
REGION                1..336
                      note = PDH-101 variant
source                1..336
                      mol_type = protein
                      organism = synthetic construct
SEQUENCE: 192
MLPKLVITHR VHEEILQLLA PHCELITNQT DSTLTREEIL RRCRDAQAMM AFMPDRVDAD     60
FLQACPELRV IGCALKGFDN FDVDACTARG VWLTFVPDLL TVPTAELAIG LAVGLGRHLR    120
AADAFVRSGK FRGWQPRFYG TGLDNATVGF LGMGAIGLAM ADRLQGWGAT LQYHARKALD    180
TQTEQRLGLR QVACSELFAS SDFILLALPL NADTLHLVNA ELLALVRPGA LLVNPCRGSV    240
VDEAAVLAAL ERGQLGGYAA DVFEMSDWAR ADRPQQIDPA LLAHPNTLFT PHIGSAVRAV    300
RLEIERCAAQ NILQALAGER PINAVNRLPK AEPAAC                             336

SEQ ID NO: 193        moltype = DNA    length = 1011
FEATURE               Location/Qualifiers
misc_feature          1..1011
                      note = PDH-101 variant
source                1..1011
                      mol_type = other DNA
                      organism = synthetic construct
SEQUENCE: 193
atgctgccga aactcgttat aactcaccga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc cgatcgggt cgatgcagac    180
tttcttcaag cctgccctga gctgcgtgta atcggctgcg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcgtgg ggctggggcg gcatctgcgg    360
gcagcagatg cgttcgtccg ctctggcaag ttccagggct ggcaggacca gttctacggc    420
acggggctgg atgagctac ggtcggcttc cttggcatgg gcgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtta accctgtcg tggctcggta    720
gtggatgaag ccgccgtgct cgcggcgctt gagcgaggcc agtcggcgg gtatgcggcc    780
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcggcgcag aacatcctcc aggcattggc aggtgagcgc    960
ccaattaacg ctgtgaaccg tctgcccaag gccgagcctg ccgcatgttg a            1011

SEQ ID NO: 194        moltype = AA    length = 336
FEATURE               Location/Qualifiers
REGION                1..336
                      note = PDH-101 variant
source                1..336
                      mol_type = protein
                      organism = synthetic construct
SEQUENCE: 194
MLPKLVITHR VHEEILQLLA PHCELITNQT DSTLTREEIL RRCADAQAMM AFMPDRVDAD     60
FLQACPELRV IGCALKGFDN FDVDACTARG VWLTFVPDLL TVPTAELAIG LAVGLGRHLR    120
AADAFVRSGK FQGWQDQFYG TGLDGATVGF LGMGAIGLAM ADRLQGWGAT LQYHARKALD    180
TQTEQRLGLR QVACSELFAS SDFILLALPL NADTLHLVNA ELLALVRPGA LLVNPCRGSV    240
VDEAAVLAAL ERGQLGGYAA DVFEMEDWAR ADRPQQIDPA LLAHPNTLFT PHLGSAVRAV    300
RLEIERCAAQ NILQALAGER PINAVNRLPK AEPAAC                             336

SEQ ID NO: 195        moltype = DNA    length = 1011
FEATURE               Location/Qualifiers
misc_feature          1..1011
                      note = PDH-101 variant
source                1..1011
                      mol_type = other DNA
                      organism = synthetic construct
SEQUENCE: 195
atgctgccga aactcgttat aactcaccga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc cgatcgggt cgatgcagac    180
tttcttcaag cctgccctga gctgcgtgta atcggctgcg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcgtgg ggctggggcg gcatctgcgg    360
gcagcagatg cgttcgtccg ctctggcaag ttccagggct ggcagccaat tttctacggc    420
acggggctgg atgagctac ggtcggcttc cttggcatgg gcgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
```

```
gagctgcttg ccctcgtacg gccgggcgct ctgcttatta accccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcacatag ggtcggcagt gcgcgcggtg    900
cgcctggaga ttgaacgttg tgtggcgcag aacatcctcc aggcattggc aggtgagcgc    960
ccaattgacg ctgtgaaccg tctgcccaag gccgagcctg ccgcatgttg a             1011

SEQ ID NO: 196          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 196
MLPKLVITHR VHEEILQLLA PHCELITNQT DSTLTREEIL RRCADAQAMM AFMPDRVDAD     60
FLQACPELRV IGCALKGFDN FDVDACTARG VWLTFVPDLL TVPTAELAIG LAVGLGRHLR    120
AADAFVRSGK FQGWQPIFYG TGLDGATVGF LGMGAIGLAM ADRLQGWGAT LQYHARKALD    180
TQTEQRLGLR QVACSELFAS SDFILLALPL NADTLHLVNA ELLALVRPGA LLINPCRGSV    240
VDEAAVLAAL ERGQLGGYAA DVFEMEDWAR ADRPQQIDPA LLAHPNTLFT PHIGSAVRAV    300
RLEIERCVAQ NILQALAGER PIDAVNRLPK AEPAAC                              336

SEQ ID NO: 197          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 197
atgctgccga aactcgttat aactcaccga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgcg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcaag ttccagggct gggctgacat tttctacggc    420
acggggctgg atggagctac ggtcggcttc cttggcatgg gcgccatcgg actggccatg    480
gctgatcgct tgcagggatg gggcgcgacc ctgcagtacc acgcgcggaa ggctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtta accccctgtcg tggctcggta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattggc aggtgagcgc    960
ccaattaacg ctgtgaaccg tctgcccaag gccgagcctg ccgcatgttg a             1011

SEQ ID NO: 198          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 198
MLPKLVITHR VHEEILQLLA PHCELITNQT DSTLTREEIL RRCADAQAMM AFMPDRVDAD     60
FLQACPELRV IGCALKGFDN FDVDACTARG VWLTFVPDLL TVPTAELAIG LAVGLGRHLR    120
AADAFVRSGK FQGWADIFYG TGLDGATVGF LGMGAIGLAM ADRLQGWGAT LQYHARKALD    180
TQTEQRLGLR QVACSELFAS SDFILLALPL NADTLHLVNA ELLALVRPGA LLVNPCRGSV    240
VDEAAVLAAL ERGQLGGYAA DVFEMEDWAR ADRPQQIDPA LLAHPNTLFT PHLGSAVRAV    300
RLEIERCAAQ NILQALAGER PINAVNRLPK AEPAAC                              336

SEQ ID NO: 199          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 199
atgctgccga aactcgttat aactcacaga gtacacgaag agatcctgca actgctggcg     60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcaag ttccagggct ggcagccaat tttctacggc    420
acggggctgg atggagctac ggtcggcttc cttggcatgg gcgccatcgg actggccatg    480
```

```
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agtcggcgg gtatgcggcg    780
gatgtattcg aaatggaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattggc aggtgagcgc   960
ccaattgacg ctgtgaaccg tctgcccaag gccgagcctg ccgcatgttg a            1011

SEQ ID NO: 200          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 200
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHLR   120
AADAFVRSGK FQGWQPIFYG TGLDGATVGF LGMGAIGLAM ADRLQGWGAT LQYHARKALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALAGER PIDAVNRLPK AEPAAC                             336

SEQ ID NO: 201          moltype = DNA   length = 1011
FEATURE                 Location/Qualifiers
misc_feature            1..1011
                        note = PDH-101 variant
source                  1..1011
                        mol_type = other DNA
                        organism = synthetic construct
SEQUENCE: 201
atgctgccga aactcgttat aactcaccga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgcg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcgggtg gctggggcg catctcgagg   360
gcagcagatg cgttcgtccg ctctggcaag ttccagggct ggcaaccacg gttctacggc   420
acggggctgg atggagctac ggtcggcttc cttggcatgg gcgccatcgg actgccatg    480
gctgatcgct tgcagggatg gggcgcgacc ctgcagtacc acgcgcggaa ggctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtta accctgtcg tggctcggta    720
gtggatgaag ccgccgtgct cgcggcgctt gagcgaggcc agtcggcgg gtatgcggcg    780
gatgtattcg aaatggaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattggc aggtgagcgc   960
ccaattgacg ctgtgaaccg tctgcccaag gccgagcctg ccgcatgttg a            1011

SEQ ID NO: 202          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 202
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHLR   120
AADAFVRSGK FQGWQPRFYG TGLDGATVGF LGMGAIGLAM ADRLQGWGAT LQYHARKALD   180
TQTEQRLGLR QVACEELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALAGER PIDAVNRLPK AEPAAC                             336

SEQ ID NO: 203          moltype = DNA   length = 1011
FEATURE                 Location/Qualifiers
misc_feature            1..1011
                        note = PDH-101 variant
source                  1..1011
                        mol_type = other DNA
                        organism = synthetic construct
SEQUENCE: 203
atgctgccga aactcgttat aactcaccga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgcg cgctcaaggg cttcgacaat   240
ttcgatgtgg acgcctgtac tgcacgcggg gtctggctga ccttcgtgcc tgatctgttg   300
```

```
acggtcccga ctgccgagct ggcgatcgga ctggcgtcgg ggctggggcg gcatctgcgg   360
gcagcagatg cgttcgtccg ctctggcaag ttccagggct ggcaaccacg gttctacggc   420
acggggctgg atggagctac ggtcggcttc cttggcatgg cgccatcgg actggccatg    480
gctgatcgct tgcagggatg gggcgcgacc ctgcagtacc acgcgcggaa ggctctggat   540
acacaaaccg agcaacggct cggcctgcgc caggtgcgt gcagcgaact cttcgccagc    600
tcggacttca tcctgctggc gcttcccttg aatgccgata ccctgcatct ggtcaacgcc   660
gagctgcttg ccctcgtacg gccgggcgct ctgcttgtaa accccgtcg tggctcggta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcacatag ggtcggcagt gcgcgcggtg   900
cgcctggaga ttgaacgttg tgcagcgcag aacatcctcc aggcattggc aggtgagcgc   960
ccaattaacg ctgtgaaccg tctgcccaag gccgagcctg ccgcatgttg a            1011

SEQ ID NO: 204        moltype = AA   length = 336
FEATURE               Location/Qualifiers
REGION                1..336
                      note = PDH-101 variant
source                1..336
                      mol_type = protein
                      organism = synthetic construct
SEQUENCE: 204
MLPKLVITHR VHEEILQLLA PHCELITNQT DSTLTREEIL RRCADAQAMM AFMPDRVDAD   60
FLQACPELRV IGCALKGFDN FDVDACTARG VWLTFVPDLL TVPTAELAIG LASGLGRHLR  120
AADAFVRSGK FQGWQPRFYG TGLDATVGF LGMGAIGLAM ADRLQGWGAT LQYHARKALD   180
TQTEQRLGLR QVACSELFAS SDFILLALPL NADTLHLVNA ELLALVRPGA LLVNPCRGSV  240
VDEAAVLAAL ERGQLGGYAA DVFEMEDWAR ADRPQQIDPA LLAHPNTLFT PHIGSAVRAV  300
RLEIERCAAQ NILQALAGER PINAVNRLPK AEPAAC                           336

SEQ ID NO: 205        moltype = DNA   length = 1011
FEATURE               Location/Qualifiers
misc_feature          1..1011
                      note = PDH-101 variant
source                1..1011
                      mol_type = other DNA
                      organism = synthetic construct
SEQUENCE: 205
atgctgccga aactcgttat aactcacaga gtacacgaag agatcctgca aatgctggcg   60
ccacattgcg agctgataac caaccagacc gacagcacgc tgacgcgcga ggaaattctg  120
cggcgctgtg cagatgctca ggcgatgatg cgttcatcc ccgatcgggt cgatgcagac   180
tttcttcaag cctgccctga gctgcgtgta atcggctgtg cgctcaaggg cttcgacaat  240
ttcgatgtgg acgcctgtac tgcacgcggg gtctggctga ccttcgtgcc tgatctgttg  300
acggtcccga ctgccgagct ggcgatcgga ctggcgtgg ggctggggcg gcatttccgg   360
gcagcagatg aattcgtccg ctctggcaag ttccagggct ggcagccaat tttctacggc  420
acggggctgg atggagcaac ggtcggcttc cttggcatgg cgccatcgg actcgccatg   480
gctgatcgct tgcagggatg gggcgcgacc ctgcagtacc acgcgcggaa ggctctggat  540
acacaaaccg agcaacggct cggcctgcgc caggtggcgt gcagcgaact cttcgccagc  600
tcggacttca tcctgctggc gcttcccttg aatgccgata ccctgcatct ggtcaacgcc  660
gagctgcttg ccctcgtacg gccgggcgct ctgcttgtaa accccgtcg tggctcggta   720
gtggatgaag ccgccgtgct cgcggcgctt gagcgaggcc agctcggcgg gtatgcggcg  780
gatgtattcg aaatggaaga ctgggctcgc gcggaccggc cgcagcagat cgatcctgcg  840
ctgctcgcgc atccgaatac gctgttcact ccgcaccttg ggtcggcagt gcgcgcggtg  900
cgcctggaga ttgaacgttg tgcagcgcag aacatcctcc aggcattggc aggtgagcgc  960
ccaattgacg ctgtgaaccg tctgcccaag gccgagccca aggcccgctg a           1011

SEQ ID NO: 206        moltype = AA   length = 336
FEATURE               Location/Qualifiers
REGION                1..336
                      note = PDH-101 variant
source                1..336
                      mol_type = protein
                      organism = synthetic construct
SEQUENCE: 206
MLPKLVITHR VHEEILQMLA PHCELITNQT DSTLTREEIL RRCADAQAMM AFMPDRVDAD   60
FLQACPELRV IGCALKGFDN FDVDACTARG VWLTFVPDLL TVPTAELAIG LAVGLGRHFR  120
AADEFVRSGK FQGWQPIFYG TGLDATVGF LGMGAIGLAM ADRLQGWGAT LQYHARKALD   180
TQTEQRLGLR QVACSELFAS SDFILLALPL NADTLHLVNA ELLALVRPGA LLVNPCRGSV  240
VDEAAVLAAL ERGQLGGYAA DVFEMEDWAR ADRPQQIDPA LLAHPNTLFT PHLGSAVRAV  300
RLEIERCAAQ NILQALAGER PIDAVNRLPK AEPKAR                           336

SEQ ID NO: 207        moltype = DNA   length = 1011
FEATURE               Location/Qualifiers
misc_feature          1..1011
                      note = PDH-101 variant
source                1..1011
                      mol_type = other DNA
                      organism = synthetic construct
SEQUENCE: 207
atgctgccga aactcgttat aactcacaga gtacacgaag agatcctgca actgctggcg   60
ccacattgcg agctgataac caaccagacc gacagcacgc tgacgcgcga ggaaattctg  120
```

```
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcgtgg ggctgggcg gcatttccgg     360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg aatgccgata ccctgcatct ggtcaacgcc    660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggca    780
gatgtattcg aaatggaaga ctgggctcgc gcggaccggc cgcagcagat cgatcctgcg    840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctc ccgcatgttg a            1011

SEQ ID NO: 208          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 208
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                            336

SEQ ID NO: 209          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 209
atgctgccga aactcgttat aactcacaga gtacacgaag agatcctgca aatgctggcg     60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcgtgg ggctgggcg gcatttccgg    360
gcagcagatg aattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc acgcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggca   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattggc aggtgagcgc   960
ccaattgacg ctgtgaaccg tctgcccaag gccgagcctc ccgcatgttg a            1011

SEQ ID NO: 210          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 210
MLPKLVITHR VHEEILQMLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADEFVRSGK FQGWQPIFYG TGLDGATVGF LGMGAIGKAM ADRLQGWGAT LQYHARTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALAGER PIDAVNRLPK AEPAAC                            336

SEQ ID NO: 211          moltype = DNA  length = 1011
FEATURE                 Location/Qualifiers
misc_feature            1..1011
                        note = PDH-101 variant
source                  1..1011
                        mol_type = other DNA
                        organism = synthetic construct
```

```
SEQUENCE: 211
atgctgccga aactcgttat aactcacaga gtacacgaag agatcctgca aatgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg ggctggggcg gcatttccgg   360
gcagcagatg aattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctcgcg caggtggcgt gcagtgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a            1011

SEQ ID NO: 212            moltype = AA  length = 336
FEATURE                   Location/Qualifiers
REGION                    1..336
                          note = PDH-101 variant
source                    1..336
                          mol_type = protein
                          organism = synthetic construct
SEQUENCE: 212
MLPKLVITHR VHEEILQMLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADEFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 213            moltype = DNA  length = 1011
FEATURE                   Location/Qualifiers
misc_feature              1..1011
                          note = PDH-101 variant
source                    1..1011
                          mol_type = other DNA
                          organism = synthetic construct
SEQUENCE: 213
atgctgccga aactcgttat aactcacaga gtacacgaag agatcctgca actgctggcg    60
ccacattgcg agctgataac caaccagacc gactcgacgc tgacgcgcga ggaaattctg   120
cggcgctgtg cagatgctca ggcgatgatg gcgttcatgc ccgatcgggt cgatgcagac   180
tttcttcaag cctgccctga gctgaaagta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg ggctggggcg gcatctggtt   360
gcagcagatg cgttcgtccg ctctggcaag ttccagggct ggcagccaat tttctacggc   420
acggggctgg atggagctac ggtcggcttc cttggcatgg gcgccatcgg actggccatg   480
gctgatcgct tgcagggatg gggcgcgacc ctgcagtacc acacccgaa ggctctggat    540
acacaaaccg agcaacggct cggcctcgcg caggtggcgt gcgaggaact cttcgccagc   600
tcggacttca tcctgctggc gcttcccttg aatgccgata ccctgcatct ggtcaacgcc   660
gagctgcttg ccctcgtacg gccgggcgct ctgcttgtta accctgtcg tggctctgta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattggc aggtgagcgc   960
ccaattgacg ctgtgaaccg tctgcccaag gccgagcctg ccgcatgttg a             1011

SEQ ID NO: 214            moltype = AA  length = 336
FEATURE                   Location/Qualifiers
REGION                    1..336
                          note = PDH-101 variant
source                    1..336
                          mol_type = protein
                          organism = synthetic construct
SEQUENCE: 214
MLPKLVITHR VHEEILQLLA PHCELITNQT DSTLTREEIL RRCADAQAMM AFMPDRVDAD    60
FLQACPELKV IGCALKGFDN FDVDACTARG VWLTFVPDLL TVPTAELAIG LAVGLGRHLV   120
AADAFVRSGK FQGWQPIFYG TGLDGATVGF LGMGAIGLAM ADRLQGWGAT LQYHTRKALD   180
TQTEQRLGLR QVACEELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALAGER PIDAVNRLPK AEPAAC                             336

SEQ ID NO: 215            moltype = DNA  length = 1011
FEATURE                   Location/Qualifiers
misc_feature              1..1011
                          note = PDH-101 variant
```

```
source                  1..1011
                        mol_type = other DNA
                        organism = synthetic construct
SEQUENCE: 215
atgctgccga aactcgttat aactcacaga gtacacgaag agatcctgca actgctggcg    60
ccacattgcg agctgataac caaccagacc gacgtcacgc tgacgcgcga ggaaattctg   120
cggcgctgtg cagatgctca ggcgatgatg gcgttcatgc ccgatcgggt cgatgcagac   180
tttcttcaag cctgccctga gctgagagta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg ggctggggcg gcatctcgcg   360
gcagcagatg cgttcgtccg ctctggcaag ttccagggct ggcagccaat tttctacggc   420
acggggctgg atggagctac ggtcggcttc cttggcatgg gcgccatcgg actgccatg    480
gctgatcgct tgcagggatg gggcgcgacc ctgcagtacc acgcccggaa ggctctggat   540
acacaaactg agcaaaccct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg tccgggcgct ctgcttatta cccctgtcgt ggctctgta   720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattggc aggtgagcgc   960
ccaattgacg ctgtgaaccg tctgcccaag gccgagcctg ccgcaagctg a           1011

SEQ ID NO: 216           moltype = AA   length = 336
FEATURE                  Location/Qualifiers
REGION                   1..336
                         note = PDH-101 variant
source                   1..336
                         mol_type = protein
                         organism = synthetic construct
SEQUENCE: 216
MLPKLVITHR VHEEILQLLA PHCELITNQT DVTLTREEIL RRCADAQAMM AFMPDRVDAD    60
FLQACPELRV IGCALKGFDN FDVDACTARG VWLTFVPDLL TVPTAELAIG LAVGLGRHLR   120
AADAFVRSGK FQGWQPIFYG TGLDGATVGF LGMGAIGLAM ADRLQGWGAT LQYHARKALD   180
TQTEQTLGLR QVACSELFAS SDFILLALPL NADTLHLVNA ELLAHVRPGA LLINPCRGSV   240
VDEAAVLAAL ERGQLGGYAA DVFEMEDWAR ADRPQQIDPA LLAHPNTLFT PHLGSAVRAV   300
RLEIERCAAQ NILQALAGER PIDAVNRLPK AEPAAS                             336

SEQ ID NO: 217           moltype = DNA   length = 1011
FEATURE                  Location/Qualifiers
misc_feature             1..1011
                         note = PDH-101 variant
source                   1..1011
                         mol_type = other DNA
                         organism = synthetic construct
SEQUENCE: 217
atgctgccga aactcgttat aactcacaga gtacacgaag agatcctgca actgctggcg    60
ccacattgcg agctgataac caaccagacc gacagcgcgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg ctatgacaat   240
ttcgatgtgg acgcctgtac tgcacgcggg gtctggctga ccttcgtgcc tgatctgttg   300
acggtcccga ctgccgagct ggcgatcgga ctggcggtgg ggctggggcg gcatttcgcg   360
gcagcagatg cattcgtccg ctctggcaag ttccagggct ggcagccaat tttctacggc   420
acggggctgg atggagcaac ggtcggcatt ctgggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttagccagc   600
tcggacttca tcctgctggc gcttcccttg aatgccgata ccctgcatct ggtcaacgcc   660
gagctgcttg ccctcgtacg gccgggcgct ctgcttgtaa accctgtcgt ggctctgta   720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattgacg ctgtgaacag cccgcccaag gccgagcctg ccgcatgttg a           1011

SEQ ID NO: 218           moltype = AA   length = 336
FEATURE                  Location/Qualifiers
REGION                   1..336
                         note = PDH-101 variant
source                   1..336
                         mol_type = protein
                         organism = synthetic construct
SEQUENCE: 218
MLPKLVITHR VHEEILQLLA PHCELITNQT DSTLTREEIL RRCADAQAMM AFMPDRVDAD    60
FLQACPELRV IGCALKGYDN FDVDACTARG VWLTFVPDLL TVPTAELAIG LAVGLGRHFR   120
AADAFVRSGK FQGWQPIFYG TGLDGATVGI LGMGAIGKAM ADRLQGWGAT LQYHSRTALD   180
TQTEQRLGLR QVACSELLAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNSPPK AEPAAC                             336

SEQ ID NO: 219           moltype = DNA   length = 1011
```

| FEATURE | Location/Qualifiers |
|---|---|
| misc_feature | 1..1011 |
| | note = PDH-101 variant |
| source | 1..1011 |
| | mol_type = other DNA |
| | organism = synthetic construct |

SEQUENCE: 219

```
atgctgccga aactcgttat aactcacaga gtacacgaag agatcctgca actgctggcg   60
ccacattgcg agctgataac caaccagacc gacagcgcgc tgacgcgcga ggaaattctg  120
cggcgctgtg cagatgctca ggcgatgatg cgttcatgc ccgatcgggt cgatgcagac   180
tttcttcaag cctgccctga gctgcgtgta atcggctgtg cgctcaaggg cttcgacaat  240
ttcgatgtgg acgcctgtac tgcacgcggg gtctggctga cctttgtgcc tgatctgttg  300
acggtcccga ctgccgagct ggcgatcgga ctggcggtgg ggctggggcg gcatttccgg  360
gcagcagatg cattcgtccg ctctggcaag ttccaggtgg cagcccaat ttttacggt   420
acggggctgg atggagcaac ggtcggcttc cttggcatgg gcgccatcgg aaaagccatg  480
gctgatcgct tgcagggatg gggcgcgacc ctgcagtacc actcgcggac agctctggat  540
acacaaaccg agcaacggct cggcctgcgc aggtggcgt gcagcgaact cttcgccagc   600
tcggacttca tcctgctggc gcttcccttg gcggcccaga ccctgcatct ggtcaacgcc  660
gagctgcttg ccctcgtacg gccgggcgct ctgcttgtaa accctgtcg tggctctgta   720
gtggatgaag ccgccgtgct cgcggcgctt gagcgaggcc agctcggcgg gtatgcggca  780
gatgtattcg aaatggaaga ctgggctcgc gcggaccggc cgcagcagat cgatcctgcg  840
ctgctcgcgc atccgaatac gctgttcact ccgcaccttg ggtcggcagt gcgcgcggtg  900
cgcctggaga ttgaacgttg tgcagcgcag aacatcctcc aggcattgcg aggtgagcgc  960
ccacaagacg ctgtgaaccg tctgcccaag gccgagcctg ccgcatgttg a         1011
```

| SEQ ID NO: 220 | moltype = AA length = 336 |
|---|---|
| FEATURE | Location/Qualifiers |
| REGION | 1..336 |
| | note = PDH-101 variant |
| source | 1..336 |
| | mol_type = protein |
| | organism = synthetic construct |

SEQUENCE: 220

```
MLPKLVITHR VHEEILQLLA PHCELITNQT DSTLTREEIL RRCADAQAMM AFMPDRVDAD   60
FLQACPELRV IGCALKGFDN FDVDACTARG VWLTFVPDLL TVPTAELAIG LAVGLGRHFR  120
AADAFVRSGK FQGWQPIFYG TGLDGATVGF LGMGAIGKAM ADRLQGWGAT LQYHSRTALD  180
TQTEQRLGLR QVACSELFAS SDFILLALPL AAQTLHLVNA ELLALVRPGA LLVNPCRGSV  240
VDEAAVLAAL ERGQLGGYAA DVFEMEDWAR ADRPQQIDPA LLAHPNTLFT PHLGSAVRAV  300
RLEIERCAAQ NILQALRGER PQDAVNRLPK AEPAAC                           336
```

| SEQ ID NO: 221 | moltype = DNA length = 1011 |
|---|---|
| FEATURE | Location/Qualifiers |
| misc_feature | 1..1011 |
| | note = PDH-101 variant |
| source | 1..1011 |
| | mol_type = other DNA |
| | organism = synthetic construct |

SEQUENCE: 221

```
atgctgccga aactcgttat aactcacaga gtacacgaag agatcctgca actgctggcg   60
ccacattgcg agctgataac caaccagacc gacagcacgc tgacgcgcga ggaaattctg  120
cggcgctgtg cagatgctca ggcgatgatg cgttcatgc ccgatcgggt cgatgcagac   180
tttcttcaag cctgccctga gctgcgtgta atcggctgtg cgctcaaggg cttcgacaat  240
ttcgatgtgg acgcctgtac tgcacgcggg gtctggctga cctttgtgcc tgatctgttg  300
acggtcccga ctgccgagct ggcgatcgga ctggcggtgg ggctggggcg gcatttccgg  360
gcagcagatg cattcgtccg ctctggcaag ttccaggtgg cagcccaat ttctacggt    420
acggggctgg atggagcaac ggtcggcttc cttggcatgg gcgccatcgg aaaagccatg  480
gctgatcgct tgcagggatg gggcgcgacc ctgcagtacc actcgcggac cctctggat   540
acacaaacag agcaacggct cggcctgcgc aggtggcgc ttagcgaact cttcgccagc   600
tcggacttca tcctgctggc gcttcccttg gcggcccaga ccctgcatct ggtcaacgac  660
gagctgcttg ccctcgtacg gccgggcgct ctgcttgtaa accctgtcg tggctctgta   720
gtggatgaag ccgccgtgct cgcggcgctt gagcgaggcc agctcggcgg gtatgcggca  780
gatgtattcg aaatggaaga ctgggctcgc gcggaccggc cgcagcagat cgatcctgcg  840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc  960
ccacaagacg ctgtgaaccg tctgcccaag gccgagcccg ccgcatgttg a         1011
```

| SEQ ID NO: 222 | moltype = AA length = 336 |
|---|---|
| FEATURE | Location/Qualifiers |
| REGION | 1..336 |
| | note = PDH-101 variant |
| source | 1..336 |
| | mol_type = protein |
| | organism = synthetic construct |

SEQUENCE: 222

```
MLPKLVITHR VHEEILQLLA PHCELITNQT DSTLTREEIL RRCADAQAMM AFMPDRVDAD   60
FLQACPELRV IGCALKGFDN FDVDACTARG VWLTFVPDLL TVPTAELAIG LAVGLGRHFR  120
AADAFVRSGK FQGWQPIFYG TGLDGATVGF LGMGAIGKAM ADRLQGWGAT LQYHSRTPLD  180
TQTEQRLGLR QVALSELFAS SDFILLALPL AAQTLHLVNA ELLALVRPGA LLVNPCRGSV  240
VDEAAVLAAL ERGQLGGYAA DVFEMEDWAR ADRPQQIDPA LLAHPNTLFT PHLGSAVRAV  300
```

RLEIERCAAQ NILQALRGER PQDAVNRLPK AEPAAC            336

SEQ ID NO: 223          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 223
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccattgtgcc tgatctgttg   300
acggtcccga ctgccgagct ggcgatcgga ctggcggtgg gtctggggcg gcatttccgg   360
gcagcagatg cattcgtccg ctctggcaag ttccagggct ggcagccaat tttctacggc   420
acggggctgg atggagcaac ggtcggcttc ctttggcatg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg gcggcccaga ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggca   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc   960
ccaatggacg ctgtgaaccg tctgcccaag gccgagcctg ccgcatgttg a           1011

SEQ ID NO: 224          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 224
MLPKLVITHR VHEEILQLLA PHCELITNQT DSTLTREEIL RRCADAQAMM AFMPDRVDAD    60
FLQACPELRV IGCALKGFDN FDVDACTARG VWLTIVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL AAQTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PMDAVNRLPK AEPAAC                            336

SEQ ID NO: 225          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 225
atgctgccga aactcgttat aactcacaga gtacacgaag agatcctgca actgctggcg    60
ccacattgcg agctgataac caaccagacc gacgtcacgc tgacgcgcga ggaaattctg   120
cggcgctgtg cagatgctca ggcgatgatg gcgttcatgc ccgatcgggt cgatatggac   180
tttcttcaag cctgccctga gctgagagta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gtctggggcg acatttccgg   360
gcagcagatg caattcgtcc gctctggcaa gttccagggc tggcagccaa tttctacggc   420
acggggctgg atggagcaac ggtcggcttc ctttggcatg gcgccatcgg aaaagccatg   480
gctgatcgct tgcagggatg gggcgcgacc ctgcagtacc actcgcggac cgctctggat   540
acacaaaccg agcaacggct cggcctgcgc catgtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggca   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc   960
ccaattgacg ctgtgaacga tctgcccaag gccgagcctg ccgcatgttg a           1011

SEQ ID NO: 226          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 226
MLPKLVITHR VHEEILQLLA PHCELITNQT DVTLTREEIL RRCADAQAMM AFMPDRVDMD    60
FLQACPELRV IGCALKGFDN FDVDACTARG VWLTFVPDLL TVPTAELAIG LAVGLGRHFR   120

```
AADEFVRSGK FQGWQPIFYG TGLDGATVGF LGMGAIGKAM ADRLQGWGAT LQYHSRSALD    180
TQTEQRLGLR HVACSELFAS SDFILLALPL NADTLHLVNA ELLALVRPGA LLVNPCRGSV    240
VDEAAVLAAL ERGQLGGYAA DVFEMEDWAR ADRPQQIDPA LLAHPNTLFT PHLGSAVRAV    300
RLEIERCAAQ NILQALRGER PIDAVNDLPK AEPAAC                              336

SEQ ID NO: 227            moltype = DNA   length = 1011
FEATURE                   Location/Qualifiers
misc_feature              1..1011
                          note = PDH-101 variant
source                    1..1011
                          mol_type = other DNA
                          organism = synthetic construct
SEQUENCE: 227
atgctgccga aactcgttat aactcacaga gtacacgaag agatcctgca actgctggcg    60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgctggc gcttcccttg aatgccgata cccgcatct ggtcaacgcc    660
gagctgcttg ccctcgtacg gccgggcgct gcttgtaa accctgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011

SEQ ID NO: 228            moltype = AA   length = 336
FEATURE                   Location/Qualifiers
REGION                    1..336
                          note = PDH-101 variant
source                    1..336
                          mol_type = protein
                          organism = synthetic construct
SEQUENCE: 228
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR    120
AADAFVRSGK FQGWQPIFYG TGLDGATVGF LGMGAIGKAM ADRLQGWGAT LQYHSRTALD    180
TQTEQRLGLR QVACSELFAS SDFILLALPL NADTPHLVNA ELLALVRPGA LLVNPCRGSV    240
VDEAAVLAAL ERGQLGGYAA DVFEMEDWAR ADRPQQIDPA LLAHPNTLFT PHLGSAVRAV    300
RLEIERCAAQ NILQALRGER PIDAVNRLPK AEPAAC                              336

SEQ ID NO: 229            moltype = DNA   length = 1011
FEATURE                   Location/Qualifiers
misc_feature              1..1011
                          note = PDH-101 variant
source                    1..1011
                          mol_type = other DNA
                          organism = synthetic construct
SEQUENCE: 229
atgctgccga aactcgttat aactcacaga gtacacgaag agatcctgca actgctggcg    60
ccacattgcg agctgataac caaccagacc gacagcacgc tgacgcgcga ggaaattctg    120
cggcgctgtg cagatgctca ggcgatgatg gcgttcatgc ccgatcgggt cgatgcagac    180
tttcttcaag cctgccctga gctgcgtgta atcggctgtg cgctcaaggg cttcgacaat    240
ttcgatgtgg acgcctgtac tgcacgcggg gtctggctga ccttcgtgcc tgatctgttg    300
acggtcccga ctgccgagct ggcgatcgga ctggcggtgg ggctggggcg gcatttccgg    360
gcagcagatg cattcgtccg ctctggcaag ttccagggct ggcagccaat tttctacggc    420
acggggctgg atggagcaac ggtcggcttc cttggcatgg gcgccatcgg aaaagccatg    480
gctgatcgct tgcagggatg gggcgcgacc ctgcagtacc actcgcggac agctctggat    540
acacaaaccg agcaacggct cggcctgcgc caggtggcgt gcagcgaact cttcgccagc    600
tcggacttca tcctgaatgc gcttcccttg aatgccgata cccgcatct ggtcaacgcc    660
gagctgcttg ccctcgtacg gccgggcgct gcttgtaa accctgtcg tggctctgta    720
gtggatgaag ccgccgtgct cgcggcgctt gagcgaggcc agctcggcgg gtatgcggcg    780
gatgtattcg aaatggaaga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgttg a            1011

SEQ ID NO: 230            moltype = AA   length = 336
FEATURE                   Location/Qualifiers
REGION                    1..336
                          note = PDH-101 variant
source                    1..336
                          mol_type = protein
                          organism = synthetic construct
```

-continued

```
SEQUENCE: 230
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILNALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 231          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 231
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccgt tgccgagct ggcgatcgga ctggcgtgg ggctggggcg gcatttccgg     360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcg   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a           1011

SEQ ID NO: 232          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 232
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPFAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 233          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 233
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccgc ttgccgagct ggcgatcgga ctggcgtgg ggctggggcg gcatttccgg    360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a           1011

SEQ ID NO: 234          moltype = AA  length = 336
FEATURE                 Location/Qualifiers
REGION                  1..336
                        note = PDH-101 variant
```

```
source                          1..336
                                mol_type = protein
                                organism = synthetic construct
SEQUENCE: 234
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPLAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 235                  moltype = DNA   length = 1011
FEATURE                         Location/Qualifiers
misc_feature                    1..1011
                                note = PDH-101 variant
source                          1..1011
                                mol_type = other DNA
                                organism = synthetic construct
SEQUENCE: 235
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc cgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctgggggcg gcatttccgg   360
gcagcagatg cattcgtccg ctctggcaag ttccagggg ggcagccaat ttttctacggc   420
acggggctgg atggagcaac ggtcggcttc cttggcatgg gcgccatcgg aaaagcatg    480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg   780
gatgtattcg aaatgtctga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a            1011

SEQ ID NO: 236                  moltype = AA    length = 336
FEATURE                         Location/Qualifiers
REGION                          1..336
                                note = PDH-101 variant
source                          1..336
                                mol_type = protein
                                organism = synthetic construct
SEQUENCE: 236
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPLAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMSDWAR ADRPQQIDPA LLAHPNTLFT PHLGSAVRAV   300
RLEIERCAAQ NILQALRGER PIDAVNRLPK AEPAAC                             336

SEQ ID NO: 237                  moltype = DNA   length = 1011
FEATURE                         Location/Qualifiers
misc_feature                    1..1011
                                note = PDH-101 variant
source                          1..1011
                                mol_type = other DNA
                                organism = synthetic construct
SEQUENCE: 237
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc cgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctgggggcg gcatttccgg   360
gcagcagatg cattcgtccg ctctggcaag ttccagggct ggcagccaat ttttctacggc   420
acggggctgg atggagcaac ggtcggcttc cttggcatgg gcgccatcgg aaaagcatg    480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agctcggcgg gtatgcggcg   780
gatccttcg aaatgaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a            1011

SEQ ID NO: 238                  moltype = AA    length = 336
```

```
FEATURE                 Location/Qualifiers
REGION                  1..336
                        note = PDH-101 variant
source                  1..336
                        mol_type = protein
                        organism = synthetic construct
SEQUENCE: 238
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DPFEMEDWAR ADRPQQIDPA LLAHPNTLFT PHLGSAVRAV   300
RLEIERCAAQ NILQALRGER PIDAVNRLPK AEPAAC                             336

SEQ ID NO: 239          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 239
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcggtgg gctggggcg gcatttccgg    360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt agcgaggcc agtcggcgg gtatgcggc    780
gatgatttcg aaatgaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgttg a           1011

SEQ ID NO: 240          moltype = AA  length = 336
FEATURE                 Location/Qualifiers
REGION                  1..336
                        note = PDH-101 variant
source                  1..336
                        mol_type = protein
                        organism = synthetic construct
SEQUENCE: 240
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DDFEMEDWAR ADRPQQIDPA LLAHPNTLFT PHLGSAVRAV   300
RLEIERCAAQ NILQALRGER PIDAVNRLPK AEPAAC                             336

SEQ ID NO: 241          moltype = DNA  length = 1011
FEATURE                 Location/Qualifiers
misc_feature            1..1011
                        note = PDH-101 variant
source                  1..1011
                        mol_type = other DNA
                        organism = synthetic construct
SEQUENCE: 241
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgcgg acgcctgtac tgcacgcggg gtctggctga ccttcgtgcc tgatctgttg   300
acggtcccga ctgccgagct ggcgatcgga ctggcggtgg gctggggcg gcatttccgg    360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt agcgaggcc agtcggcgg gtatgcggc    780
gatgtattcg aaatgcgga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
```

```
ccaattgacg ctgtgaaccg tctgcccaag gccgagcctg ccgcatgttg a           1011

SEQ ID NO: 242          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 242
MLPKLVITHR VHEEILQLLA PHCELITNQT DSTLTREEIL RRCADAQAMM AFMPDRVDAD    60
FLQACPELRV IGCALKGFDN FDADACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMADWAR ADRPQQIDPA LLAHPNTLFT PHLGSAVRAV   300
RLEIERCAAQ NILQALRGER PIDAVNRLPK AEPAAC                             336

SEQ ID NO: 243          moltype = DNA   length = 1011
FEATURE                 Location/Qualifiers
misc_feature            1..1011
                        note = PDH-101 variant
source                  1..1011
                        mol_type = other DNA
                        organism = synthetic construct
SEQUENCE: 243
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgcgg acgcctgtac tgcacgcggg gtctggctga ccttcgtgcc tgatcgtttg   300
acggtcccga ctgccgagct ggcgatcgga ctggcggtgg gctgggggcg gcatttccgg   360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt gagcgaggcc agtcgggcgg gtatgcggcg   780
gatgtattcg aaatggaaga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattaatg cggtgaaccg tctgcccaag gccgagcctg ccgcatgttg a           1011

SEQ ID NO: 244          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 244
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PINAVNRLPK AEPAAC                             336

SEQ ID NO: 245          moltype = DNA   length = 1008
FEATURE                 Location/Qualifiers
misc_feature            1..1008
                        note = PDH-101 variant
source                  1..1008
                        mol_type = other DNA
                        organism = synthetic construct
SEQUENCE: 245
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgcgg acgcctgtac tgcacgcggg gtctggctga ccttcgtgcc tgatcgtttg   300
acggtcccgt ggccgagct ggcgatcgga ctggcggtgg gctgggggcg gcatttccgg   360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgaatgc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt gagcgaggcc agtcgggcgg gtatgcggcg   780
```

```
gatgtgttcg aaatggagga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgt              1008

SEQ ID NO: 246          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 246
MLPKLVITHR VHEEILQLLA PHCELITNQT DSTLTREEIL RRCADAQAMM AFMPDRVDAD    60
FLQACPELRV IGCALKGFDN FDADACTARG VWLTFVPDLL TVPLAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILNALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 247          moltype = DNA   length = 1008
FEATURE                 Location/Qualifiers
misc_feature            1..1008
                        note = PDH-101 variant
source                  1..1008
                        mol_type = other DNA
                        organism = synthetic construct
SEQUENCE: 247
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgta ccctcaaggg cttcgacaat   240
ttcgatgcgc acgcctgtac tgcacgcggg gtctggctga ccttcgtgcc tgatctgttg   300
acggtcccga ctgccgagct ggccgatcgga ctggcggtgg ggctggggcg gcatttccgg   360
gcagcagatg cattcgtccg ctctggcaag ttccagggct ggcagccaat ttttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgaatgc gcttcccttg aatgccgata ccctgcatct ggtcaacgcc   660
gagctgcttg ccctcgtacg gccgggcgct ctgcttgtaa accccctgtcg tggctctgta   720
gtggatgaag ccgccgtgct cgcggcgctt gagcgaggcc agctcggcgg gtatgctggcg   780
gatgtgttcg aaatggagga ctgggctcgc gcggaccggc cgcagcagat cgatcctgcg   840
ctgctcgcgc atccgaatac gctgttcact ccgcaccttg ggtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctg ccgcatgt              1008

SEQ ID NO: 248          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 248
MLPKLVITHR VHEEILQLLA PHCELITNQT DSTLTREEIL RRCADAQAMM AFMPDRVDAD    60
FLQACPELRV IGCTLKGFDN FDADACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILNALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 249          moltype = DNA   length = 1008
FEATURE                 Location/Qualifiers
misc_feature            1..1008
                        note = PDH-101 variant
source                  1..1008
                        mol_type = other DNA
                        organism = synthetic construct
SEQUENCE: 249
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgcgc acgcctgtac tgcacgcggg gtctggctgt ccttcgtgcc tgatctgttg   300
acggtcccgt tggccgagct ggccgatcgga ctggcggtgg ggctggggcg gcatttccgg   360
gcagcagatg cattcgtccg ctctggcaag ttccagggct ggcagccaat ttttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
```

```
tcggacttca tcctgctggc gcttcccttg aatgccgata ccctgcatct ggtcaacgcc    660
gagctgcttg ccctcgtacg gccgggcgct ctgcttgtaa accccgtcg tggctctgta     720
gtggatgaag ccgccgtgct cgcggcgctt gagcgaggcc agctcggcgg gtatgcggcg    780
gatctgttcg aaatggagga ctgggctcgc gcggaccggc cgcagcagat cgatcctgcg    840
ctgctcgcgc atccgaatac gctgttcact ccgcaccttg ggtcggcagt gcgcgcggtg    900
cgcctggaga ttgaacgttg tgcagcgcag aacatcctcc aggcattgcg aggtgagcgc    960
ccaattgacg ctgtgaaccg tctgcccaag gccgagcctg ccgcatgt                1008
```

SEQ ID NO: 250          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 250
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPLAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DLFEMEDWAR ADRPQQIDPA LLAHPNTLFT PHLGSAVRAV   300
RLEIERCAAQ NILQALRGER PIDAVNRLPK AEPAAC                             336

SEQ ID NO: 251          moltype = DNA   length = 1008
FEATURE                 Location/Qualifiers
misc_feature            1..1008
                        note = PDH-101 variant
source                  1..1008
                        mol_type = other DNA
                        organism = synthetic construct
SEQUENCE: 251
```
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagca   180
tttcttcaag cctgccctga gctcgtgta atcggctgtg ccctcaaggg cttcgacaat    240
ttcgatgtgg acgcctgtac tgcacgcggg gtctggctga ccttcgtgcc tgatctgttg   300
acggtcccgt tggccgagct ggcgatcgga ctggcgtgg ggctggggcg gcatttccgg    360
gcagcagatg cattcgtccg ctctggcaag ttccagggct ggcagccaat ttctacggc    420
acggggctgg atggagcaac ggtcggcttc ctttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgaatgc gcttcccttg aatgccgata ccctgcatct ggtcaacgcc    660
gagctgcttg ccctcgtacg gccgggcgct ctgcttgtaa accccgtcg tggctctgta   720
gtggatgaag ccgccgtgct cgcggcgctt gagcgaggcc agctcggcgg gtatgcggcg   780
gatgtgttcg aaatggagga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc   960
ccaattgacg ctgtgaaccg tctgcccaag gccgagcctg ccgcatgt               1008

SEQ ID NO: 252          moltype = AA   length = 336
FEATURE                 Location/Qualifiers
REGION                  1..336
                        note = PDH-101 variant
source                  1..336
                        mol_type = protein
                        organism = synthetic construct
SEQUENCE: 252
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPLAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILNALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336

SEQ ID NO: 253          moltype = DNA   length = 1008
FEATURE                 Location/Qualifiers
misc_feature            1..1008
                        note = PDH-101 variant
source                  1..1008
                        mol_type = other DNA
                        organism = synthetic construct
SEQUENCE: 253
```
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctcgtgta atcggctgtg cgctcaaggg cttcgacaat    240
ttcgatgtgg acgcctgtac tgcacgcggg gtctggctga ccttcgtgcc tgatctgttg   300
acggtcccgt tggccgagct ggcgatcgga ctggcgtgg ggctggggcg gcatttccgg    360
gcagcagatg cattcgtccg ctctggcaag ttccagggct ggcagccaat ttctacggc    420
```

```
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt gagcgaggcc agctcggcgg gtatgcgggc   780
gatgtattcg aaatggaaga ctgggctcgc gcggaccggc cgcagcagat cgatcctgcg   840
ctgctcgcgc atccgaatac gctgttcact ccgcaccttg gcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctc ccgcatgt              1008
```

```
SEQ ID NO: 254            moltype = AA  length = 336
FEATURE                   Location/Qualifiers
REGION                    1..336
                          note = PDH-101 variant
source                    1..336
                          mol_type = protein
                          organism = synthetic construct
SEQUENCE: 254
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGRAVRAV   300
RLEIERCAAQ NILQALRGER PIDAVNRLPK AEPAAC                             336
```

```
SEQ ID NO: 255            moltype = DNA  length = 1008
FEATURE                   Location/Qualifiers
misc_feature              1..1008
                          note = PDH-101 variant
source                    1..1008
                          mol_type = other DNA
                          organism = synthetic construct
SEQUENCE: 255
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
ttcgatgtgg acgcctgtac tgcacgcggg gtctggctga ccttcgggcc tgatctgttg   300
acggtcccga ctgccgagct ggcgatcgga ctggcggtgg gctggggcg gcatttccgg   360
gcagcagatg cattcgtccg ctctggcaag ttccagggct ggcagccaat tttctacggc   420
acggggctgg atggagcaac ggtcggcttc cttggcatgg gcgccatcgg aaaagccatg   480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta   720
gtggatgaag ccgccgtgct cgcggcgctt gagcgaggcc agctcggcgg gtatgcgggc   780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg   900
cgcctggaga ttgaacgttg tgcagcgcag aacatcctcc aggcattgcg aggtgagcgc   960
ccaattgacg ctgtgaaccg tctgcccaag gccgagcctc ccgcatgt              1008
```

```
SEQ ID NO: 256            moltype = AA  length = 336
FEATURE                   Location/Qualifiers
REGION                    1..336
                          note = PDH-101 variant
source                    1..336
                          mol_type = protein
                          organism = synthetic construct
SEQUENCE: 256
MLPKLVITHR VHEEILQLLA PHCELITNQT DSTLTREEIL RRCADAQAMM AFMPDRVDAD    60
FLQACPELRV IGCALKGFDN FDVDACTARG VWLTFGPDLL TVPTAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                             336
```

```
SEQ ID NO: 257            moltype = DNA  length = 1008
FEATURE                   Location/Qualifiers
misc_feature              1..1008
                          note = PDH-101 variant
source                    1..1008
                          mol_type = other DNA
                          organism = synthetic construct
SEQUENCE: 257
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctgcgtgta atcggctgtg cgctcaaggg cttcgacaat   240
```

```
ttcgatgtgg acgcctgtac tgcacgcggg gtctggctga ccttcgtgcc tgatctgttg   300
acggtcccga tggccgagct ggcgatcgga ctggcgggcg ggctggggcg gcatttccgg   360
gcagcagatg cattcgtccg ctctggcaag ttccagggct ggcagccaat tttctacggc   420
acggggctgg atggagcaac ggtcggcttc cttggcatgg cgccatcgg aaaagccatg    480
gctgatcgct tgcagggatg gggcgcgacc ctgcagtacc actcgcggac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agtcggcgg gtatgcggcg    780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc   960
ccaattgacg ctgtgaaccg tctgcccaag gccgagcctg ccgcatgt               1008

SEQ ID NO: 258           moltype = AA   length = 336
FEATURE                  Location/Qualifiers
REGION                   1..336
                         note = PDH-101 variant
source                   1..336
                         mol_type = protein
                         organism = synthetic construct
SEQUENCE: 258
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPMAELAIG LAVGLGRHFR   120
AADAFVRSGK FQGWQPIFYG TGLDGATVGF LGMGAIGKAM ADRLQGWGAT LQYHSRTALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                            336

SEQ ID NO: 259           moltype = DNA   length = 1008
FEATURE                  Location/Qualifiers
misc_feature             1..1008
                         note = PDH-101 variant
source                   1..1008
                         mol_type = other DNA
                         organism = synthetic construct
SEQUENCE: 259
atgctgccga aactcgttat aactcacaga gtacacgaag agatcctgca actgctggcg    60
ccacattgcg agctgataac caaccagacc gacagcacgc tgacgcgcga ggaaattctg   120
cggcgctgtg cagatgctca ggcgatgatg gcgttcatgc ccgatcgggt cgatgcagac   180
tttcttcaag cctgccctga gctcgtgta atcggctgtg cgctcaaggg cttcgacaat   240
ttcgatgtgg acgcctgtac tgcacgcggg gtctggctga ccttcgtgcc tgatctgttg   300
acggtcccga ctgccgagct ggcgatcgga ctggcgggcg ggctggggcg gcatttccgg   360
gcagcagatg cattcgtccg ctctggcaag ttccagggct ggcagccaat tttctacggc   420
acggggctgg atggagcaac ggtcggcttc cttggcatgg cgccatcgg aaaagccatg    480
gctgatcgct tgcagggatg gggcgcgacc ctgcagtacc acgaagcgac agctctggat   540
acacaaaccg agcaacggct cggcctgcgc caggtggcgt gcagcgaact cttcgccagc   600
tcggacttca tcctgctggc gcttcccttg aatgccgata ccctgcatct ggtcaacgcc   660
gagctgcttg ccctcgtacg gccgggcgct ctgcttgtaa accctgtcg tggctctgta    720
gtggatgaag ccgccgtgct cgcggcgctt gagcgaggcc agtcggcgg gtatgcggcg    780
gatgtattcg aaatggaaga ctgggctcgc gcggaccggc cgcagcagat cgatcctgcg   840
ctgctcgcgc atccgaatac gctgttcact ccgcaccttg gtcggcagt gcgcgcggtg    900
cgcctggaga ttgaacgttg tgcagcgcag aacatcctcc aggcattgcg aggtgagcgc   960
ccaattgacg ctgtgaaccg tctgcccaag gccgagcctg ccgcatgt               1008

SEQ ID NO: 260           moltype = AA   length = 336
FEATURE                  Location/Qualifiers
REGION                   1..336
                         note = PDH-101 variant
source                   1..336
                         mol_type = protein
                         organism = synthetic construct
SEQUENCE: 260
MLPKLVITHR VHEEILQLLA PHCELITNQT DSTLTREEIL RRCADAQAMM AFMPDRVDAD    60
FLQACPELRV IGCALKGFDN FDVDACTARG VWLTFVPDLL TVPTAELAIG LAVGLGRHFR   120
AADAFVRSGK FQGWQPIFYG TGLDGATVGF LGMGAIGKAM ADRLQGWGAT LQYHEATALD   180
TQTEQRLGLR QVACSELFAS SDFILLALPL NADTLHLVNA ELLALVRPGA LLVNPCRGSV   240
VDEAAVLAAL ERGQLGGYAA DVFEMEDWAR ADRPQQIDPA LLAHPNTLFT PHLGSAVRAV   300
RLEIERCAAQ NILQALRGER PIDAVNRLPK AEPAAC                            336
```